(12) United States Patent
Mark et al.

(10) Patent No.: US 11,412,923 B2
(45) Date of Patent: Aug. 16, 2022

(54) SURGICAL ACCESS ASSEMBLY AND METHOD OF USING SAME

(71) Applicant: Nico Corporation, Indianapolis, IN (US)

(72) Inventors: Joseph L. Mark, Indianapolis, IN (US); Brian C. Dougherty, Terre Haute, IN (US); Adam Furore, Warsaw, IN (US); Mick Trompen, Westfield, IN (US)

(73) Assignee: NICO CORPORATION, Indianapolis, IN (US)

( * ) Notice: Subject to any disclaimer, the term of this patent is extended or adjusted under 35 U.S.C. 154(b) by 243 days.

(21) Appl. No.: 16/208,085

(22) Filed: Dec. 3, 2018

(65) Prior Publication Data

US 2019/0099070 A1 Apr. 4, 2019
US 2022/0192481 A9 Jun. 23, 2022

Related U.S. Application Data

(60) Continuation of application No. 14/847,863, filed on Sep. 8, 2015, now Pat. No. 10,143,366, which is a
(Continued)

(51) Int. Cl.
*A61B 1/32* (2006.01)
*A61B 90/30* (2016.01)
(Continued)

(52) U.S. Cl.
CPC .............. *A61B 1/32* (2013.01); *A61B 1/0014* (2013.01); *A61B 1/0607* (2013.01);
(Continued)

(58) Field of Classification Search
CPC ........ A61B 1/32; A61B 1/0014; A61B 1/0607; A61B 1/00154; A61B 90/30;
(Continued)

(56) References Cited

U.S. PATENT DOCUMENTS 2,006,358 A 7/1935 Kurkjian
3,690,323 A 9/1972 Wortman et al.
(Continued)

FOREIGN PATENT DOCUMENTS

GB 2493165 A 1/2013
JP 201104323 A1 4/2001
(Continued)

OTHER PUBLICATIONS

PCT International Search Report dated May 9, 2014 for PCT/US2014/015071.
(Continued)

*Primary Examiner* — Erich G Herbermann
(74) *Attorney, Agent, or Firm* — Brooks Kushman, P.C.

(57) ABSTRACT

An illuminating ring assembly is disclosed. The illuminating ring configured to be used with a surgical access element. The illuminating ring assembly comprises a housing defined by a cover and a wall member extending from the cover, wherein the cover and wall member cooperate to define a cavity therein, a light element configured to be disposed with the cavity, and an attachment mechanism configured to selectively attach the housing to a surgical access element. Wherein the cover and the light element both include an opening therethrough.

16 Claims, 33 Drawing Sheets

Related U.S. Application Data division of application No. 13/786,186, filed on Mar. 5, 2013, now Pat. No. 9,161,820, which is a continuation-in-part of application No. 13/280,015, filed on Oct. 24, 2011, now Pat. No. 9,770,261, which is a continuation-in-part of application No. 11/665,666, filed as application No. PCT/US2005/039185 on Oct. 28, 2005.

(60) Provisional application No. 60/623,094, filed on Oct. 28, 2004.

(51) Int. Cl.

| | |
|---|---|
| *A61B 17/32* | (2006.01) |
| *A61B 17/34* | (2006.01) |
| *A61M 39/06* | (2006.01) |
| *A61B 1/00* | (2006.01) |
| *A61B 1/06* | (2006.01) |
| *A61B 17/02* | (2006.01) |
| *A61B 90/10* | (2016.01) |
| *A61B 90/00* | (2016.01) |
| *A61B 34/20* | (2016.01) |
| *A61B 6/12* | (2006.01) |
| *A61B 8/08* | (2006.01) |
| *A61B 8/12* | (2006.01) |
| *A61B 5/00* | (2006.01) |
| *A61B 5/055* | (2006.01) |
| *A61B 5/06* | (2006.01) |
| *A61B 17/3205* | (2006.01) |

(52) U.S. Cl.
CPC .. *A61B 17/0218* (2013.01); *A61B 17/320016* (2013.01); *A61B 17/3417* (2013.01); *A61B 17/3421* (2013.01); *A61B 17/3423* (2013.01); *A61B 90/30* (2016.02); *A61M 39/06* (2013.01); *A61B 1/00154* (2013.01); *A61B 5/0066* (2013.01); *A61B 5/0071* (2013.01); *A61B 5/055* (2013.01); *A61B 5/061* (2013.01); *A61B 6/12* (2013.01); *A61B 8/0808* (2013.01); *A61B 8/0841* (2013.01); *A61B 8/12* (2013.01); *A61B 17/3205* (2013.01); *A61B 90/361* (2016.02); *A61B 2017/320064* (2013.01); *A61B 2017/3456* (2013.01); *A61B 2034/2051* (2016.02); *A61B 2090/062* (2016.02); *A61B 2090/0807* (2016.02); *A61B 2090/0811* (2016.02); *A61B 2090/103* (2016.02); *A61B 2090/306* (2016.02); *A61B 2090/309* (2016.02); *A61B 2090/3614* (2016.02); *A61M 2039/0626* (2013.01)

(58) Field of Classification Search
CPC ............. A61B 90/361; A61B 17/0218; A61B 17/320016; A61B 17/3417; A61B 17/3421; A61B 17/3423; A61B 2034/2051; A61B 2090/062; A61B 2090/0807; A61B 2090/0811; A61B 2090/103; A61B 2090/306; A61B 2090/309; A61B 2090/3614; A61B 5/0066; A61B 5/0071; A61B 5/055; A61B 5/061; A61B 2017/3456; A61B 2017/320064; A61B 17/3205; A61B 8/12; A61B 8/0841; A61B 8/0808; A61B 6/12; A61M 39/06; A61M 2039/0626
See application file for complete search history.

(56) References Cited

U.S. PATENT DOCUMENTS

| | | |
|---|---|---|
| 3,825,007 A | 7/1974 | Rand |
| 4,386,602 A | 6/1983 | Sheldon et al. |
| 4,638,798 A | 1/1987 | Shelden et al. |
| 4,729,070 A | 3/1988 | Chiu |
| 5,183,464 A | 2/1993 | Dubrui et al. |
| 5,217,441 A | 6/1993 | Shichman |
| 5,320,611 A | 6/1994 | Bonutti et al. |
| 5,431,676 A | 7/1995 | Dubrul et al. |
| 5,490,843 A * | 2/1996 | Hildwein ............... A61B 17/29 604/164.03 |
| 5,676,689 A | 10/1997 | Kensey et al. |
| 5,716,369 A | 2/1998 | Riza |
| 5,735,865 A | 4/1998 | Schaumann et al. |
| 5,860,996 A | 1/1999 | Urban et al. |
| 6,047,218 A | 4/2000 | Whayne et al. |
| 6,052,184 A | 4/2000 | Reed |
| 6,129,685 A | 10/2000 | Howard, III |
| 6,179,826 B1 | 1/2001 | Aebischer et al. |
| 6,224,608 B1 | 5/2001 | Ciccolella |
| 6,226,548 B1 | 5/2001 | Foley et al. |
| 6,245,052 B1 | 6/2001 | Orth et al. |
| 6,280,399 B1 | 8/2001 | Rossin et al. |
| 6,293,952 B1 | 9/2001 | Brosens et al. |
| 6,331,180 B1 | 12/2001 | Cosman et al. |
| 6,374,135 B1 | 4/2002 | Bucholz |
| 6,416,520 B1 | 7/2002 | Kynast et al. |
| 6,550,952 B1 | 4/2003 | Hulse et al. |
| 6,551,240 B2 | 4/2003 | Henzler |
| 6,663,260 B1 | 12/2003 | Tieszen |
| 6,669,685 B1 | 12/2003 | Rizoiu et al. |
| 6,685,630 B2 | 2/2004 | Sauer et al. |
| 6,942,634 B2 | 9/2005 | Odland |
| 7,429,117 B2 | 9/2008 | Pohlert et al. |
| D611,178 S | 3/2010 | Waring |
| 7,823,801 B2 | 11/2010 | McGarry et al. |
| D630,350 S | 1/2011 | Lin |
| 7,862,542 B1 | 1/2011 | Harmon, Sr. |
| 8,192,445 B2 | 6/2012 | Parmer et al. |
| 8,207,821 B2 | 6/2012 | Roberge et al. |
| 8,578,884 B2 | 11/2013 | Hawk |
| 8,960,973 B1 | 2/2015 | Kathawate et al. |
| 2001/0050264 A1 | 12/2001 | Schorner |
| 2002/0183594 A1 | 12/2002 | Beane et al. |
| 2003/0073934 A1 | 4/2003 | Putz |
| 2003/0097149 A1 | 5/2003 | Edwards et al. |
| 2004/0024291 A1 | 2/2004 | Zinkel |
| 2004/0059375 A1 | 3/2004 | Ginn et al. |
| 2004/0068172 A1 | 4/2004 | Nowinski et al. |
| 2004/0102804 A1 | 5/2004 | Chin |
| 2004/0143167 A1 | 7/2004 | Branch et al. |
| 2004/0143169 A1* | 7/2004 | Branch .................. A61B 90/36 600/245 |
| 2004/0176801 A1 | 9/2004 | Edwards et al. |
| 2004/0186346 A1 | 9/2004 | Smith et al. |
| 2004/0215143 A1 | 10/2004 | Brady et al. |
| 2005/0098932 A1 | 5/2005 | Panosian |
| 2005/0107820 A1 | 5/2005 | Forsberg et al. |
| 2006/0167357 A1 | 7/2006 | Lauritsch et al. |
| 2006/0224045 A1 | 10/2006 | Whipple et al. |
| 2006/0247500 A1 | 11/2006 | Voegele et al. |
| 2007/0100210 A1 | 5/2007 | Selover et al. |
| 2007/0100211 A1 | 5/2007 | Selover et al. |
| 2007/0228753 A1 | 10/2007 | Dugal et al. |
| 2007/0270898 A1 | 11/2007 | Lillehei |
| 2007/0276191 A1 | 11/2007 | Selover et al. |
| 2008/0103366 A1 | 5/2008 | Banchieri et al. |
| 2008/0109026 A1 | 5/2008 | Kassam |
| 2008/0147018 A1 | 6/2008 | Squilla et al. |
| 2009/0048622 A1 | 2/2009 | Wilson |
| 2009/0118587 A1 | 5/2009 | Voegele et al. |
| 2009/0259097 A1 | 10/2009 | Thompson |
| 2009/0312611 A1 | 12/2009 | Mangiardi |
| 2010/0010315 A1 | 1/2010 | Mangiardi |
| 2010/0029147 A1 | 2/2010 | Shrum et al. |
| 2010/0081882 A1 | 4/2010 | Hess et al. |

(56) References Cited

U.S. PATENT DOCUMENTS

| | | | |
|---|---|---|---|
| 2010/0130076 A1 | 5/2010 | Shrum et al. | |
| 2010/0142215 A1 | 6/2010 | Waring | |
| 2010/0188492 A1* | 7/2010 | Jacobsen | A61B 1/00188 |
| | | | 348/68 |
| 2010/0274081 A1 | 10/2010 | Okonlewski | |
| 2010/0284184 A1 | 11/2010 | Yang | |
| 2010/0324488 A1 | 12/2010 | Smith | |
| 2011/0005110 A1 | 1/2011 | Wieneke | |
| 2011/0094204 A1 | 4/2011 | Bouillon et al. | |
| 2011/0112360 A1 | 5/2011 | Swann et al. | |
| 2012/0038293 A1 | 2/2012 | Guerrieri et al. | |
| 2012/0071748 A1 | 3/2012 | Mark et al. | |
| 2012/0123327 A1 | 5/2012 | Miller | |
| 2012/0224375 A1 | 9/2012 | Zaderej et al. | |
| 2012/0289816 A1 | 11/2012 | Mark et al. | |
| 2012/0310269 A1 | 12/2012 | Fearnot et al. | |
| 2013/0044485 A1 | 2/2013 | Zaderej et al. | |
| 2013/0058087 A1 | 3/2013 | Chang | |
| 2013/0107508 A1 | 5/2013 | Rockrohr et al. | |
| 2013/0188352 A1 | 7/2013 | Boyer et al. | |
| 2013/0204287 A1 | 8/2013 | Mark et al. | |
| 2013/0241419 A1 | 9/2013 | Ghafoori et al. | |
| 2014/0029258 A1 | 1/2014 | Schroll et al. | |
| 2014/0126202 A1 | 5/2014 | Kachala | |
| 2014/0134568 A1 | 5/2014 | Heinrich et al. | |
| 2014/0313766 A1 | 10/2014 | Krupa et al. | |

FOREIGN PATENT DOCUMENTS

| | | |
|---|---|---|
| RU | 2009124446 A1 | 1/2011 |
| WO | 2006017507 A2 | 2/2006 |
| WO | 2006050047 A2 | 5/2006 |
| WO | 2007002251 A2 | 1/2007 |
| WO | 2007055983 A2 | 5/2007 |
| WO | 2007056010 A2 | 5/2007 |
| WO | 2008066543 A1 | 6/2008 |
| WO | 2008121294 A1 | 10/2008 |

OTHER PUBLICATIONS

Response to Non-Final Office Action dated Nov. 10, 2011 for U.S. Appl. No. 11/665,666.
Final Office Action dated May 30, 2012 for U.S. Appl. No. 11/665,666.
Response to Final Office Action dated May 30, 2012 for U.S. Appl. No. 11/665,666.
PCT International Search Report and Opinion dated Apr. 9, 2013 for PCT/US2012/061568.
Office Action dated May 9, 2013 for U.S. Appl. No. 11/665,666.
Non-Final Office Action dated Nov. 10, 2011 for U.S. Appl. No. 11/665,666.
PCT International Search Report dated Jun. 20, 2006 for PCT/US05/39185.
Wedeen, Van J., et al., "The Geometric Structure of the Brain Fiber Pathways." Science 335, 1628 (2012).
A. Schupak, "A Healthy Glow Florescent imaging helps surgeons cut more cancer cells," Poplar Science, Feb. 2011.
Modern Medicine, "New Device May Help Surgeons Resect Brain Tumors," "Fluoresence spectroscopy helsp neurosurgeons identify hard-to-see tumor tissue." (Jan. 31, 2011).
Nader Sanal, M.D., et al., "Intraoperative Confocal Microscopy for Brain Tumors: A Feasibility Analysis in Humans," www.neurosurgery-online.com (Jun. 2011).
Juan C. Fernandez-Miranda, M.D. et al., "High-definition fiber tracking guidance for intraparenchmyal endoscopi port surgery," J. Neurosurg/vol. 113/Nov. 2010.
Manuel Dujovny, et al., "Brain Retractor Systems," Neurological Research, vol. 37, No. 7, (2010).
T. Nakano, et al., "Endoscopic Treatment for Deep-seated or Multiple Intraparenchymal Tumoers: Technical Note," Dept. of Neurosurgery, Hirosaki University Graduate School of Medicine. (2009).
Amin B. Kassam, et al., "Completely endoscopic resection of intraparenchymal brain tumors," J. Neurosrug./vol. 110/Jan. 2009.
K. Ogura, et al., "Neurosurgical Technique, New microsurgical technique for intraparenchymal lesions of the brain: transcylinder approach," Acta Neurochir (Wien)(2006).
Chu-Chung Chen M.D., et al., "A stainless steel sheaht for endoscopic surgery and tis application in surgical evacuation of putanimal haemorrihage," Journal of Clniical Neuroscience (2005).
O. Barlas, et al., Clincial Article, Stereotractically guided microsurgical removal of colloid cysts, Acta Neurochir (Wien)(2004).
Tetsuhiro Nishihara, M.D., et al., "A transparent sheath for endoscopic surgery and its application in surgical evacuation of spontaneous intracerebral hematomas," J. Neurosurg/vol. 92/Jun. 2000.
Donald M. O'Rourke, M.D., et al., "Vycor Medical, Inc.—Business Summary," www.vycormedical.com.
PCT International Search Report dated Jul. 24, 2014 for PCT/US2014/015755.

* cited by examiner

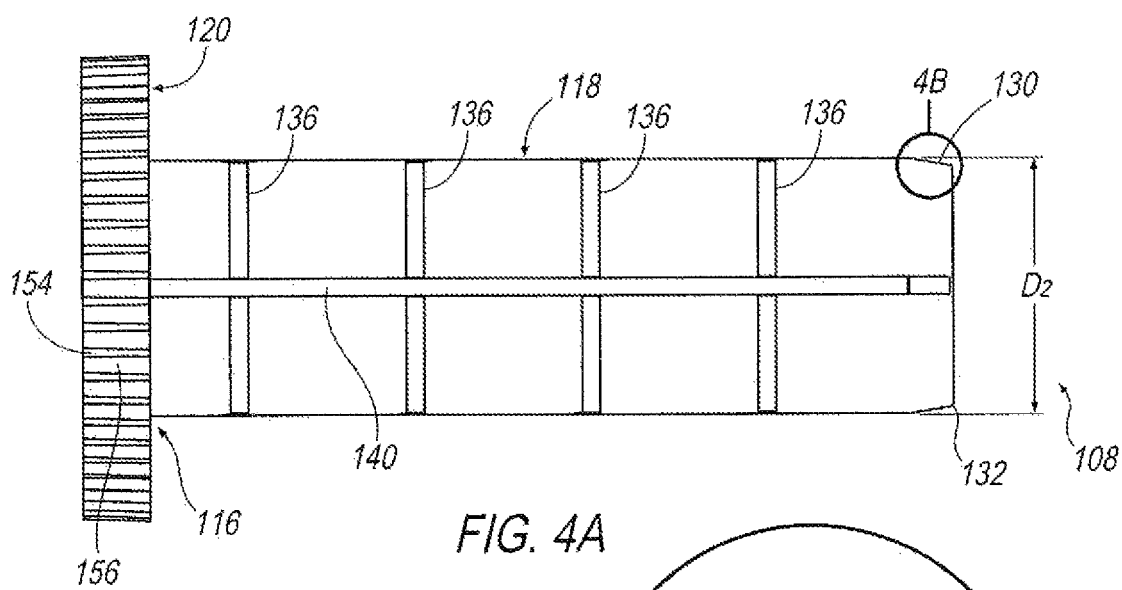
FIG. 4A
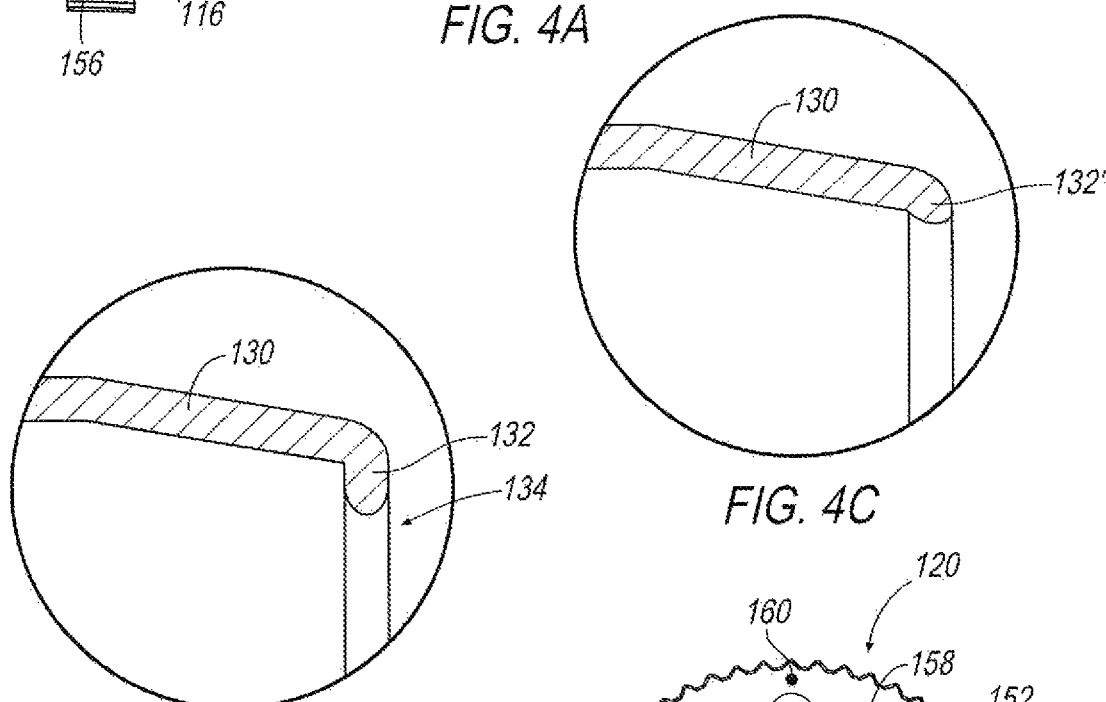
FIG. 4C
FIG. 4B
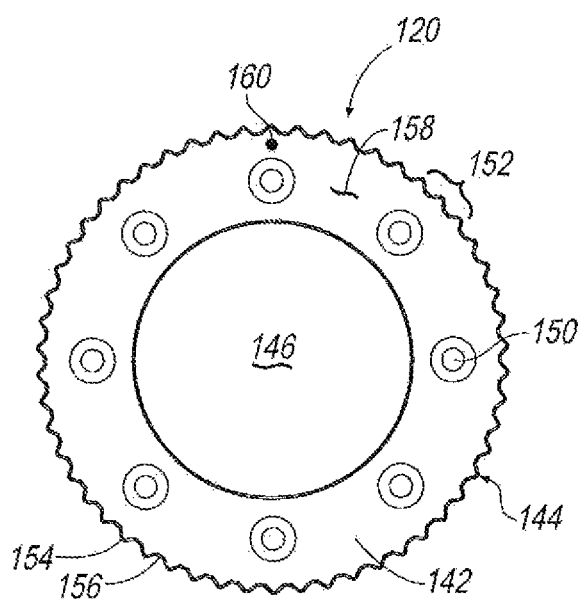
FIG. 5

SURGICAL ACCESS ASSEMBLY AND METHOD OF USING SAME

CROSS-REFERENCE TO RELATED APPLICATIONS

This application is a continuation of U.S. patent application ser. No. 14/847,863 filed Sep. 8, 2015, now U.S. Pat. No. 10,143,366 issued Dec. 4, 2018, which is a divisional application of U.S. patent application Ser. No. 13/786,186, filed on Mar. 5, 2013, now U.S. Pat. No. 9,161,820, issued Oct. 20, 2015, which is a continuation-in-part application of U.S. patent application Ser. No. 13/280,015, filed on Oct. 24, 2011, now U.S. Pat. No. 9,770,261 issued Sep. 26, 2017, which application is a continuation-in-part application of U.S. patent application Ser. No. 11/665,666, filed on Apr. 18, 2007, which application is the U.S. National Phase of PCT/US05/39185 filed Oct. 28, 2005, which claims priority to U.S. provisional application Ser. No. 60/623,094, filed Oct. 28, 2004, the contents of which are incorporated by reference in their entirety.

TECHNICAL FIELD

The present disclosure relates generally to a surgical device for use with delicate and critical tissues, as well as methods of accessing and performing surgery using same.

BACKGROUND

Diagnosis and treatment of conditions affecting the brain are among the most difficult and complex problems that face the medical profession. The brain is a complex and delicate soft multi-component tissue structure that controls bodily functions through a complex neural network connected to the rest of the body through the spinal cord. The brain and spinal cord are contained within and protected by significant bony structures, e.g., the skull and the spine. Given the difficulty of accessing the brain through the hard bony protective skull and the delicate network and complex interactions that form the neural communication network contained within the brain that define the human body's ability to carry on its functions of speech, sight, hearing, functional mobility, reasoning, emotions, respiration and other metabolic functions, the diagnosis and treatment of brain disorders presents unique challenges not encountered elsewhere in the body.

For example, abnormalities such as intracranial cerebral hematomas (ICH), abscesses, Glioblastomas (GB) and metastases (mets) manifest themselves in the intraparenchymal subcortical space (i.e., the white matter) of the brain are particularly challenging to access, let alone treat. The ventricles of the brain contain eloquent communication structures (neural network) which are located in the subcortical space, called fiber tracts and fascicles. Thus, traditionally, unless the ICH, GB, and/or mets where considered anything but "superficial," such conditions have been considered inoperable, simply because getting to the abnormality ICH, GB and/or mets are considered just as damaging as letting the condition take its course. Similarly, tissue abnormalities such as tumors, cysts and fibrous membrane growths which manifest within the intraventricular space of the brain are considered challenging to safely access and often inoperable, due to their locations within the brain.

In order to assist in diagnosis and subsequent treatment of brain disorders, clear, accurate imaging of brain tissue through the skull is required. In recent years significant advances have been made in imaging technology, including stereotactic X-ray imaging, Computerized Axial Tomography (CAT), Computerized Tomographic Angiography (CTA), Position Emission Tomography (PET) and Magnetic Resonance Imaging (MRI), Diffusion Tensor Imaging (DTI) and Navigation systems (instrument position tracking systems). These imaging devices and techniques permit the surgeon to observe conditions within the brain in a non-invasive manner without opening the skull, as well as provide a map of critical structures surrounding an area of interest, including structures such as blood vessels, membranes, tumor margins, cranial nerves, including fiber tracts and fascicles. If an abnormality is identified through the use of one or more imaging modalities and/or techniques, it may be necessary or desirable to biopsy or remove the abnormality.

Once a course of action has been determined based upon one or more imaging techniques, a surgical treatment may be necessary or desired. In order to operate surgically on the brain, access must be obtained through the skull and delicate brain tissue containing blood vessels and nerves that can be adversely affected by even slight disturbances. Therefore, great care must be taken in operating on the brain so as not to disturb delicate blood vessels and nerves to prevent adverse consequences resulting from a surgical intervention.

Traditionally, accessing abnormalities which manifest in deeper spaces within the brain has meant a need for a surgery that creates a highly invasive approach. In some instances, in order to obtain access to target tissue, a substantial portion of the skull is removed and entire sections of the brain are retracted to obtain access. For example, surgical brain retractors are used to pull apart or spread delicate brain tissue, which can leave pressure marks from lateral edges of the retractor. In some instances, a complication known as "retraction injury" may occur due to use of brain retractors. Of course, such techniques are not appropriate for all situations, and not all patients are able to tolerate and recover from such invasive techniques.

It is also known to access certain portions of the brain by creating a burr hole craniotomy, but only limited surgical techniques may be performed through such smaller openings. In addition, some techniques have been developed to enter through the nasal passages, opening an access hole through the occipital bone to remove tumors located, for example, in the area of the pituitary. These approaches are referred to as Expanded Endonasal Approaches (EEA) and were pioneered by one of the inventors of this disclosure.

A significant advance in brain surgery is stereotactic surgery involving a stereotactic frame correlated to stereotactic X-ray images to guide a navigational system probe or other surgical instrument through an opening formed in the skull through brain tissue to a target lesion or other body. A related advance is frameless image guidance, in which an image of the surgical instrument is superimposed on a pre-operative image to demonstrate the location of the instrument to the surgeon and trajectory of further movement of the probe or instrument.

In recent years, surgical access systems have been developed to provide access to previously difficult to access areas. One such prior art system is shown in FIGS. 1A-1C. System 10 includes a retractor 20 and an introducer 40. Introducer 40 includes a cone-shaped distal end 42 with an opening 52 therein (best seen in FIG. 1C). The cone-shaped distal end is configured to be a generally blunt, flat surface. With introducer 40 positioned within retractor 10, system 10 is inserted into brain tissue, thereby pushing brain tissue away while providing access to an area of interest. Once system 10 is delivered to the area of interest, retractor 10 is rigidly fixed in position. More specifically, retractor 10 is fixed in space with the use of a standard or conventional neurosurgical fixation device. Once, retractor 10 is fixed in place, introducer 40 is then removed from retractor 10, while leaving retractor 10 in its fixed place, thereby creating a pathway through the brain tissue.

While access system 10 may provide a manner to access certain brain tissue, the blunt shaped distal end of can actually cause transient or even permanent deformation and trauma of delicate tissue structures which can manifest itself in temporary or permanent neurological deficits after surgical intervention due to damage of blood vessels, cranial nerves, fiber tracts and fascicles. Opening 52 may cause scoring of tissue, also leading to damage of the tissues and structures as introducer 40 is pushed through tissue. Further, by rigidly fixing the placement of retractor 10, manipulation of retractor 10 is impeded and requires constant attention by loosening and retightening to re-position for even micro-movement of the retractor 10, thereby lengthening procedure time.

Another issue that needs to be addressed is visibility. Typically when employing an access system in a surgical procedure, it is often like operating in a poorly lit tunnel. To provide illumination, it is known to place a light source within the introducer sheath, such as an endoscope. However, when using an endoscope, the light source takes up a significant amount of working space within the introducer sheath, thus reducing the functional working area for other instruments, as well as minimizing the ability to move other instruments within the surgical site.

Alternatively, light must be delivered from a remote or external location, such as a microscope or exoscope. However, in the case of microscopes and exoscopes, the external light source is often blocked by the surgeon and/or instruments in the surgical field. At a minimum, the effectiveness is greatly diminished at the distal end of the introducer sheath where the actual surgical work and/or treatment is occurring, and where effective visualization is needed the most.

Notwithstanding the foregoing advances in imaging technology and both frame and frameless stereotactic image guidance techniques, there remains a need for improved surgical techniques and apparatus for operating on brain tissue, including providing improved visibility, while minimizing surgical openings.

BRIEF DESCRIPTION OF THE DRAWINGS

Exemplary embodiments of the present disclosure will now be described in greater detail with reference to the attached figures, in which:

FIG. 4A is a side elevational view of the outer sheath of FIG. 3.

FIG. 4B is an enlarged cross-sectional view of a portion of the distal end of the outer sheath of FIG. 4A.

FIG. 4C is an enlarged cross-sectional view of a portion of an alternative embodiment of the distal end of the outer sheath of FIG. 4A.

FIG. 5 is an end view of outer sheath of FIG. 3.

DETAILED DESCRIPTION

Figure 1A:
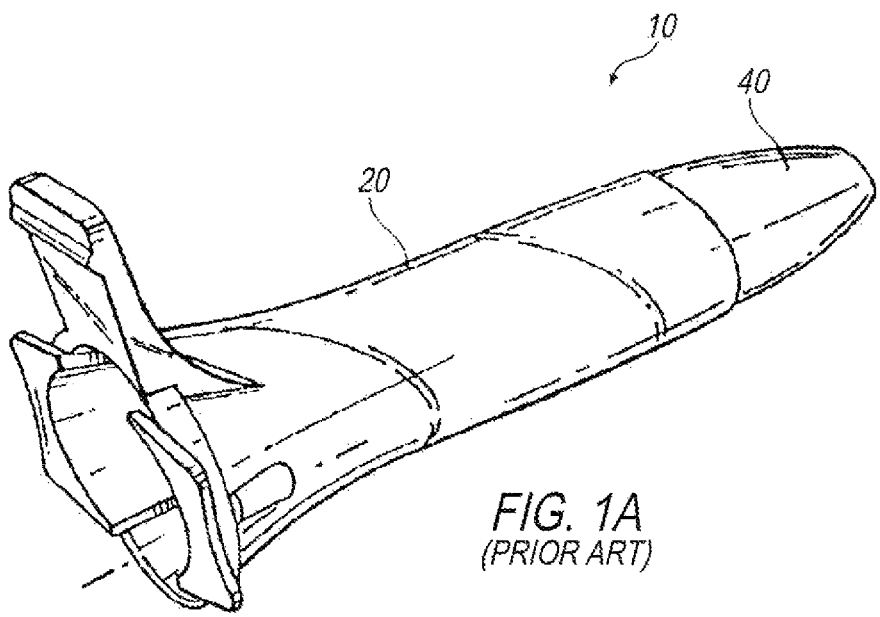
FIGS. 1A-1C illustrate a prior art surgical access system.
Figure 1B:
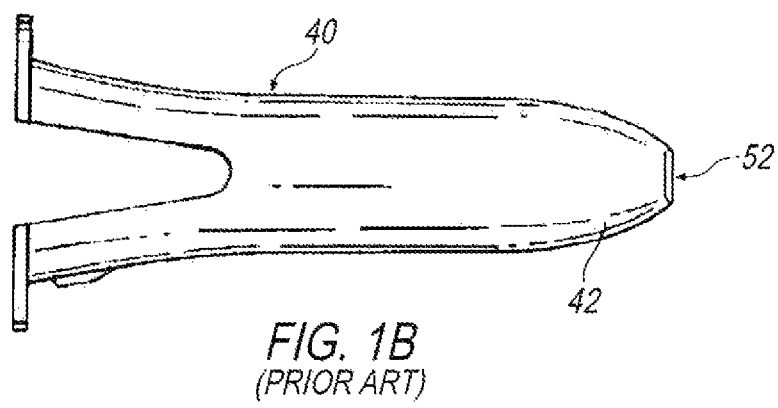

Referring now to the discussion that follows and also to the drawings, illustrative approaches to the disclosed assemblies and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is surgical access assembly, various components for use in same, and a method of using the surgical access assembly. The components disclosed herein provide surgeons with an enhanced ability to minimize trauma to the patient, while providing efficient improved minimally invasive surgical techniques, such as, for example, during intracranial surgical techniques.

Figure 2:
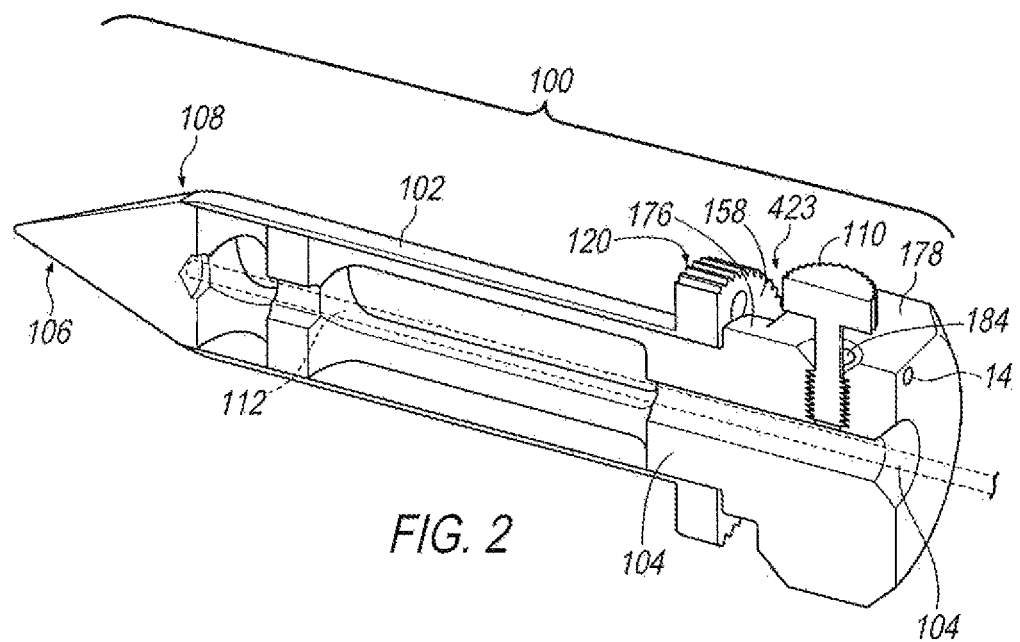
FIG. 2 is a perspective cross-sectional view of an exemplary arrangement of a surgical access assembly.

Referring to FIG. 2, a perspective cross-sectional view of a surgical access assembly 100 is shown. In one exemplary arrangement, surgical access assembly 100 comprises a hollow outer sheath 102 and a selectively removable obturator 104. As best seen in FIG. 2, obturator 104 is configured with a length that is longer than a length of outer sheath 102 such that a distal end 106 of obturator 104 protrudes a predetermined distance from a distal end 108 outer sheath 102, as will be discussed below in greater detail.

A locking member 110 may also be provided. Locking member 100 is configured to operatively retain a separate navigation member 112 (shown in phantom) within obturator 104, as will be discussed in greater detail below. A retaining member 114 may be secured within a portion of obturator 104 to prevent locking member 110 from being completely disengaged from obturator 104.

Figure 3:
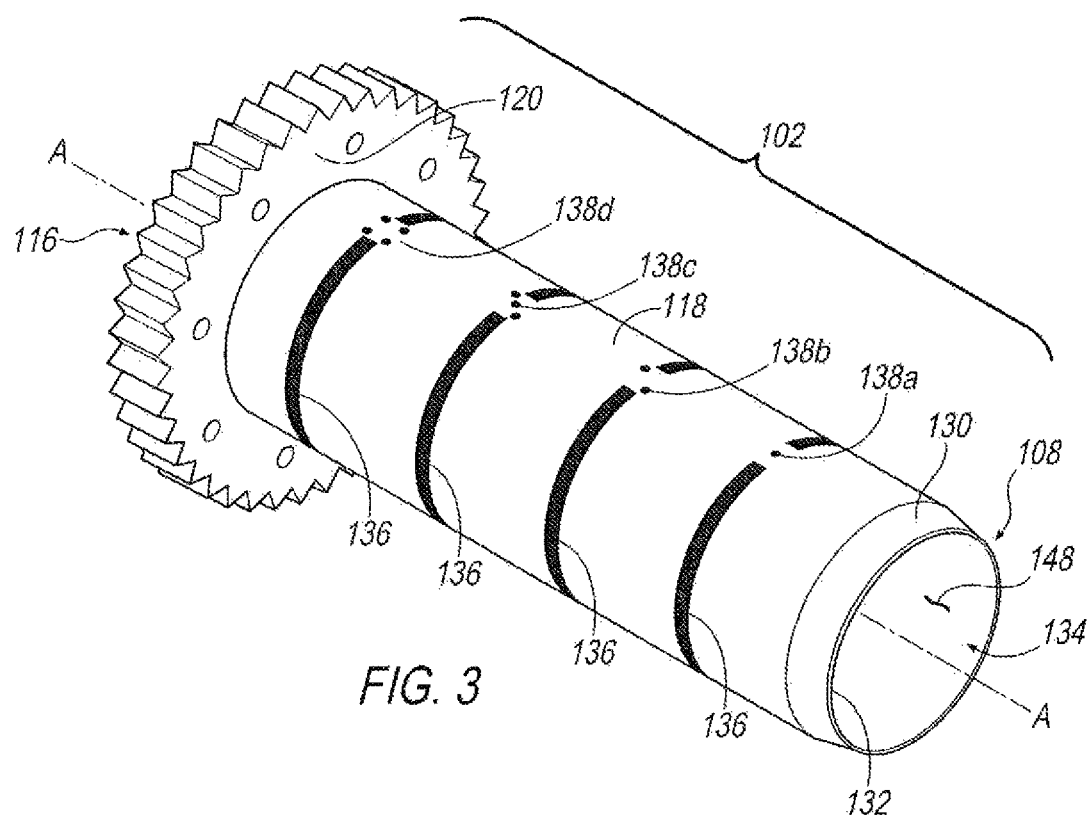
FIG. 3 is a perspective view of an outer sheath of the surgical access assembly of FIG. 2.

Referring now to FIGS. 3-5, outer sheath 102 will be described in greater detail. Outer sheath 102 is defined by distal end 108 and a proximal end 116 and includes a generally hollow body portion 118 and a grip ring 120. In one exemplary arrangement, grip portion 120 is configured as a ring, as illustrated in the drawings. However, it is understood that grip portion 120 need not be configured as a ring. For ease of explanation, grip portion 120 will be referred to hereinafter as grip ring 120. Grip ring 120 is fixedly secured to body portion 118 at proximal end 116. In one exemplary arrangement, body portion 118 is constructed of a clear biocompatible material that permits viewing of normal tissue, abnormal tissue, as well as critical structures that are disposed outside of body portion 118 when outer sheath 102 is disposed within such tissue. In one exemplary arrangement, outer sheath 102 is constructed of polycarbonate, though other biocompatible materials may be employed, including resins.

In one exemplary configuration, an imaging mechanism may be incorporated into outer sheath 102 that would permit visualization of tumors, vessels, fiber tracks, fascicles and even healthy tissue, in real-time. Indeed, as will be explained in further detail below, the imaging mechanism will enable physiological functional imaging to provide information about the characteristics of the cortical fiber tracks to be visible, thereby enabling a user to separate and park such fibers on either side of outer sheath 102 rather than cutting, stretching and potentially damaging such fibers while gaining access to a desired location within the brain. Further, as will be explained in further detail below, the imaging mechanism may also enable the surgeon to have real-time information about the fiber tract and fascicle location, after placement of outer sheath 104, and during abnormality resection procedure therethrough. In addition to white matter tract imaging, mapping of the characteristics of the cerebral blood flow may be obtained.

In one exemplary embodiment, the imaging mechanism may be an ultrasound probe incorporated into outer sheath 102. For example, outer sheath 102 may be provided with one or more channels within the wall that defines outer sheath 102 that are configured with one or more small diameter ultrasound probes. In another arrangement, a single ultrasound probe that is configured to be received within outer sheath 102 may be provided. In yet another embodiment, a low field MRI probe may be selectively placed in outer sheath 102 to provide enhanced imaging. In yet another embodiment a low field MRI imaging coil may be molded into or bonded into outer sheath 102. In still another exemplary arrangement, the probe may be an optical coherent tomography (OCT) imaging or spectroscopy.

Distal end 108 of outer sheath 102 may be configured with a tapered portion 130 that extends towards a center axis A-A of outer sheath 102 to a distal edge 132 that surrounds an opening 134 in distal end 108 of outer sheath 102. Tapered portion 130 serves to ease the transition between outer sheath 102 and a distal tip portion 172, without drag, trauma or coring of tissue from a diameter that defines a body portion 168 of obturator 104 to a diameter that defines body portion 118 of outer sheath 102. In one exemplary configuration, distal end 108 may be configured with a radius or other configuration so as to create a smooth/atraumatic transition of the brain tissue when surgical access assembly 100 is inserted into the brain.

Figure 1C:
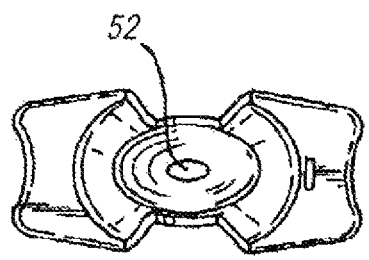

For example, as best seen in FIG. 4B, distal edge 132 is configured so as to be non-sharpened and radiused. In one exemplary arrangement, distal edge 132 is configured as a 0.3 mm diameter radiused rim. Tapered portion 130 and radiused distal tip 132 cooperates with obturator 104 to atraumatically move tissue, as well as various structures within the brain, including white matter, away from outer sheath 102 without cutting tissue or such structures. Indeed, unlike prior art devices that include either a blunt tip distal end or a tapered leading edge such as that shown in FIG. 1C, radiused distal tip 132 cooperates with tapered portion 130 and obturator 104 to prevent bruising and damage to various tissue. More specifically, this configuration facilitates entry of outer sheath 102 into delicate tissue, but without cutting such delicate tissue. Insertion of surgical access assembly 100 will be explained in further detail below.

Body portion 118 may further be provided with a plurality of spaced apart indicators 136. Indicators 136 generally extend about the circumference of body portion 118 and each may further incorporate a secondary indicator 138 that visually illustrates a predetermined location on body portion 118, as shown in FIG. 3. While FIG. 3 illustrates four indicators 136, it is understood that body portion 118 may be provided in a variety of lengths and that any number of indicators 136 may be provided. Body portion 118 may also be provided with a longitudinal indicator 140. More specifically, as best seen in FIG. 4A, longitudinal indicator 140 extends from proximal end 116 to distal end 108. Indicators 136, 138 and 140 may be printed onto either an internal or external surface of body portion 118 with an imaging visible ink such as, for example ink containing fluro-deoxyglucose (FDG), Technicium 99, Gadolinium, titanium dust, barium sulfate, a combination of the above or other suitable imaging material. Indicators 136 and 138 provide a reference point for the operator of system 100, as structures may be visible through body portion 118. Indicator 136, 138 and 140 may also be configured to be visible under MRI, CT, PET, or any other suitable imaging modality to enable easy identification of areas of interest. In one alternative embodiment, indicators 136, 138 and/or 140 may be etched or printed onto body portion 118, either on the internal or external surface of body portion 118.

Details of grip ring 120 are best seen in FIG. 5. Grip ring 120 is generally configured as a flange member 142 defined by an outer periphery 144 and an inner opening 146. Inner opening 146 may be sized to generally correspond to the diameter of a lumen 148 defined by body portion 118. Outer periphery 144 is sized to have a diameter that is larger than lumen 148 of body portion 118. Flange member 142 may further be provided with one or more small openings 150 that are disposed therein. In one exemplary arrangement, a plurality of small openings 150 are provided that are spaced generally equi-distantly about inner opening 146. Small openings 150 will be described in further detail below. Outer periphery 144 may further be provided with a textured surface 152 to provide for ease of gripping outer sheath 102. For example, in one exemplary arrangement, textured surface 152 comprises a plurality of alternating ridges 154 and grooves 156. However, it is understood that other textured surfaces may be employed.

Disposed on a proximal end surface 158 of flange member 142, an alignment feature 160 may be employed. Alignment feature 160 is used to indicate the location of longitudinal indicator 140 when outer sheath 102 is positioned within the brain. Alignment feature 160 will be discussed below in greater detail.

Figure 6A:
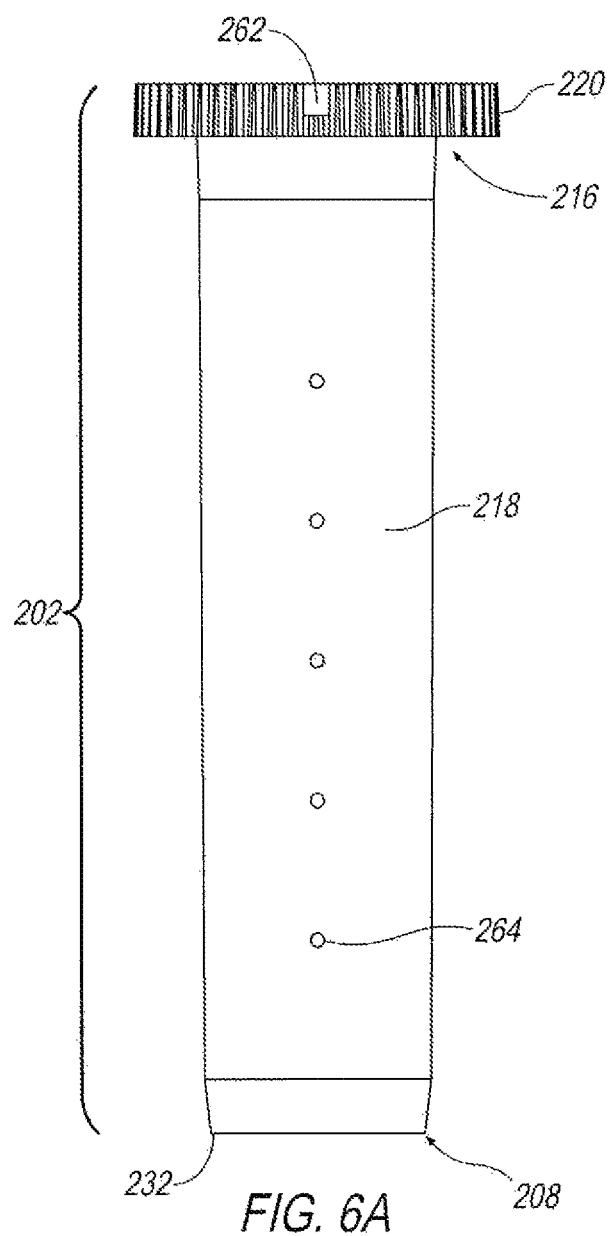
FIG. 6A is an elevational view of an alternative embodiment of an outer sheath.
Figure 6B:
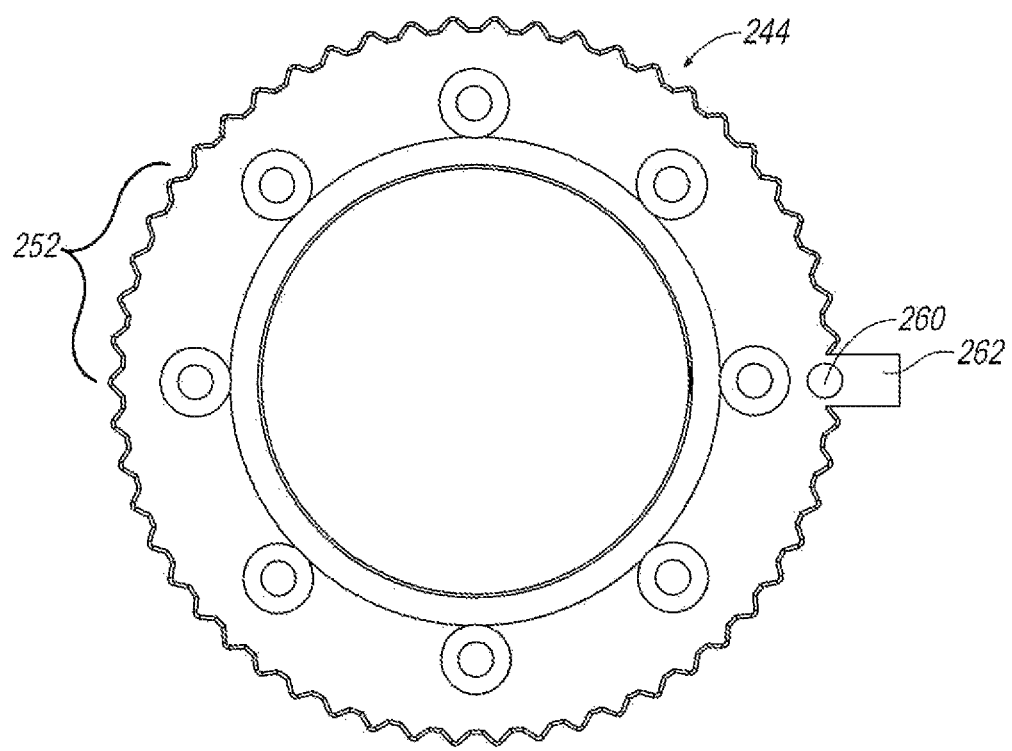
FIG. 6B is an end view of the outer sheath of FIG. 6A.

An alternative embodiment of outer sheath 202 is shown in FIGS. 6A-6B. Outer sheath 202 is similar to outer sheath 102 in that it is defined by a distal end 208, a proximal end 216 and a body portion 218. A distal edge 232 is generally configured to be similar as distal tip 132. A grip ring 220 is fixedly secured to body portion 218.

Figure 11A:
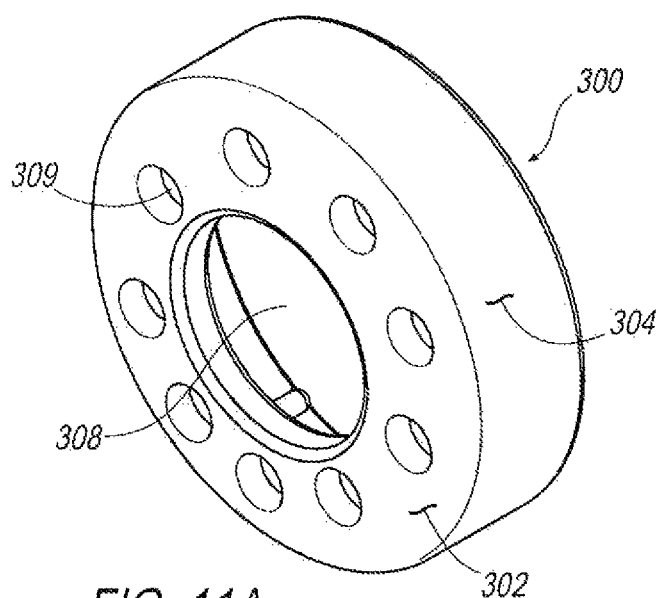
FIG. 11A is a perspective view of an illuminating ring that operatively connects to an outer sheath of the surgical access assembly.
Figure 11B:
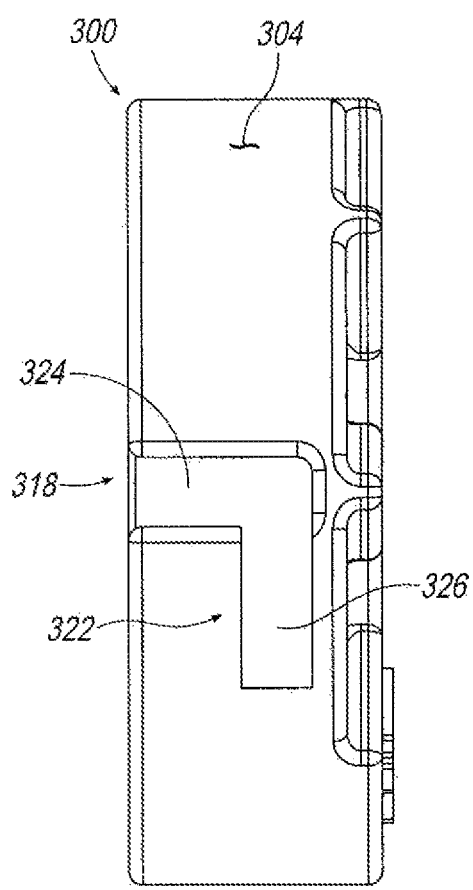
FIG. 11B is a side view of the illuminating ring of FIG. 11A.
Figure 11C:
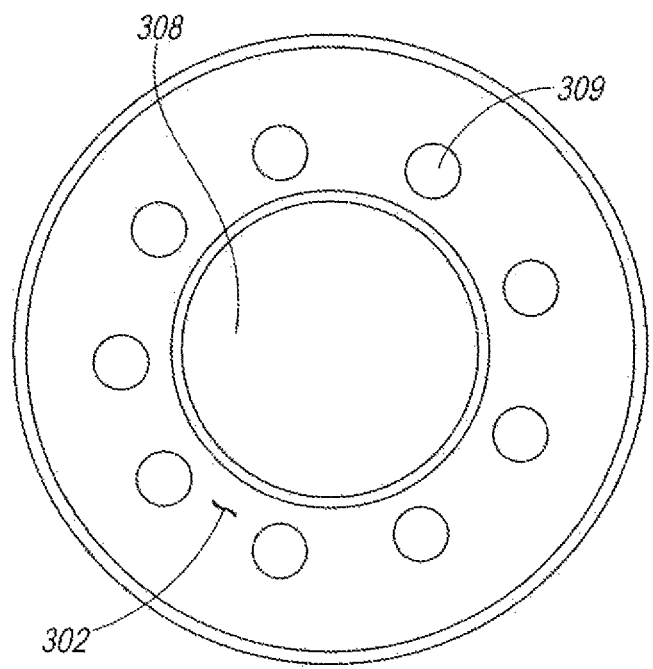
FIG. 11C is a top view of the illuminating ring of FIG. 11A.
Figure 11D:
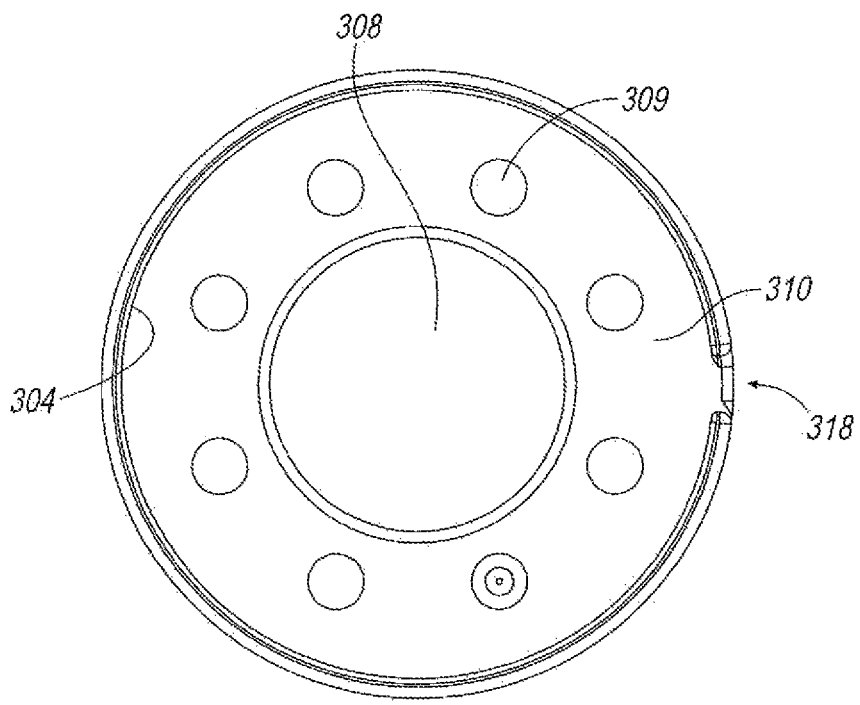
FIG. 11D is a bottom plan view of the illuminating ring of FIG. 11A.
Figure 11E:
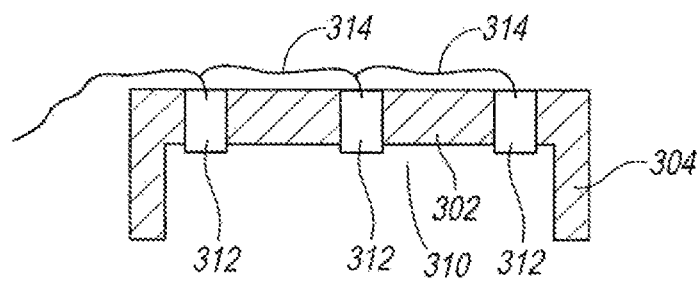
FIG. 11E is a cross-sectional view of an exemplary arrangement of a lighting arrangement for the illuminating of FIG. 11A.
Figure 11F:
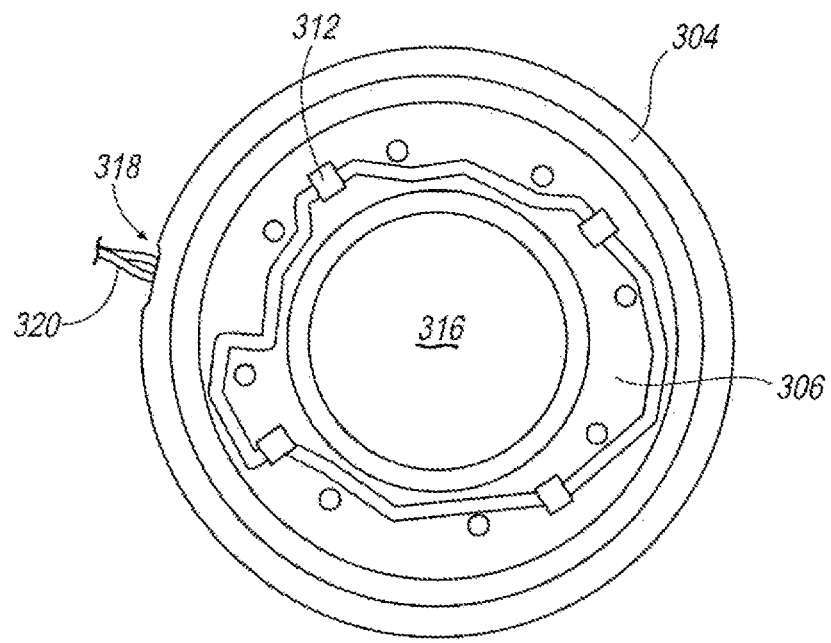
FIG. 11F is a plan view of a circuit board for use with the illuminating ring of 11A.

Grip ring 220 also includes a textured surface 252. Grip ring 220 further includes a locating member 262. Locating member 262 is configured to operatively connect an illumination ring (best seen in FIG. 11A) 300 to outer sheath 102. As may be seen, in one exemplary configuration, locating member 262 extends outwardly from outer periphery 244 of grip ring 220. Locating member 262 may also serve as an alignment feature for indicating the location of longitudinal indicator 240. Alternatively, a separate alignment feature 260 may be provided. For example, in FIG. 6B, alignment feature 260 is positioned adjacent locating member 262.

Body portion 218 may also be provided with indicators 34, 36, and 38 to assist in locating outer sheath 202 in operation. However, in another alternative arrangement, body portion 218 may be provided with indicators 264 that produce a signal void or minimal artifact under certain imaging modalities. In one specific arrangement, indicators 264 may be configured as small holes that are spaced apart at predetermined distances, as shown in FIG. 6A. In yet another alternative arrangement, indicators 264 may be configured as non-through divots. In still a further alternative arrangement, indicators 264 may be configured as a longitudinal groove (not shown) on either the internal or external surface of body portion 218.

Referring to FIGS. 7-10, obturator 104 will now be described. Obturator 104 is defined by distal end 106, a proximal end 166, a body portion 168 and a handle portion 170. Distal end 106 is configured with a generally conical shaped distal tip portion 172 that tapers to a tip member 174 to provide atraumatic dilation of tissue. In one exemplary arrangement, tip portion 172 tapers toward a closed tip member 174 so as to prevent coring of tissue as obturator 104 is inserted into the brain.

There are a number of variables that play the selection of the angle α that defines the taper of tip portion 172. These variables include the size of an outer diameter D1 of obturator 104, the desired length that distal tip portion 172 extends from body portion 168, and the desired offset for a distal tip of navigation member 112 and tip member 174. More specifically, it is contemplated that surgical access assembly 100 will be provided as part of a kit that may include multiple sized outer sheaths 102 and obturators 104, to provide the surgeon with a choice of different diameter sizes and lengths so as to provide flexibility for accessing areas of interest within the brain. However, to insure that the distal tip 174 is determinable regardless of which size diameter D1 of obturator 104 is used, taper angle α may be selectively adjusted. For embodiments that utilize navigation member 112 that positions a distal end thereof at a set position within obturator 104 (as will be explained in further detail below), to maintain an identical offset length between the distal end of navigation member 112 and distal tip 174 in different diameter D1 sized obturators 104, taper angle α will need to be increased, as diameter D1 increases.

For example, if diameter D1 of obturator 104 is 13.5 mm, an exemplary angle α may be 45.5° to provide effective atraumatic dilation, as well as a determinable distal tip 174 location. However, if diameter D1 of obturator 104 is 15.5 mm, an exemplary angle α' may be 52.8°.

Figure 8A:
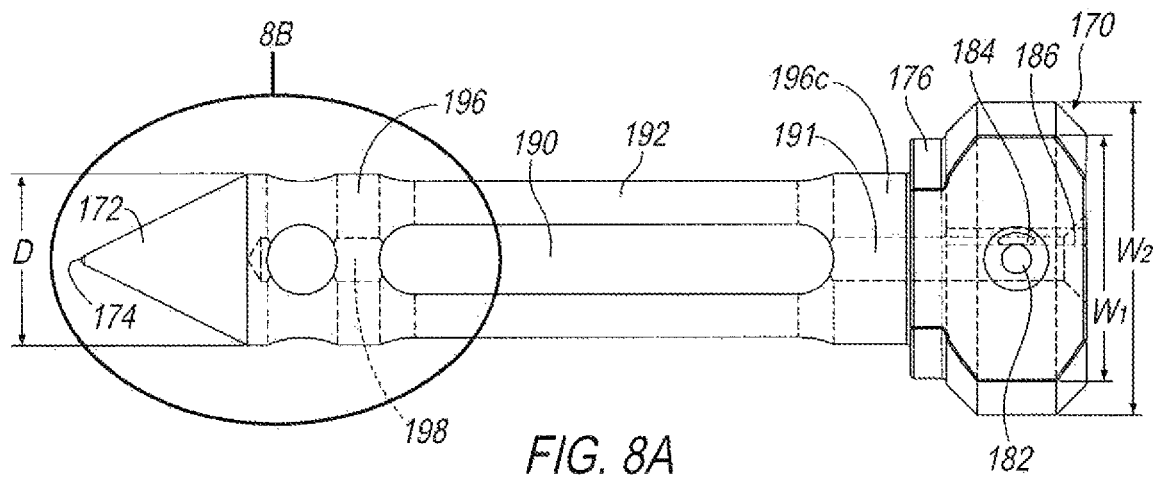
FIG. 8A is a top view of the obturator assembly of FIG. 7A.
Figure 8B:
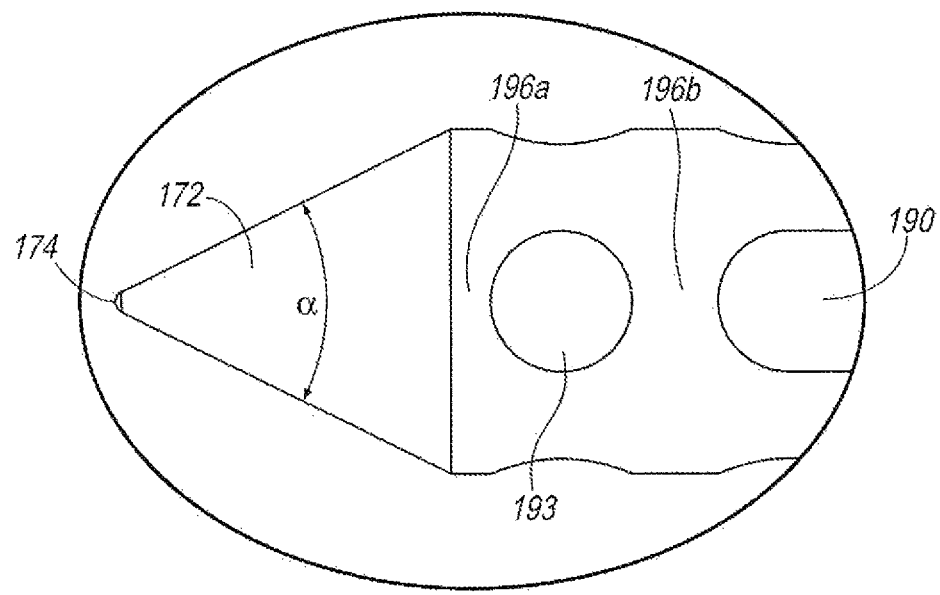
FIG. 8B is an enlarged view of a distal end of the obturator assembly taken from area 8B of FIG. 8A.
Figure 8C:
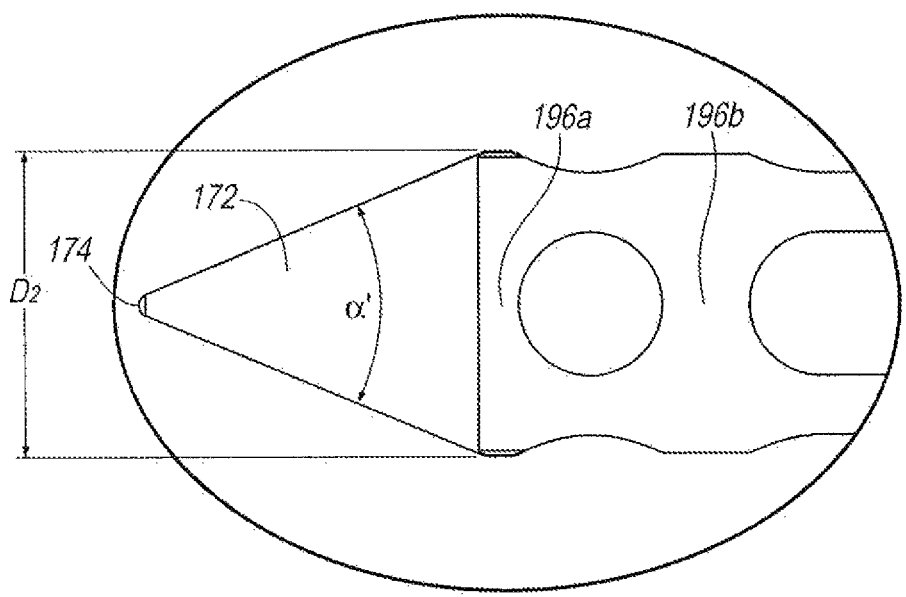
FIG. 8C is an alternative embodiment of the distal end of the obturator assembly taken from area 8B of FIG. 8A.

As best seen in FIG. 8B, distal tip 174 is configured to be radiused such that tip member 174 is rounded, and neither blunt, nor sharp. More specifically, tip member 174 is configured so as not to have any flat portions which during insertion can stretch or even tear the delicate tissues such as the vessels, fiber tracts and fascicles found in the brain. Further, because tip member 174 is closed, damage of such delicate tissues and fascicles are also avoided. In one exemplary embodiment, tip member 174 is configured with a 0.5 mm radius. As will be explained in further detail below, the configuration of tip member 174 is designed to gently displace and move the tissue into which it is inserted; i.e., atraumatically dilate the tissue to allow for introduction in to an intra-fascilar and para-fascilar manner, as opposed to cutting tissue as surgical access assembly 100 is inserted into the tissue.

Figure 9A:
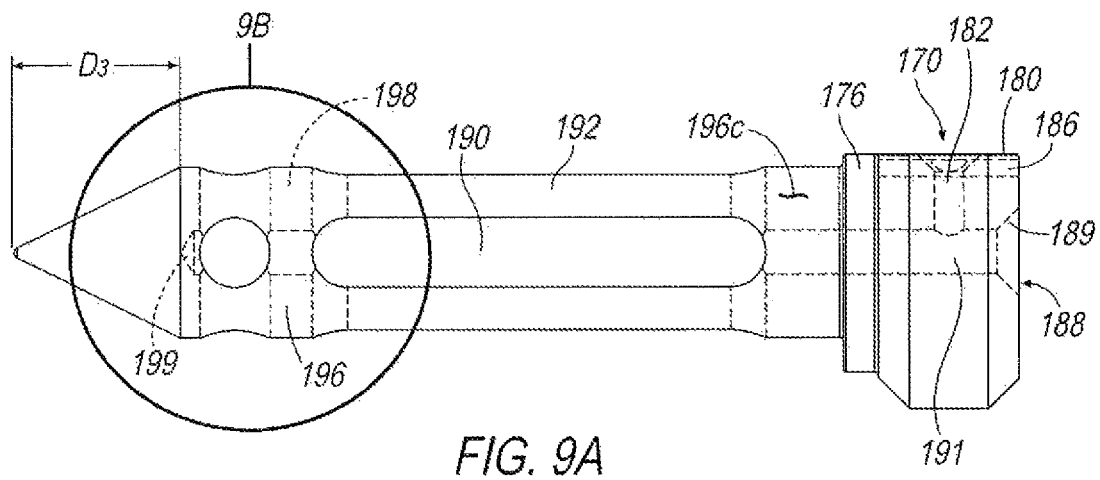
FIG. 9A is a side elevational view of the obturator assembly of FIG. 7A.

Handle portion 170 is positioned at proximal end 166 of obturator 104. As best seen in FIGS. 7B, 8A and 9A, handle portion 170 comprises a stop member 176 and a grip member 178. Stop member 176 is positioned distally of grip member 178 and, as best seen in FIG. 8A, is configured to have a width W1 that is greater than a diameter D1 of body portion 168, as well as a diameter D2 of outer sheath 102 (shown in FIG. 4A). Grip member 178 is configured with a width W2 that is greater than the width W1 of stop member 176, thereby providing a step-like configuration. Stop member 176 further defines an engagement surface 177 that is axially spaced from a distal surface 179 of grip member 178.

Figure 7A:
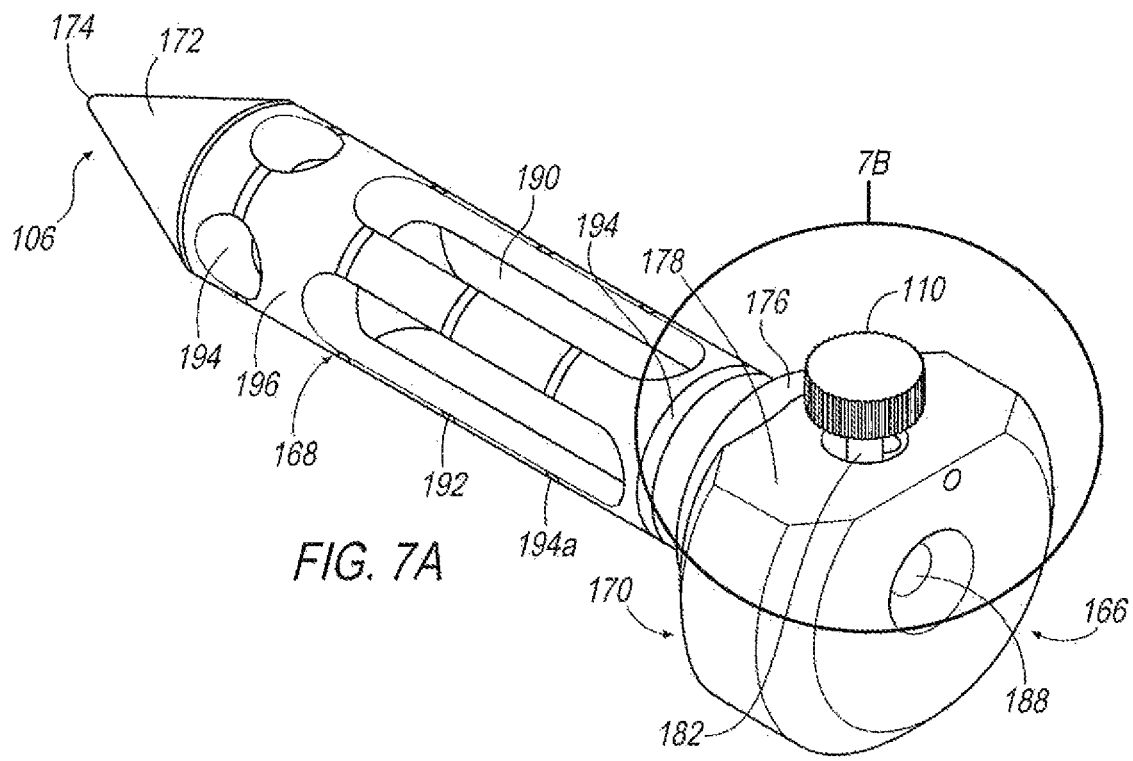
FIG. 7A is a perspective view of an obturator assembly of the surgical access assembly of FIG. 2.
Figure 7B:
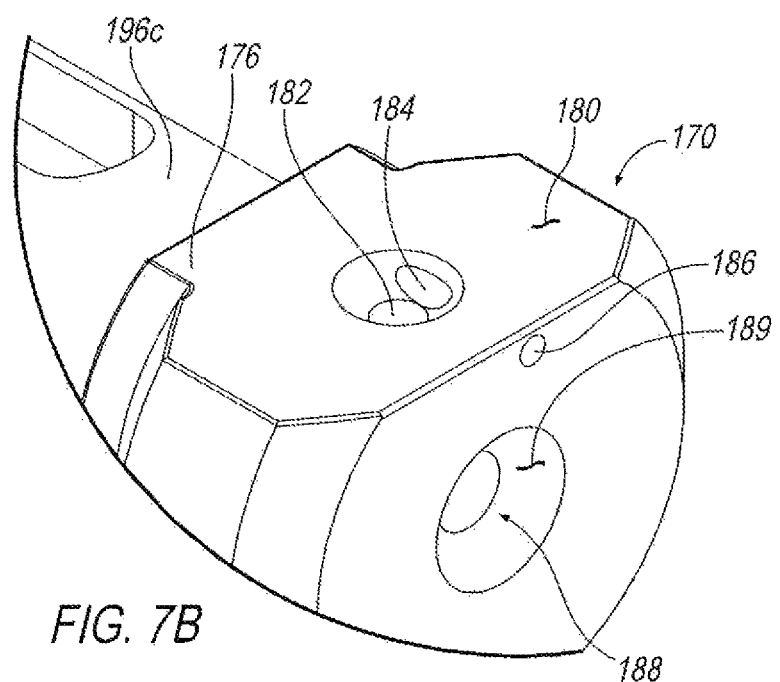
FIG. 7B is an enlarged view of an end face of the obturator assembly taken from area 7B of FIG. 7A.
Figure 10:
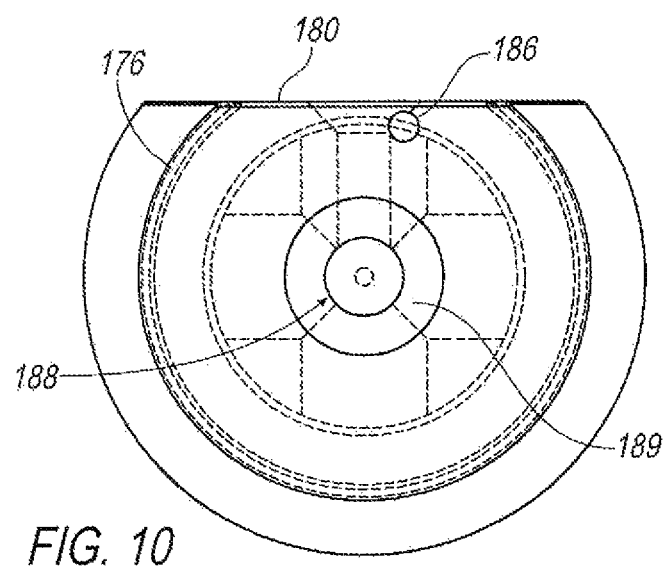
FIG. 10 is an end view of the obturator assembly of FIG. 7A.

In one exemplary arrangement, handle portion 170 is configured with a generally planar surface 180, as best seen in FIGS. 7A-7B and FIG. 10. Planar surface 180 is configured with a receiving aperture 182 that is configured to receive locking member 110. In one exemplary arrangement, receiving aperture 182 is threaded. As best seen in FIGS. 2, 7B, and 8A, disposed within receiving aperture 182 is an engagement opening 184. Engagement opening 184 is in communication with a channel 186 (seen in phantom in FIGS. 8A and 9A) that extends at least partially thorough handle portion 170. After locking member 110 is at least partially engaged within receiving aperture 182, retaining member 114 (FIG. 2) is positioned within channel 186. Because engagement opening 184 opens into receiving aperture 182, a portion of retaining member 114 extends across a portion of receiving aperture 182 such that locking member 110 is prevented from being entirely withdrawn from receiving aperture 182. For example, locking member 110 is illustrated as having threads that cooperate with corresponding internal threads in receiving aperture 182. Retaining member 114 is positioned within channel 186 so as to extend above the threads of locking member 110 such as locking member 110 is being removed from receiving aperture 182, threads come into contact retaining member 114, thereby preventing complete removal of locking member 110 from handle portion 170.

An access opening 188 is formed through proximal end 166. Access opening 188 extends through handle portion 170. In one exemplary arrangement, access opening 188 may be provided with an inwardly extending chamfer 189 that tapers toward access opening 188. Chamfer 189 provides a self-directing feature for inserting navigation member 112 into access opening 188. Access opening 188 is in communication with a first channel segment 191 that extends through handle portion 170 and into body portion 168.

Figure 8D:
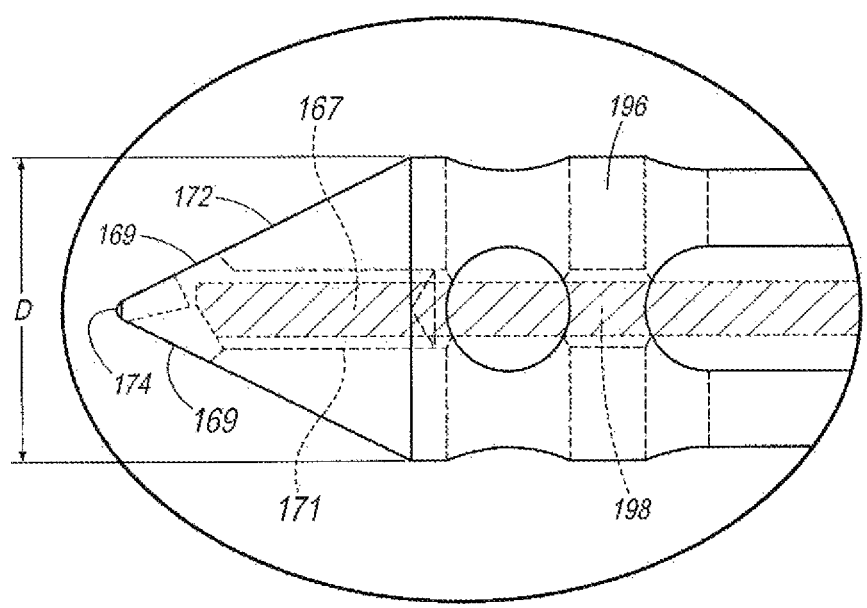
FIG. 8D is an alternative embodiment of the distal end of the obturator assembly taken from area 8B of FIG. 8A.

As seen in FIG. 8D, obturator 104 may further be configured to receive a viewing member 167 operatively connected thereto. More specifically, conical tip portion 172 may be configured with one or more viewing windows 169 that are oriented to be flush with the surface of conical tip portion 172. Viewing windows 169 are in communication with a viewing member channel 171 that may selectively receive a viewing member such as, for example, a fiber optic cable or an ultrasound probe. The viewing member may be in addition to the use of navigation member, or in place thereof. The viewing member permits the surgeon to observe, in real-time (i.e., during insertion), surrounding tissue and eloquent tissue structures so as to minimize trauma during insertion.

Body portion 168 extends between distal end 106 and proximal end 166. Body portion 168 includes one or more elongated void areas 190. Void areas 190 serve to reduce weight of obturator 104, thereby making obturator 104 easier to manipulate during surgical procedures. Void areas 190 also facilitate sterilization of obturator 104 by moisture retention within body portion 168 of obturator 104. Further, void areas 190 also provide venting, thereby preventing a vacuum from being generated as obturator 104 is being withdrawn from outer sheath 102 during operation.

Void areas 190 are separated by web portions 192 that extend axially through a portion of the length of body portion 168. Disposed on web portions 192 of body portion 168 are one or more indicators 194. Indicators 194 may include spaced apart hash marks (designated as 194A) that cooperate with an imaging modality to provide information, in real-time, concerning the location of obturator 104 relative to various tissue, critical structures, and fascicles within the brain, while obturator 104 is positioned within tissue. Indicators 194 also assist with providing information to regarding the relative positions between obturator 104 and outer sheath 102. Indicators 194 produce a signal void or minimal artifact under certain imaging modalities.

Body portion 168 may further include one or more cross webs 196. Cross webs 196 are oriented transverse to web portions 192 and connect web portions 192 together. In one exemplary arrangement, body portion 168 includes at least one cross web 196 that operatively defines the outer diameter D2 of body portion 168. Diameter D2 is sized to fit within lumen 148 of outer sheath 102 such that obturator 104 and outer sheath 102 may be selectively slid relative to one another. However, diameter D2 is also sized to minimize or even eliminate any gaps between an inner surface of outer sheath 102 and an outer surface of obturator 104. In the exemplary arrangement shown in FIG. 7-9, three cross webs 196A, 196B and 196C are provided. A first cross web 196A is connected to distal tip portion 172, while second cross web 196B is spaced proximally from first cross web 196A and separated by a void area 193. Third cross web 196C is separated from second cross web 196B by void areas 192 and is positioned distal from first stop member 176 of handle portion 170. Cross webs 196 serve to provide for structural integrity of obturator 104, as well as improved rigidity.

In one exemplary arrangement, one or more of cross webs 196 may further be provided with an annular compensating protuberance 197 to accommodate for slight manufacturing variations of the diameter of lumen 148 of outer sheath 102. For example, as it is contemplated that outer sheath 102 may be a component that is molded from a resin, a process which may produce such slight manufacturing variations. Compensating protuburance 197 extends slightly radially outwardly from an outer surface of obturator 104 and cooperates with lumen 148 of outer sheath 102 to create a friction fit between the outer surface of obturator 104 and lumen 148, due to the slight flexibility of the resin of outer sheath 102. Use of compensating protuberance 197 thereby reducing the need for maintaining a high dimensional tolerance of outer sheath 102 in production.

Figure 9B:
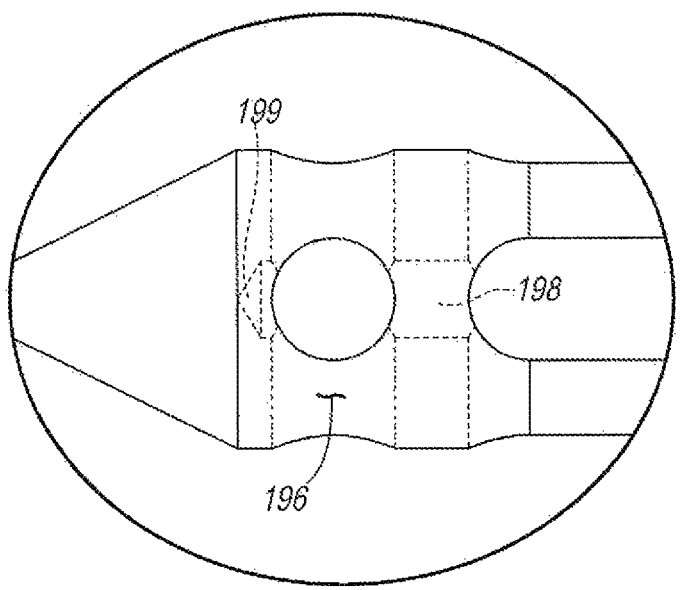
FIG. 9B is an enlarged view of a portion of the obturator assembly taken from area 9B of FIG. 9A.

In one embodiment, cross web 196B is provided with a second channel segment 198 (shown in phantom) that extends there through. Second channel segment 198 is axially aligned with first channel segment 191 and is configured to selectively receive navigation member 112. In one exemplary arrangement, disposed in first cross web 196A is an inwardly extending depression 199, as best seen in FIG. 9B. Depression 199 is configured in such a manner so as to align a distal tip of navigation member 112 with distal end 108 of outer sheath 102, when outer sheath 102 is assembled to obturator 104.

Referring to FIGS. 11A-11F, details of an optional illuminating ring 300 will now be described. Illuminating ring 300 is generally defined by a top surface portion 302, a wall member 304. A circuit board 306 may also be provided. Top surface 302 includes at least one access opening 308 therethrough that is configured to receive one or more surgical instruments, as will be described below in further detail. Additional small openings 309 may be provided in top surface 302. One or more of small openings 309 are configured to be aligned with small openings 150 disposed on flange member 142. Wall member 304 extends from top surface 302 so as to create an open cavity 310 within illuminating ring 300. An outer surface of wall member 304 may be textured (not shown), similar to grip ring 120.

One or more light elements 312 that are supported by a portion of illuminating ring 300. In one embodiment, shown in FIG. 11E, lights 312 are fixedly mounted to top surface 304 so as to face inwardly toward open cavity 310, adjacent access opening 308. Each light 312 is electrically connected to a remote power source (not shown) by wires 314. In one exemplary arrangement, wires 314 may be retained within channels formed in top surface 302 around access opening 308.

In an alternative arrangement (FIG. 11F), lights 312 may be incorporated in a circuit board 306. Circuit board 306 is configured with an access opening 316 that may be aligned with access opening 308 formed in top surface 302. Further, circuit board 306 is also sized to be positioned within open cavity 310, and fixed thereto. In other words, in one arrangement, circuit board 306 is sized to have an outer diameter that is smaller than an inner diameter defined by wall member 304. A wall opening 318 may be formed through a portion of either top surface 302 or wall member 304 to provide access for wires 320 to electrically connect circuit board 306 to a power source. An example of wall opening 318 may be seen in FIGS. 11B, 11D, and 11F. Circuit board 306 may be configured such that there is a constant output of light when illuminating ring 300 is turned on so that there is a steady state.

Figure 11G:
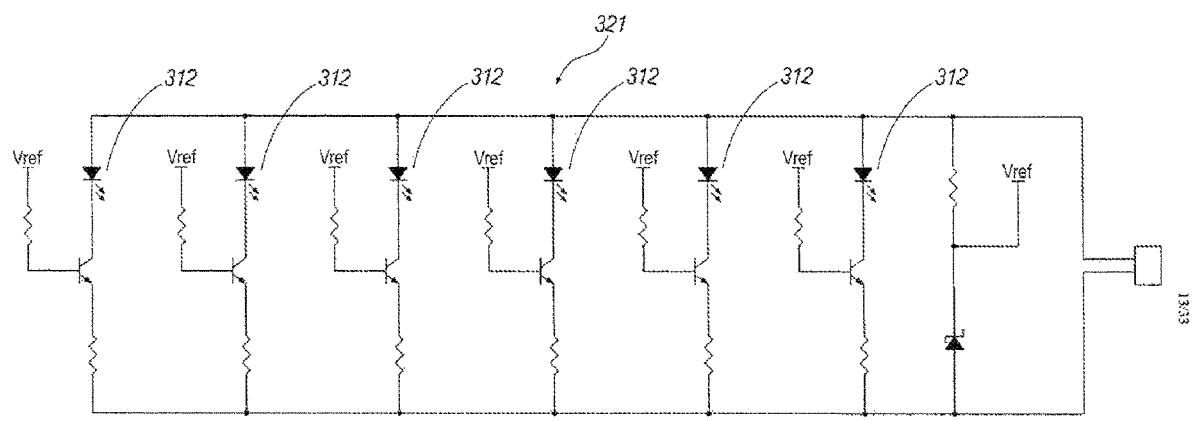
FIG. 11G is an exemplary electrical schematic for use with the illuminating ring of FIG. 11A.

An exemplary circuit design 321 is depicted in FIG. 11G for circuit board 306. In the exemplary configuration, circuit design 321 is configured to prevent flickering of lights 312 and/or prevent operation of less than all of the lights 312 during use of illuminating ring 300. More specifically, circuit design 321 is configured such that if one light 312 burns out, or if batteries that supply power to circuit get low, illuminating ring 300 will simply shut off and a replacement illuminating ring 300 may be used.

In one exemplary arrangement, lights 312 are LED lights, although other light devices may be utilized. LED lights do not contribute significantly to the weight of surgical access assembly 100, and also dissipates a non-clinical significant amount of heat. Moreover, LED lights can emit different combinations of colors/frequencies of light that may be incorporated to illuminating ring 300, to provide improved visualization of fluorescing dyes which allow for the differentiation of tissues.

Use of LED lights also allow for an endoscope to be used with surgical access assembly 100, but without an accompanying fiber-optic light source. This arrangement significantly reduces a required overall outside diameter of the endoscope, which improves the working space within lumen 148 of outer sheath 102. More specifically, lumen 148 of outer sheath 102 has more available working space, thereby providing increased simultaneous use of multiple instrumentation, as well as improved visualization. Further, because traditional endoscope devices must be attached to a supporting structure that is fixed to an introducer cannula, the weight of such an assembly tends to pull on the introducer cannula, in one direction. This action can compromise the placement of the introducer cannula during the procedure and/or cause trauma to brain tissue. Thus, by incorporating illuminating ring 300 to outer sheath, such potential disadvantages may be avoided.

While illuminating ring 300 may be secured to grip ring 120 of outer sheath 102 in any suitable manner, in one exemplary arrangement, illuminating ring 300 is provided with a selective locking arrangement to selectively fix illuminating ring 300 to grip ring 120. In one exemplary arrangement, wall member 304 is provided with a locking channel 322, best seen in FIG. 11B. Locking channel 322 comprises wall opening 318 and that opens into a first channel segment 324, and a second channel segment 326 that is in communication with first channel segment 324. Wall opening 318 extends from a bottom surface 328 of wall member 304. Second channel segment 326 is spaced upwardly from bottom surface 328 of wall member 304 and is oriented at an angle from first channel segment 324. In one exemplary arrangement, second channel segment 326 is oriented 90° from first channel segment 324.

Figure 12:
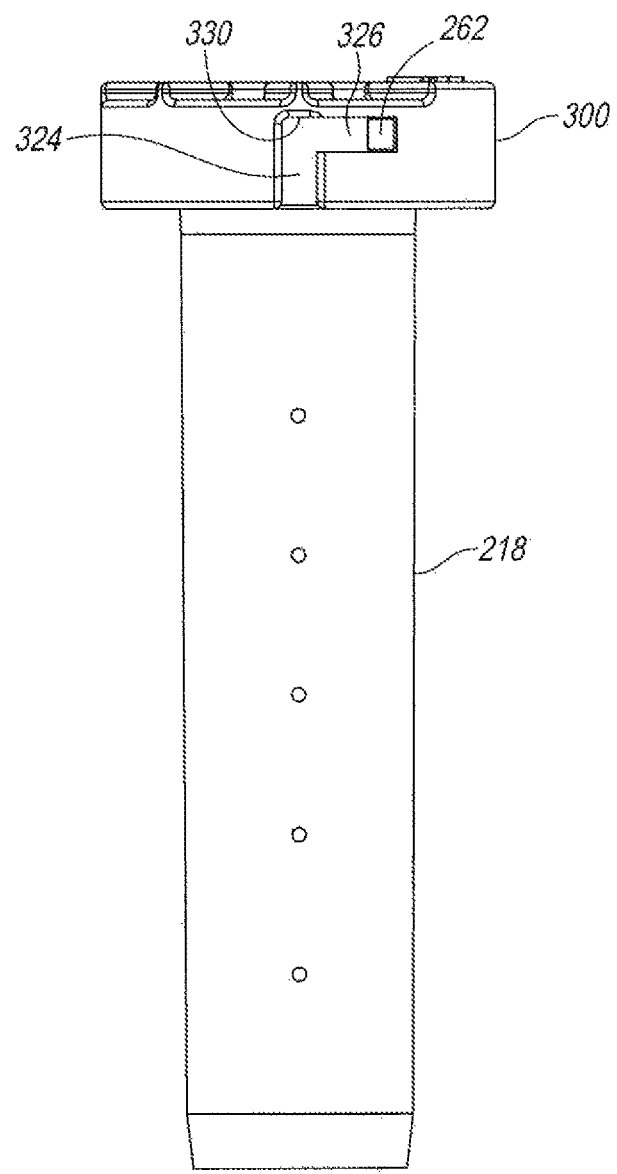
FIG. 12 illustrates the illuminating ring of FIG. 11A assembled to an exemplary embodiment of the outer sheath.

Locking channel 322 cooperates with locating member 262 to selectively secure illuminating ring 300 to grip ring 120. More specifically, illuminating ring 300 is pushed down over grip ring 120 with locating member 262 entering wall opening 318. As illuminating ring 300 is pushed downwardly, locating member 262 travels through first channel segment 324. Once locating member 262 contacts an terminal end 330 of first channel segment 324, illuminating ring 300 is rotated relative to outer sheath 102 such that locating member 262 moves into second channel segment 326, thereby selectively locking illuminating ring 300 to outer sheath 102, as shown in FIG. 12. Once connected, illuminating ring 300 thereby provides a hands-free light source to illuminate lumen 148 of outer sheath 102.

In one exemplary arrangement, certain segments of outer sheath 102 may be frosted so as to reflect light to increase visualization within outer sheath 102. For example, tapered portion 130 may be frosted. Similarly, the top of grip ring 120 may also be frosted.

Figure 13:
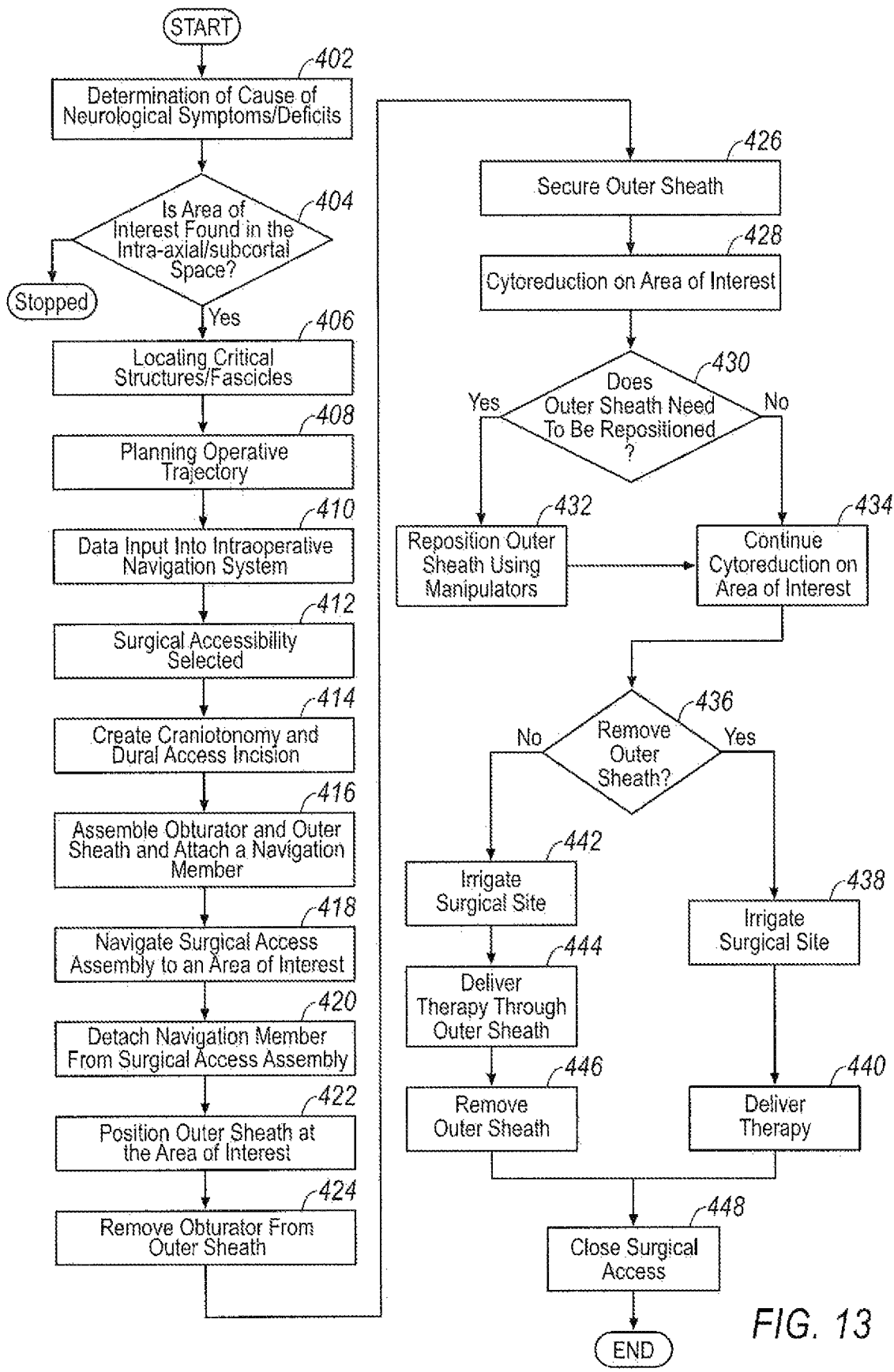
FIG. 13 is a flow chart illustrating a process flow using the surgical access assembly.

Operation of surgical access assembly will be described in connection with a process flow 400 illustrated in FIG. 13. Generally speaking, before any surgical procedure is decided upon, a patient will first present with symptoms or deficits requiring evaluation. Thus, the start of process flow 400 begins with a surgeon making a determination 402 of the cause of such neurological symptoms/deficits. Such a determination may be made through use of a variety of imaging modalities, including, but not limited to, MRI or CT imaging. The process then proceeds to step 404.

If the determination from step 402 finds that a brain condition is found, such as a tumor or hematoma, an additional determination is required. More specifically, a location of the brain condition is determined in step 404. If the imaging determines that an area of interest is located in the intra-axial/subcortical space, the process flow continues to step 406. However, if a brain condition is located in other, more easily accessible areas of the brain, the process flow stops.

Figure 14A:
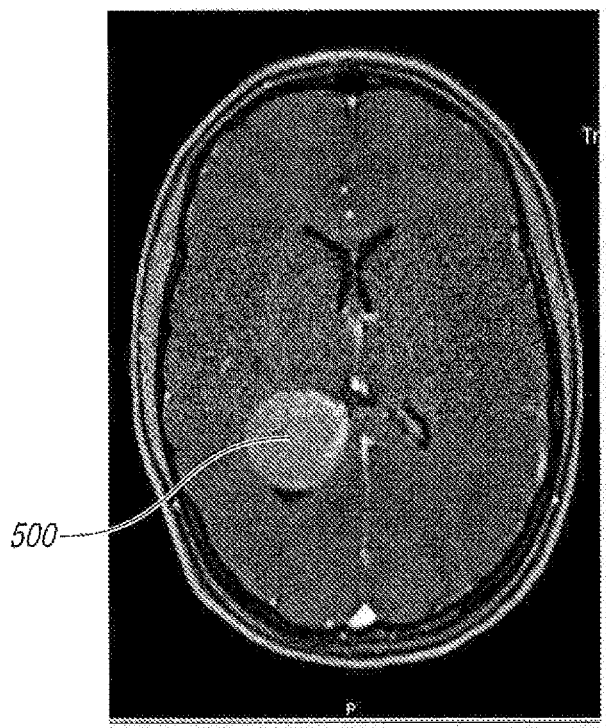
FIG. 14A-14B are images of a brain illustrating an area of interest, taken using an imaging modality.
Figure 14B:
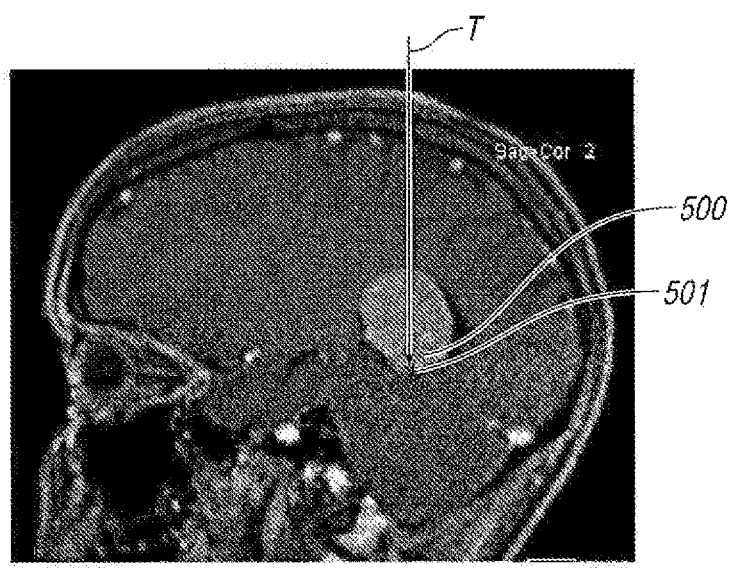

As discussed above, any suitable imaging modality may be utilized to determine if a brain condition exists, and if so, where that brain condition is located. FIGS. 14A and 14B illustrate examples of imaging results from an MRI. More specifically, an area of interest 500, in this case a tumor, may be seen deep in the subcoritcal space.

Once area of interest 500 is located, at step 406 an additional imaging sequence is employed to determine the location of eloquent structures such as vessels and fiber tracts and the associated fascicles so as to plan the safest access route to the area of interest. Exemplary arrangements for accomplishing this step include CT-Angiography and MRI with Diffusion Tensor Imaging (DTI) sequences. DTI allows for the determination of directionality as well as the magnitude of water diffusion along the communication "wiring" pathways called fiber tracts and fascicles. This kind of MRI imaging can provide imaging to allow for the estimation of potential damage to nerve fibers that connect the areas of the brain which can be affected by a stroke, for example, to brain regions that are distant from it, and can also be used to visualize white matter fibers in the brain and can map (trace image) subtle changes in the white matter associated with diseases such as multiple sclerosis and epilepsy, as well as assessing diseases where the brain's wiring is abnormal, such as schizophrenia, as well as tumor involvement.

Diffuse Tensor Tractography (DTT) may also be used. DTT allows for noninvasive racking of neuronal fiber projections in a living human brain. White matter fiber trajectories are reconstructed throughout the brain by tracking the direction of fastest diffusion, which is assumed to correspond to the longitudinal axis of the tract. Diffusion tensor tractography provides insight into white matter integrity, fiber connectivity, surgical planning, and patients prognosis. Once the imaging information has been analyzed, the process then proceeds to step 408.

Figure 15:
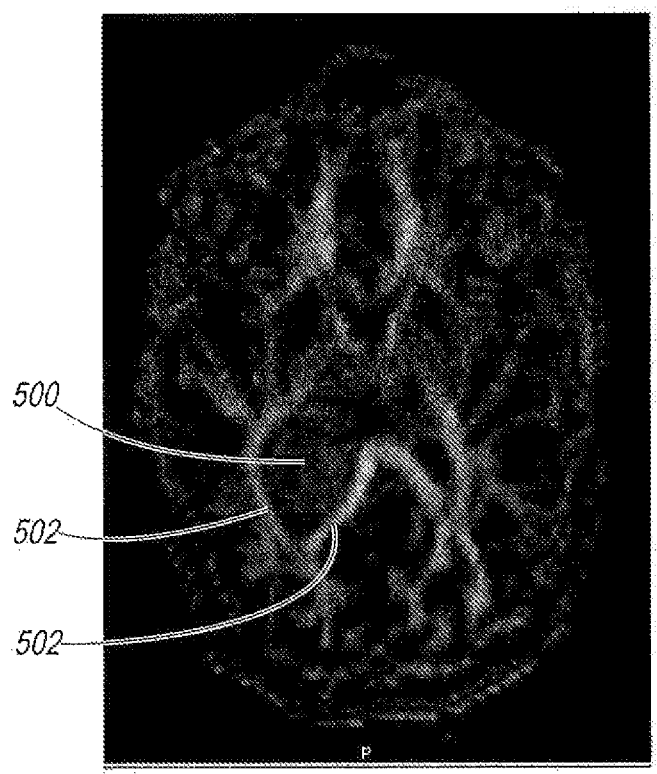
FIG. 15 is an image taken of the brain shown in FIGS. 14A-14B, illustrating various critical structures, such as fiber tracts and fascicles of the brain.

Referring to FIG. 15, an example of DTI imaging of the brain shown in FIGS. 14A and 14B is depicted. A map of fascicles and other vessels are illustrated in FIG. 15, including major vessels 502 that are shown spread around area of interest 500. Such images provide the surgeon with valuable information about potential avenues for access tracts to area of interest 500.

In step 408, a plan for the operative trajectory is developed. More specifically, imaging information is used to plan (either manually or with software) the access tract/pathway to achieve fiber tract involvement during access to the area of interest. In evaluating fiber tract involvement from a potential access tract/pathway, consideration of fiber tract importance may be based on an individual patient's occupational and personal needs and/or preference. Once a pathway has been planned, the process proceeds to step 410.

In step 410, image data from the MRI/DTI and CT/CTA image sequence obtained during step 406 is input into an intraoperative navigation system. Intraoperative navigation systems may be used to provide direct visualization of area of interest 500 in real time, as surgical access system 100 is being positioned within the brain. The method then proceeds to step 412

Once the procedure has been planned and the image data has been uploaded to a navigational system, step 412 requires that the appropriate sized surgical access assembly 100 is selected. First the appropriate size of a craniotomy must be determined. Further, the present disclosure contemplates that different diameter and length sizes of surgical access assembly 100 may be employed, the size depending on the particular location of area of interest 500. Accordingly, step 412 requires that the surgeon select the appropriate length and diameter of surgical access system 100 to be used, based on the physical and location characteristics of the area of interest 500. Once surgical access assembly 100 is selected, the process proceeds to step 414.

In step 414, the surgeon creates the craniotomy and Dural access incision. The process then proceeds to step 416.

In step 416, the obturator 104 is inserted into outer sheath 102 until grip ring 120 abuts first stop member 176, as shown in, for example FIG. 2. Navigation member 112 is then operatively connected to obturator 104.

As discussed above, various types of navigation members 112 may be employed with surgical access assembly 100. In one exemplary configuration, navigation member 112 is configured as a probe (as shown in FIG. 2). In this configuration, navigation member 112 is inserted through access opening 188 of grip member 178 until a distal tip 417 of navigation member 112 is deposited into depression 199 (see FIG. 9B). Depression 199 is formed so that distal tip 471 of navigation member 112 is positioned within the same plane as distal tip 132 of outer sheath 102, when obturator 102 and outer sheath 104 are assembled together as shown in FIG. 2. Locking member 110 may be tightened to fixedly retain navigation member 112 within obturator 102. A portion of navigation member 112 will extend proximally from grip member 178 and will be operatively connected to a navigation system that includes a screen that visually illustrates the information obtained from the imaging sequences, along with the trajectory of surgical access system 100. Thus, with the navigation member 112 operatively connected to a navigation system, the position of distal tip 132 of outer sheath may be indicated, in real time, while surgical access system 100 is being navigated within a body.

In another configuration, the software operating the navigation system may further be provided with an offset dimension that corresponds to a distance D3 between distal tip 174 of obturator 104 and distal tip 132 of outer sheath. In this arrangement, a dotted line may appear on the navigation screen that indicates where distal tip 174 of obturator 104 is located, in real-time.

Navigation member 112 may further be provided with image guidance position indicators, such as an array of reflectors of the type use in connection with optical image guidance systems. The infrared reflectors used with such a system are mounted to a handle of a probe-like navigation member 112 in a customary triangular configuration calibrated to identify the tool to the image guidance system. Such imaging systems are available, for example Medtronic Surgical Navigation Technologies (Denver, Colo.), Stryker (Kalamazoo, Mich.), and Radionics (Burlington Mass.).

Typically, the positioning of the indicators is calibrated such that the image guidance system can project an image of the tool onto a display of images of the patient's brain, such as MRI images used to plan surgery. Thus, as discussed above, as surgical access system 100 is inserted, the surgeon can see the relative position of system 100 relative to the structures of the brain as reflected on images, and particularly with respect to the target tissue.

Other guidance systems, such as magnetic or electromagnetic or radio transmitting systems may also be used, and the illustration of infrared reflectors and discussion of optical image guidance systems are exemplary only and are not intended to be limiting. In addition, while the exemplary method has been described in connection with superimposing an image of surgical access system 100 onto a pre-operative image, it is contemplated that real-time imaging capability may be utilized and that the image of surgical access system 100 may then be shown in relation to the surrounding tissue structures on a real time image.

In another exemplary configuration, an RFID chip may be embedded in obturator 104 that operatively communicates information to a navigation system or other surgical system about the specific attributes, such as, but not limited to, length and diameter. This information may be used to facilitate placement with the navigation system or other systems for information display or trajectory and location calculations during placement of obturator 104.

Figure 16A:
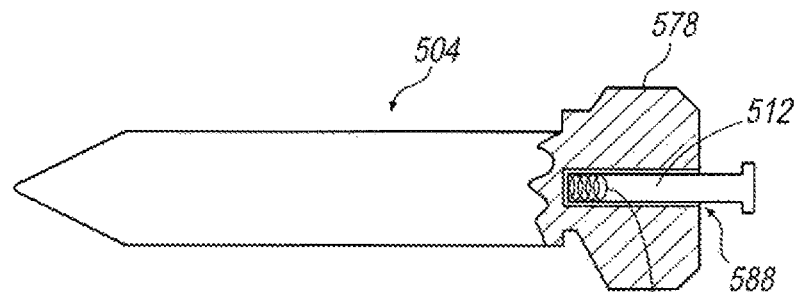
FIG. 16A is an alternative embodiment of an obturator with an imaging device operatively connected thereto.
Figure 16B:
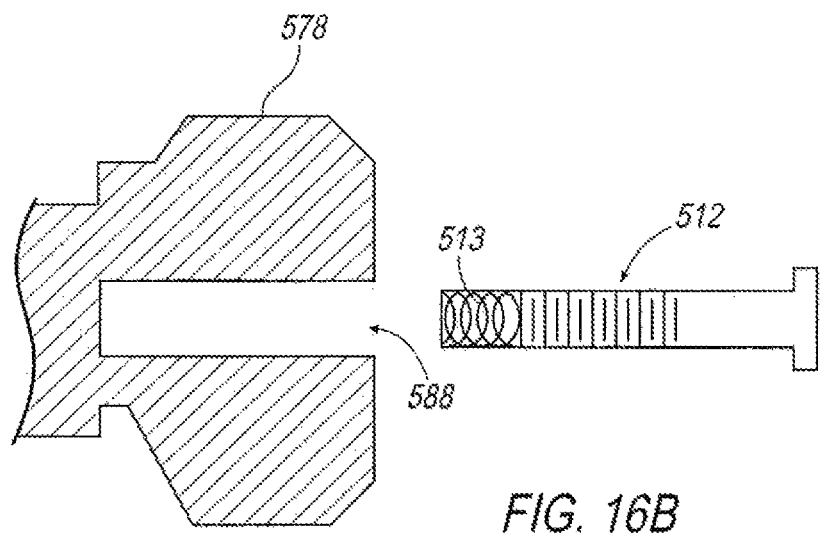
FIG. 16B is a partially exploded view of an enlarged cross-sectional view of the proximal end of the obturator and a post.

In yet another exemplary arrangement, as shown in FIGS. 16A-16B, an alternative embodiment of an obturator 504 may be used, wherein the obturator 504 is configured with a post 512 that is configured to operatively attach a navigation array. Post 512 may be detachably or permanently connected to grip member 578 of obturator 104. For example, as shown in FIG. 16A, post 512 is configured to be selectively detachable and may be used to capture a small coil 513 for MRI tracking of surgical access assembly 100. A portion of post 512 may be threaded and an access opening 588 formed in a proximal face of grip member 578 have be provided with corresponding threads (not shown) so as to affix post 512 to obturator 504. Other manners of selectively affixing post 512 to obturator 504 are also contemplated, including, but not limited to, a locking member 110 arrangement similar that shown in FIG. 2. As also discussed, post 512 need not be selectively detachable. Indeed, it is contemplated that post 512 may be permanently affixed to obturator 504, in any suitable manner, whereby the navigation array may be secured to post 512. In yet another alternative arrangement, obturator 504 may be configured such that a post, which is an element of the array itself, may be attached.

Figure 16C:
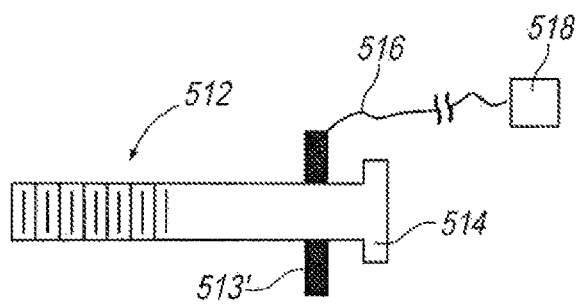
FIG. 16C is an alternative arrangement of a coil sensor for use with an obturator.
Figure 16D:
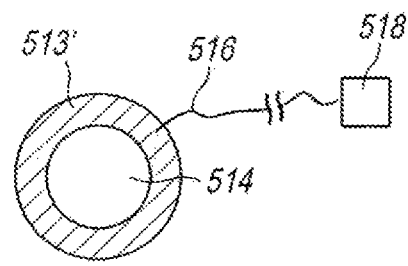
FIG. 16D is an end view of the coil sensor mounted on the post of FIG. 16C.

In still a further alternative arrangement, referring to FIGS. 16C-16D, a coil sensor 513' may be configured to be disposed about an outer periphery of post 512. In this arrangement, coil sensor 513' is slide or otherwise mounted to post 512 such that when post 512 is operatively attached to obturator 504 coil sensor 513' is captured between a portion of grip member 578 and a proximal end portion 514. A connecting wire 516 operatively attaches coil sensor 513' to an image position console 518.

Once surgical access assembly 100 is assembled and operatively connected to a navigational system, the process then proceeds to step 418, in which surgical access assembly 100 is navigated to area of interest 500. In one exemplary arrangement, distal tip 178 of obturator 104 is directed to a furthermost outer margin of area of interest 500. More specifically, referring to FIG. 14B, for example, surgical access assembly 100 is directed along a trajectory T that extends through area of interest 500 to a location 501 that may positioned within the margins of area of interest 500 or even slightly beyond the margin.

Due to the tapered configuration and closed, radiused distal tip 174 of obturator 104, as well as the radiused distal tip 132 of outer sheath 102, as surgical access assembly 100 is inserted into the brain and navigated to area of interest 500, tissue is gently pushed to either side of surgical access assembly 100, so as to atraumatically dilate tissue, while minimizing trauma to the tissue. Further, because surgical access assembly 100 is operatively connected to navigation member 112, as surgical access assembly 100 is being inserted into the brain tissue, navigation member 112 may cooperate with an imaging modality to providing real-time information concerning fiber tact in trajectory T, thereby allowing the surgeon to minimize fiber tract compromise or damage during insertion of surgical access assembly 100. Once surgical access assembly 100 is positioned at area of interest 500, the process proceeds to step 420.

As step 420, navigation member 112 removed from or detached from surgical access assembly 100. The process then proceeds to step 422.

Figure 17A:
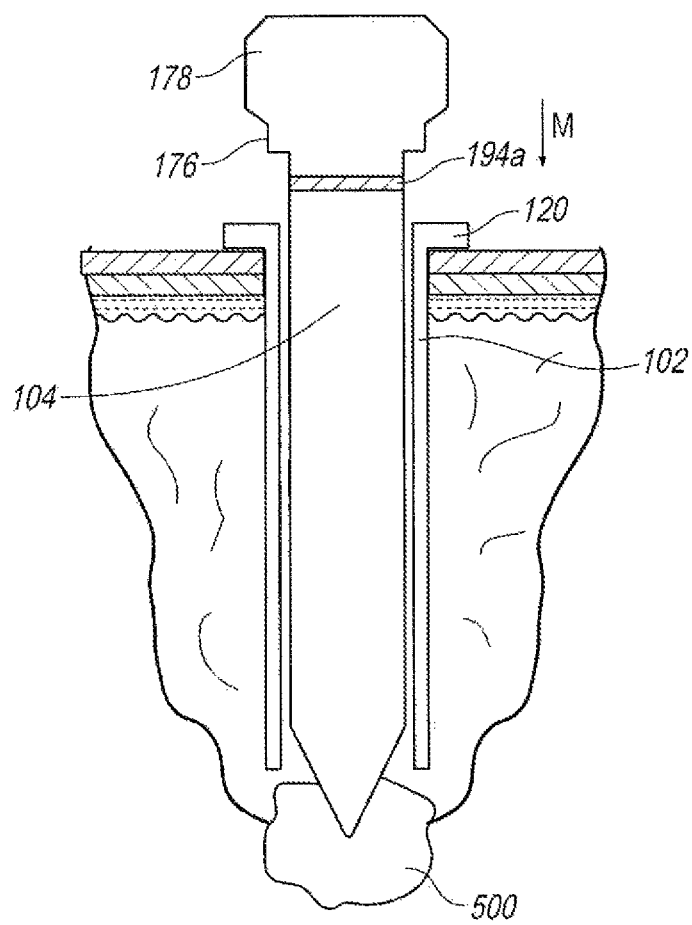
FIG. 17A is an elevational view of the surgical access system, while the obturator is being withdrawn from the outer sheath.

Once navigation member 112 is removed, outer sheath 102 is then operatively positioned with respect to area of interest 500. More specifically, as shown in FIG. 17A, outer sheath 102 is decanted with respect to obturator 104 such that distal end 108 of outer sheath 102 is moved toward distal end 106 of obturator 104, as indicated by arrow M. This action is accomplished by grasping grip ring 120 with one hand while maintaining obturator 104 stationary, such, for example, grasping grip member 178 with another hand. Grip ring 120 may be gently rotated and/or swiveled with respect to a central axis of obturator 104 to enable outer sheath 102 to be moved distally with respect to obturator 104. First stop member 176 aids in gripping and manipulating outer sheath 102, in that a gap 423 (see FIG. 2) is created between end surface 158 and a distal end surface of grip member 178. Outer sheath 102 is decanted until grip ring 120 aligns with indicator 194A (see FIG. 7A). Indicator 194A is spaced from first stop member 176 a distance that generally corresponds to the length of distal tip portion 172 of obturator 104. Accordingly, when grip ring 120 is aligned with indicator 194A, distal end 108 of outer sheath 102 is aligned tip member 174 of obturator 104. Moreover, outer sheath 102 is positioned within area of interest 500. The process then proceeds to step 424.

Figure 17B:
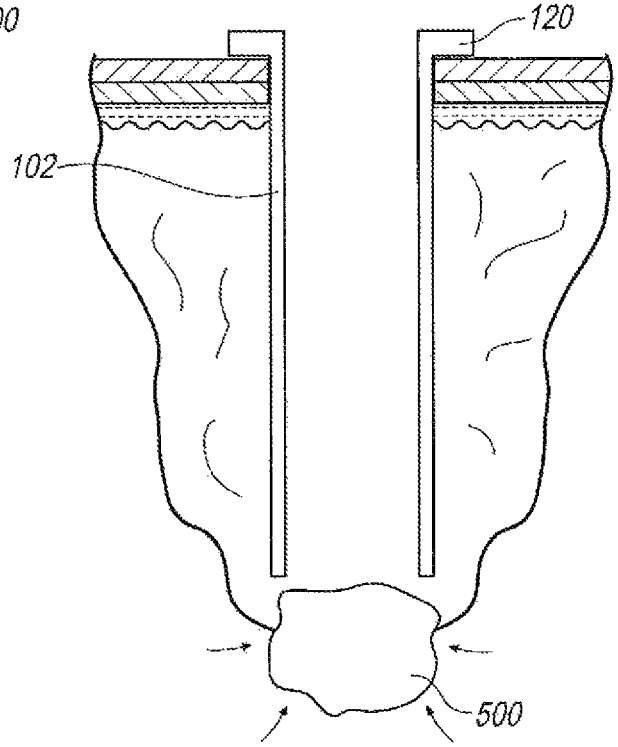
FIG. 17B is an elevational view of the surgical access system with the outer sheath in place within the brain.

In step 424, once outer sheath 102 is appropriately positioned, obturator 104 is then removed from outer sheath 102, as shown in FIG. 17B. More specifically, outer sheath 102 is maintained to be relatively stationary at area of interest 500, and obturator 104 is moved in a proximal direction until fully removed from outer sheath 102. This action results in outer sheath 102 forming a pathway to area of interest 500. The process then proceeds to step 426.

In step 426, outer sheath 102 is then secured in place so as to prevent cranial pressure from pushing outer sheath 102 out of the brain tissue. In one exemplary arrangement, a securing member may be utilized with small openings 150 on grip ring 120 to temporarily secure outer sheath 102. For instances where illuminating ring 300 is used with surgical access assembly 100, small openings 309 in illuminating ring 300 align with small opening 150 of grip ring. Accordingly, securing members may also be utilized with small openings 309. In the alternative embodiment shown in FIGS. 22-26, the holes 392 defined in the projections 390 which extend outward from the wall members 304 of the illuminating ring can be utilized to secure the outer sheath. However, the securing member may be secured so as to permit a limited degree of movement, as will be discussed below, so as to result in a floating system that permits selective repositioning. Suitable retaining members include, but are not limited to, bridle sutures, flexible bands with retaining hooks, or even repositionable retractor arms. Once outer sheath 102 is secured, the process then proceeds to step 428.

In step 428, debulking area of interest 500 may be conducted. Traditionally, a patient is given medication, such as, for example, Mannitol, before an intracranial operation to reduce intracranial pressure (ICP) of the brain prior to the surgery. Indeed, ICP is often experienced by patients due to the natural response of the craniotomy and/or the present of an abnormality within the brain. The present inventors have found that it may be advantageous to omit or minimize the use of medication for reducing ICP. More specifically, but not reducing IPC, because the brain tends to occupy the available space within the skull, after obturator 104 is removed from outer sheath 102, the target tissue may have a tendency to flow into, and present itself into the open distal end 108 of outer sheath 102, due to the cranial pressure. Area of interest 500 may actually move into outer sheath 102 on its own, thereby assisting in delivery and minimizing manipulation required of outer sheath 102 during the process.

It is contemplated that a wide range of surgical devices may be inserted into outer sheath 102 to remove tissue abnormalities. In one exemplary arrangement, it is contemplated that outer sheath 102 may have an inner diameter up to approximately 20 mm, to allow multiple instruments, such as graspers, dissectors, scissors, cautery and suction instruments to be inserted through outer sheath 102 to perform surgery.

Figure 18:
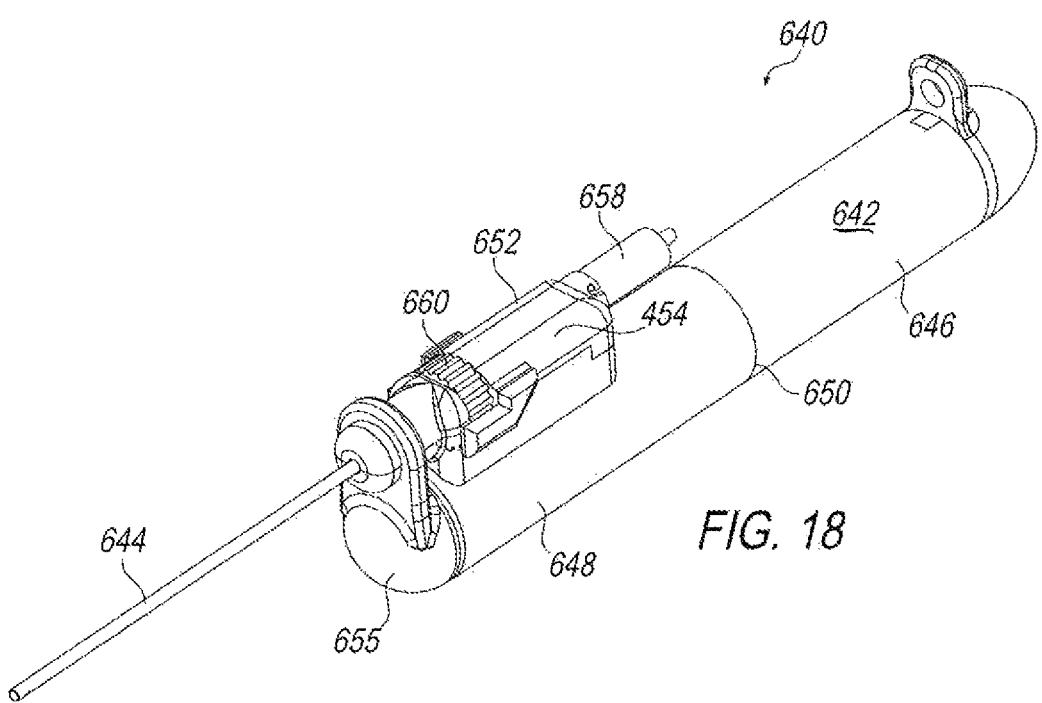
FIG. 18 is a perspective view of an exemplary surgical device used for cytoreduction.

One exemplary surgical device that may be used is the NICO MYRIAD® manufactured and distributed by Nico Corporation of Indianapolis, Ind. Referring to FIG. 18, an exemplary surgical cutting device 640 is shown, such as that disclosed in co-pending, and co-owned with the assignee of the present application, U.S. patent application Ser. No. 12/389,447, the contents of which are incorporated by reference in its entirety. Surgical cutting device 640 includes a handpiece 642 and a cutting element that includes an outer cannula 644 and an inner cannula (not shown). In one exemplary configuration, handpiece 642 is configured with a generally cylindrical shape. Handpiece 642 may be sized and shaped to be grasped with a single hand. Handpiece 642 also includes a lower housing 650 comprising a proximal section 646 and a distal section 648. A front housing section 655 may be connected to a cam housing positioned in distal section 648. An upper housing 652 is also provided. The cutting element is mounted to upper housing 652 and may be fluidly connected to a tissue collector 658. In one exemplary arrangement, tissue collector 658 may be operatively connected directly to upper housing 652. Alternatively, tissue collector 658 may be remotely connected to the cutting element by appropriate tubing. A vacuum line (not shown) may be connected to a proximal end of tissue collector 658 to direct tissue into the cutting element, as well as to deliver severed tissue to tissue collector 658. A rotation dial 660 for selectively rotating the outer cannula 644 with respect to handpiece 642 is also mounted to upper housing 652, to provide controlled cutting action.

Use of surgical device 640 is advantageous in that space is limited to effectuate tissue debulking, such that use of traditional surgical scissors may be challenging, especially when other instruments are inserted into outer sheath 102 simultaneously. Moreover, fibrosity of a tumor may present challenges for the use traditional suction debulking devices. Traditional graspers operate by tearing tissue of interest. However, the tearing action may become problematic if vessels or fascicles are too close to the tissue being torn in that such vessels or fascicles may also be torn.

Figure 19A:
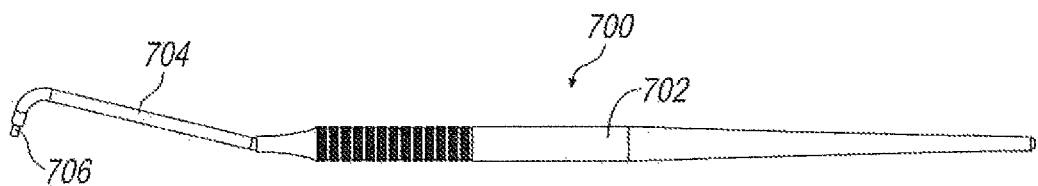
FIG. 19A is an elevational view of an exemplary manipulation member.
Figure 19B:
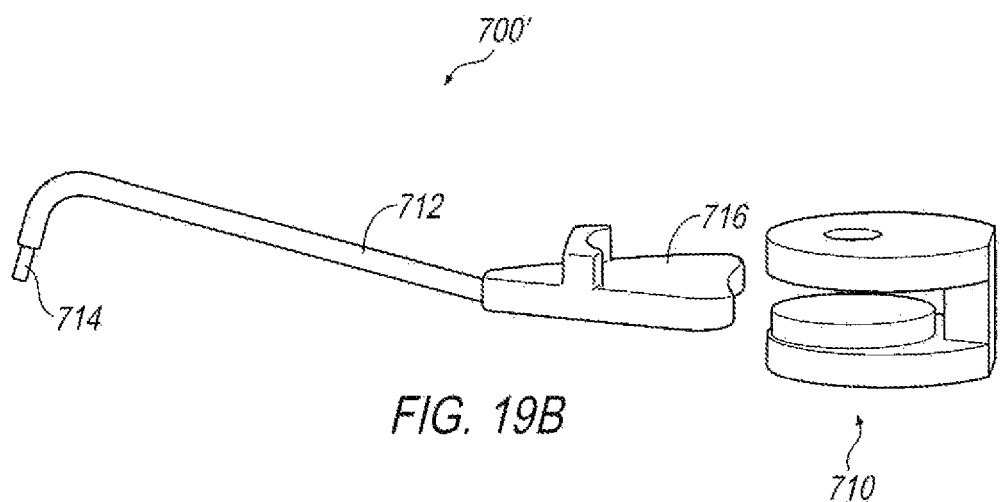
FIG. 19B is an elevational view of an alternative manipulation member.

In step 428, as area of interest 500 is cytoreductively debulked, it may become necessary to reposition or move outer sheath 102. If repositioning is necessary, the process moves to step 432. To that end, in one exemplary arrangement, manipulation members may be provided. Examples of manipulation members 700 and 700' are illustrated in FIGS. 19A-19B. Manipulation member 700 comprises a handle member 702 that supports an armature 704, and a hook element 706 that extends from armature 704. Hook element 706 is sized to fit within small openings 150 and 309 disposed within grip ring 120 and illuminating ring 300, respectively. In the alternative embodiment shown in FIGS. 22-27, the hook element 706 fits within small openings 388 in the exterior face 394 of the housing 380. In operation, hook element 706 is engaged with a small opening 150/309/388 and handle member 702 is used to gently push or pull outer sheath 102. Because outer sheath 102 is only loosely secured, outer sheath 102 may be selectively moved slightly for improved visualization or to access tissue. After outer sheath 102 has been repositioned, or if repositioning of outer sheath 102 is not necessary, the process moves to step 434, and cytoreduction of area of interest 500 continues.

In an alternative arrangement, manipulation member 700' may be secured to a flexible holder member 710. Manipulation member 700' comprises an armature 712 that carries a hook element 714 and an engagement portion 716. Engagement portion 716 operatively engages holder member 710 so as to fixedly secure manipulation member 700' to holder member 710, thereby freeing a surgeon's hand, once outer sheath 102 is positioned. It is understood that multiple manipulation members 700/700' may be utilized to permit a surgeon to selectively push or pull outer sheath 102.

Outer sheath 102 is configured such that multiple instruments may be inserted simultaneously therewithin, thereby increasing the speed and safety of surgical procedures. In one exemplary arrangement, an endoscope may be partially inserted and held to one side of outer sheath 102, to provide an image of area of interest 500 to a monitor, while a surgical instrument, such as surgical instrument 640 is also inserted within outer sheath 102. Illuminating ring 300 may also be used, with the endoscope and the surgical instrument being inserted through access opening 308 that aligns with opening 146 of grip ring 120. Because illuminating ring 300 provides the necessary light for outer sheath 102, a relatively small diameter endoscope may be used, thereby increasing the available space within outer sheath 102 for other surgical instruments. In another exemplary configuration, the surgeon may have both a surgical instrument and a cautery instrument simultaneously inserted into outer sheath 102, thereby permitting the surgeon to cauterized vessels that are encountered during the procedure.

In another exemplary arrangement, during the procedure, fluorescing dye may be introduced into the patient, either before surgery or during the surgery. One such dye is Glioan (5-Aminolevulinic Acid), however other suitable dyes may also be used. The fluorescing dye may be introduced by any suitable methods, including, but not limited to, injecting the patient with the dye, providing the dye orally to the patient prior to surgery, or even injecting the dye in situ through outer sheath 102. In one exemplary arrangement, the dye is configured to bond to proteins of abnormal cells such that the cells are visually distinguishable from healthy cells. With this visual indication of healthy vs. abnormal tissue, the surgical instrument may be more efficiently used to resect abnormal tissue. In other embodiments, light delivered through outer sheath 102 has a predetermined wavelength that is configured to interact with the dye to illuminate or fluoresce abnormal tissue. For example, illumination cap 300 may be provided with LED lights of a preselected wavelength that operatively interacts with a preselected dye to illuminate abnormal tissue and assist with differentiating healthy tissue from diseased tissue.

In another exemplary configuration, a light probe or fiber optic bundle (not shown) may be inserted into outer sheath 102 to assist with differentiation between healthy tissue and abnormal tissue. In one arrangement, the probe/bundle is simply inserted into outer sheath 102 as a separate element, along with a surgical device. The probe/bundle is operatively connected to a console such that the reflected light is delivered to the console. A sensor in the console (i.e., the sensor is remotely located from the point of detection, receives the reflected light to trigger a signal to the user based on predetermined parameters. In other words, the natural florescence of the tissue is then reflected back to the console to inform the user whether or not the tissue is diseased or abnormal.

Figure 20:
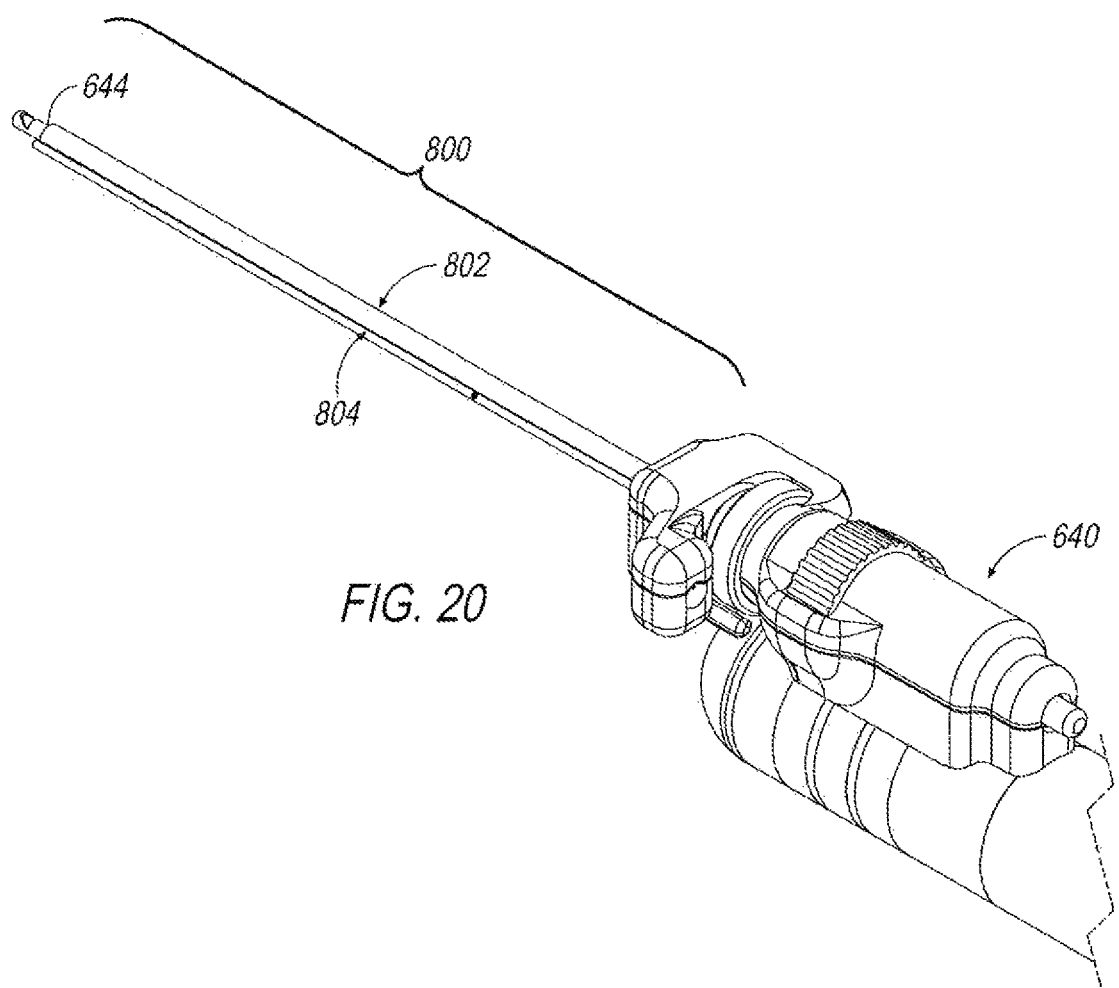
FIG. 20 is a partial perspective view of an exemplary delivery sleeve that may be used with a surgical device.

In another exemplary configuration, the surgical device may be further provided with a delivery sleeve 800 that mounts to surgical device 640, and example of which may be found in FIG. 20. Various embodiments of delivery sleeve 800 may be found in co-pending, and co-owned with the assignee of the present application, U.S. patent application Ser. No. 13/269,339, the contents of which are incorporated by reference in its entirety. As may be seen in FIG. 20, delivery sleeve 800 generally includes at least two lumens, a first lumen 802 which is configured to receive outer cannula 644 of surgical device 640, and a second lumen 804 which is configured to receive an optical device, such as a light probe or a fiber optic bundle (not shown). Use of this arrangement permits use of additional surgical tools/instruments within outer sheath 102. More specifically, as the optical device is supported within the delivery sleeve 800, which, in turn, is connected to the surgical device, the surgeon can simultaneously differentiate between abnormal and healthy tissue, and resect tissue, all with by just holding the surgical device 640. As a result, the surgeon may also choose to utilize a separate cautery device within outer sheath 102 to permit cauterization of any vessels during the resection, in real time, and without requiring removal of the surgical device 640.

Because outer sheath 102 may be directly positioned at area of interest 500 in such a manner as to avoid unnecessary damage to critical structures, and because surgical device 640 may be placed directly at the sight of area of interest, utilizing surgical access system 100 provides the ability to resect most of an area of interest 500, such as a tumor. As one of ordinary skill in the art can appreciate, the more that a tumor is resected and removed, the less adjuvant therapy is required for treatment. In other words, the more diseased tissue there is resected, the less diseased tissue there is to destroy.

Once a cytoreductive resection of area of interest 500 has been completed, the process then proceeds to step 436. In step 436 a decision is made to either remove outer sheath 102 or to leave outer sheath 102 in position. More specifically, for some therapy applications removal of outer sheath 102 may be more effective than leaving outer sheath in place to deliver the therapy. If the decision is made to remove outer sheath 102, after removal of outer sheath 102, the process 400 proceeds to step 438.

As one of ordinary skill in the art may appreciate, the natural elasticity of brain tissue will maintain access or a corridor to area of interest 500 for a period of time. In step 438, while the corridor is still intact after removal of outer sheath 102, in one exemplary arrangement, a delivery device may be inserted into the corridor to deliver irrigation to the surgical site. In some instances, a syringe may be inserted into the corridor to deliver an irrigating fluid, such as saline directly to the surgical site. In another exemplary configuration, a drainage catheter (which is configured with a plurality of small openings at its distal end) is delivered into the corridor such that the distal end of the catheter is placed at or adjacent the surgical site. Irrigating fluid is then introduced into the proximal end (such, as for example, by operatively attaching a syringe barrel to the proximal end), to deliver the irrigating fluid to the surgical site. The irrigating fluid flushes out debris and assists in the brain tissue's natural tendency to close back in on itself. Once the surgical site has been irrigated, it may also be desirable to deliver certain therapies to the surgical site. For example, certain therapies that may be provided in liquid form may be directly injected through the corridor, just prior to the tissue closing back in on itself. Because the corridor is closing, the therapy will be held in place at the surgical site, thereby increasing its effectiveness at the site and surrounding tissue.

In some therapy methodologies, outer sheath 102 may be necessary to aid in the delivery and/or placement of such therapy, as will be explained in further detail below. Accordingly, if the decision in step 436 is made to keep outer sheath 102 in place after completion of cytoreduction, the process 400 proceeds to step 442.

In step 442, area of interest/surgical site 500 is irrigated to again remove any debris from the area. Irrigation may be performed in the same manner as discussed in step 438, except through outer sheath 102. Once irrigation is complete, the process proceeds to step 444.

In step 444 a therapy is delivered to area of interest 500. In one exemplary configuration, intraoperative radiotherapy (IORT) may be employed, so as to deliver therapy directly to area of interest 500 through outer sheath 102. In one exemplary configuration, an implantable therapy may be applied to area of interest 500. Example of an implantable therapy include: bioabsorbable radiation pellets, wafers or mesh, such as, for example, those manufactured by Nano-Rad LLC. Other examples include, but are not limited to, titanium capsules or seeds with radiation contents, bioabsorbable gels or foams that contain radioactive, chemotherapy or immunotherapy agents.

In another exemplary configuration, a balloon catheter may be used to perform brachytherapy following the removal of diseased tissue at area of interest 500. For example, a balloon catheter may be inserted through outer sheath 102 and delivered to area of interest, and then the balloon catheter may be inserted with a predetermined amount of radioactive solution followed by the delivery of radiation to the surrounding tissues. A commercially available catheter that may be used includes the GliaSite balloon catheter, with an Iotrex radioactive solution. Use of a balloon catheter may provide a more targeted delivery of liquid radiation, thereby reducing impact on brain tissues surrounding the diseased tissue.

In another exemplary arrangement, an electron beam driven X-ray source may be provided. One such exemplary configuration is the Zeiss INTRABEAM®. The electrons are generated and accelerated in a main unit and travel via an electron beam drift tube which is surrounded by a conical applicator sheath such that its tip lies at an epicenter of an applicator sphere to provide a point source of low energy X-rays at the tip. With this configuration, a nearly isotropic field of low energy is emitted.

In operation, the applicator sheath is inserted through outer sheath 102 and into the surgical cavity at area of interest 500. An intraoperative ultrasound may be performed to determine the distance of the applicator surface to the skin, to avoid significant skin doses. The applicator sheath may be secured into place by the surgeon using subcutaneous sutures around the neck of the sphere, similar to that described above in connection with outer sheath 102.

In another exemplary arrangement, a photodynamic therapy may be used, whereby a predetermined chemical composition may be provided to the patient and the chemical composition may be selectively activated by a predetermine wavelength, thereby achieving a therapeutic reaction. For example, in one exemplary configuration, illuminating ring 300 may be turned on to achieve the therapeutic reaction. In another exemplary configuration, a light source, such as, for example, a fiber optic bundle, may be directed through outer sheath 102, either directly through outer sheath 102 or through delivery sleeve 800.

In yet another exemplary configuration, external beam high frequency ultrasound or interstitial high frequency ultrasound may also be delivered through outer sheath 102 and directly to area of interest 500.

Figure 21A:
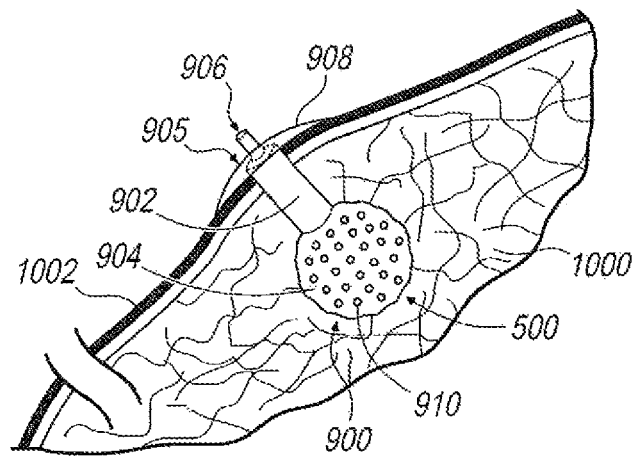
FIG. 21A is an exemplary arrangement for a therapy delivery device.
Figure 21B:
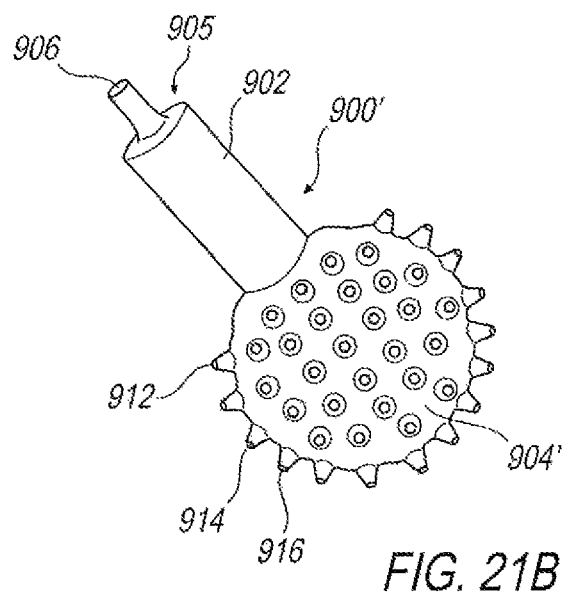
FIG. 21B is an alternative arrangement of the therapy delivery device of FIG. 21A.

In yet a further exemplary configuration, as show in FIGS. 21A-21B, an implantable delivery device 900/900' may be provided. Implantable delivery device 900/900' includes a neck portion 902 that is connected to a body portion 904/904'. Both neck portion 902 and body portion 904/904' may be constructed of a relatively soft and flexible material. Body portion 904/904' defines a reservoir for holding a therapeutic agent therein. A proximal end 905 of neck portion 902 is largely closed, with access to an interior of implantable delivery device 900/900' being providing by a luer port 906. More specifically, therapy agents are introduced into delivery device 900/900' through luer port 906. A sealing flange 908 may further be provided, that operatively connects the neck portion 902 to assist in holding implantable delivery device 900/900' in place within the brain.

In the arrangement show in FIG. 21A, body portion 904 may be provided with at least one small opening 910. In one exemplary arrangement, a plurality of small openings 910 are provided, and such openings may be spaced equidistance from one another about the periphery of body portion 904. Small openings 910 are configured to permit the therapy agent that is introduced through luer port 906 to weep out of the reservoir formed by body portion 904 at a controlled rate to increase effectiveness. Alternatively, body portion 900 may be configured as a permeable membrane that permits slow and controlled passage of therapy from the reservoir to the brain tissue 1000.

In an alternative arrangement shown in FIG. 21B, body portion 904' may be provided with flexible finger-like projections 912. In one exemplary configuration, projections 912 are spaced equi-distance from one another about the periphery of body portion 904'. Projections 912 extend outwardly from an outer periphery of body portion 904' and may be formed with channels that provide communication between the reservoir and small openings 914 configured at distal tips 916 of projections 912. Openings 914 are configured to permit the therapy agent that is introduced through luer port 906 to weep out of the reservoir. Projections 914 assist in frictionally retaining delivery device 900' at a target site.

Referring back to process 400, if delivery device 900/900' is employed, delivery device 900/900' is inserted at area of interest 500 through outer sheath 102. Once positioned, outer sheath 102 is removed, and sealing flange 908 is operatively connected to neck portion 902 such that luer port 906 is accessible. Sealing flange 908 is configured to extend over the periphery of the surgical access opening that was formed through the skull 102, thereby providing protection for the exposed brain tissue 1000. The therapeutic agent may be supplied to the reservoir formed by body portion 904/904' either before delivery device 900/900' is positioned at area of interest 500, or after sealing flange 908 is in place. Sealing flange 908, as well as body portion 904/904' and neck portion 902 may be configured with flexible material to allow for sealing against the dura and bone of the brain.

In yet another alternative arrangement involving delivery device 900/900', a transfer material may be delivered through outer sheath 102, similar to a foam that is configured to conform to the cytoreducted area of interest 500. The foam will allow continuous contact with the therapy agent that weeps through body portion 904/904' to provide a controlled dosage of therapy to area of interest 500.

After surgery and therapy on the target tissue is complete, the process proceeds to step 446. In this step, the instruments used for surgery and/or therapy are removed from outer sheath 102. As the target tissue is removed, brain tissue will fill the void formed by removing area of interest 500 so that healthy brain tissue underlying the now removed target tissue is adjacent the end of outer sheath 102. Outer sheath 102 is then gently removed and the brain tissue will naturally fill and reclaim the space formerly occupied by the abnormality and outer cannula 102, aided by the irrigation of area of interest 500. Moreover, as the brain tissue reclaims the space formerly occupied by the abnormality and outer cannula 102, implanted therapies, such as, for example, bioabsorbable radiation pellets, wafers or mesh, will be held in place by area of interest 500 to provide effected treatment. While this process may take several minutes, it is relatively atraumatic. Once outer sheath 102 has been removed, the process continues to step 448, whereby the dura, skull and scalp are then closed in a known manner and the process ends. In the exemplary cases whereby a treatment device may be implanted, full reclaiming of the space is delayed due to the implant until implant is explanted or absorbed.

Because the location of the area of interest will vary from patient to patient, in one exemplary arrangement, it is contemplated that surgical access system 100 will be provided as part of a kit. More specifically, it is contemplated that a set of multiple obturators 104 may be provided that have different lengths and/or diameters. The set may be provided in a container that is configured be sterilized, with obturators 104 secured therein. It is also contemplated that a set of manipulation tools 700/700' may also be provided with the kit, and that manipulation tools 700/700' may be positioned within the container for selective sterilization. Outer sheath 102 may be provided with the kit, in various lengths and diameters that correspond to the lengths and diameters of obturators 104 provided in the kit. However, in one exemplary arrangement, outer sheaths 104 are provided separately as single use devices, in sterilized pouches.

Figure 22:
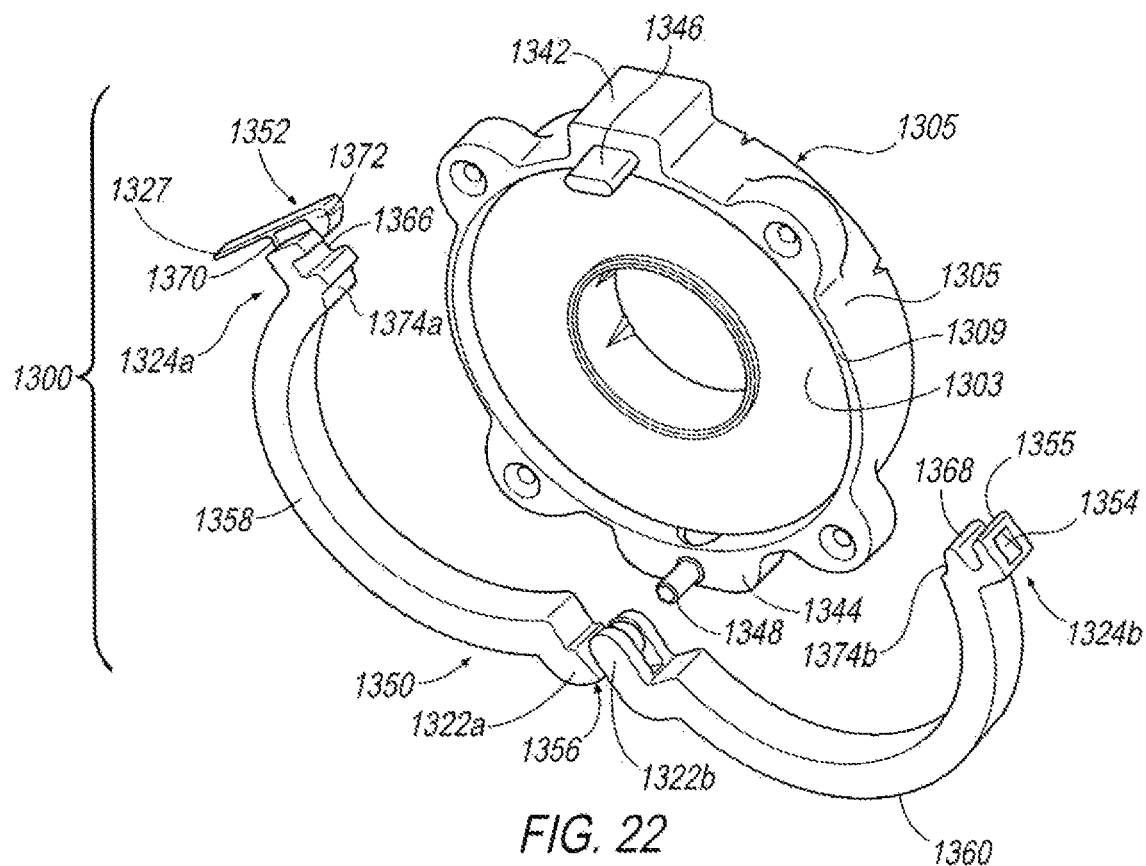
FIG. 22 is a partially exploded view of an alternative arrangement of an illuminating ring assembly.

Alternative embodiments of illuminating ring assemblies will now be discussed. A first alternative embodiment of an illuminating ring assembly 1300, as well as securing arrangements operable to secure illuminating ring assembly 1300 to a grip ring, such as grip ring 120 of outer sheath 102, is shown in FIGS. 22 through 27. In one exemplary arrangement, as shown in FIG. 22, illuminating ring assembly 1300 is defined by a housing 1304 having a wall member 1305 and a cover (best seen in FIG. 27). A light member 1303 is positioned within housing 1304. Housing 1304 (and light member 1303) further includes an opening 1307 therethrough that is configured to receive medical instruments therein, as described above. Extending outwardly from a bottom surface of wall member 1305 is a securing member 1346. A positioning member 1348 that also extends outwardly from a bottom surface of wall member 1305 may be provided. In one exemplary configuration, wall member 1305 is provided with one or more protrusions 1342, 1344 that extend radially outwardly from a periphery of wall member 1304 upon which securing member 1346 and positioning member 1348 may be mounted. Protrusions 1342, 1344 may be located opposite one, although other convenient arrangements are also contemplated.

Illuminating ring assembly 1300 further includes a selectively closable attachment mechanism 1350. In one exemplary configuration, attachment mechanism 1350 is a hinged attachment mechanism, as may be seen in FIG. 22, for example. However, it is understood that other attachment mechanisms may be employed and are contemplated by the scope of this disclosure. With respect to attachment mechanism 1350 in FIG. 22-27, hinged attachment mechanism 1350 may include a centrally located hinge member 1356 and two arms 1358, 1360 positioned on either side of hinge 1356. Each arm 1358, 1360 is defined by first and second ends, 1322a, 1322b and 1324a, 1324b, respectively.

In embodiment shown, second end 1324a of arm 1358 has a latching mechanism 1352 to attach second end 1324a of arm 1358 to second end 1324b of arm 1360. In one exemplary arrangement, arm 1360 (i.e., the arm without latching mechanism 1352) may, depending on configuration of latching mechanism 1352, be configured with a latching recess 1354 configured to receive a portion of latching mechanism 1352. More specifically, in one exemplary arrangement, latching recess 1354 is configured to accept a protuberance 1372 that is disposed on latching mechanism 1352. Recess 1354 may be defined by a forward edge 1355 with a rounded lip.

Latching mechanism 1352 may further include an actuating end 1327 and a pivot member 1370. Pivot member 1370 serves to mount latching mechanism 1352 to second end 1324a of arm 1358. Operation of latching mechanism 1352 will be described below in further detail.

Figure 23:
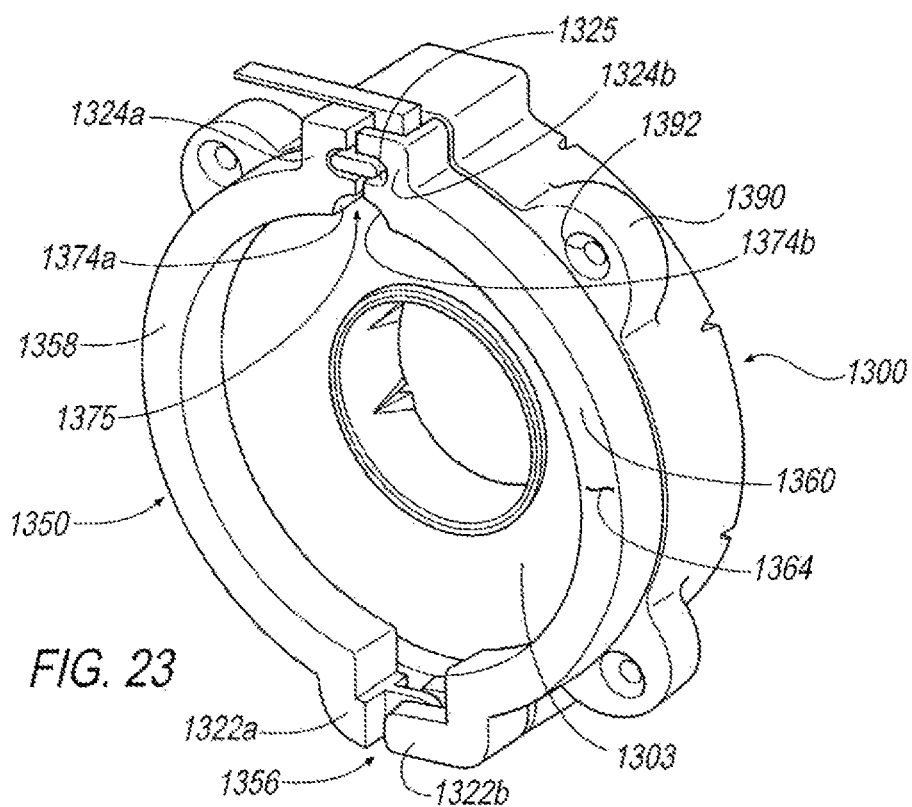
FIG. 23 is an elevational view of the illuminating ring assembly of FIG. 22 in an assembled configuration.

Hinged attachment mechanism 1350 has two sides, an obverse side 1364 and a reverse side, opposite thereto. As illustrated in FIG. 23, the reverse side is configured to abut at least a bottom surface 1309 of illuminating ring assembly 1300. In one embodiment, hinged attachment mechanism 1350 further includes a mounting cavity (not shown) that is configured so as to accept positioning member 1348 therein. Alternatively, a cavity may be located elsewhere on hinged attachment mechanism 1350.

Hinged attachment mechanism 1350 is configured such that second ends 1324a, 1324b of arms 1358, 1360 are selectively rotatable toward one another. Further, in one exemplary arrangement, when positioning member 1348 is positioned within the cavity of hinged attachment mechanism 1350, arms 1350, 1360 may be selectively rotated around positioning member 1348. More specifically, arms 1358, 1360 may be rotated in such a way that second ends 1324a, 1324b of arms 1358, 1360 are rotated toward securing member 1346.

In one exemplary arrangement, second ends 1324a, 1324b of arms 1358, 1360 may each be configured with complementary depressions 1366, 1368 (best seen in FIG. 22). Depression 1366, 1368 are oriented toward one another when arms 1358, 1360 are rotated together so as to define a securing hole 1325 (see FIG. 23) that is configured to accept a portion of securing member 1346. More specifically, securing hole 1325 is configured to be substantially the size and shape of securing member 1346, best seen in FIGS. 23, 24, and 26.

As shown in FIG. 23, when second ends 1324a, 1324b of arms 1358, 1360 of hinged attachment mechanism 1350 are brought together, the second ends 1324a, 1324b may be locked together by latching mechanism 1352. When second ends 1324a, 1324b of arms 1358, 1360 of hinged attachment mechanism 1350 are brought toward one another, a forward edge of protuberance 1372 on latching mechanism 1352 is forced upward from a neutral position by forward edge 1355 of recess 1354 until protuberance 1372 passes over forward edge 1355 of recess 1354 and comes to rest in recess 1354, thus locking arms 1358, 1360 in position.

In one exemplary arrangement, second ends 1324a, 1324b may further include cooperating indentations 1374a, 1374b. Indentations 1374a, 1374b are configured to cooperate to define a locking member recess 1375 (see, e.g., FIG. 23) when second ends 1324a, 1324b are locked together, as will be explained below.

Figure 24:
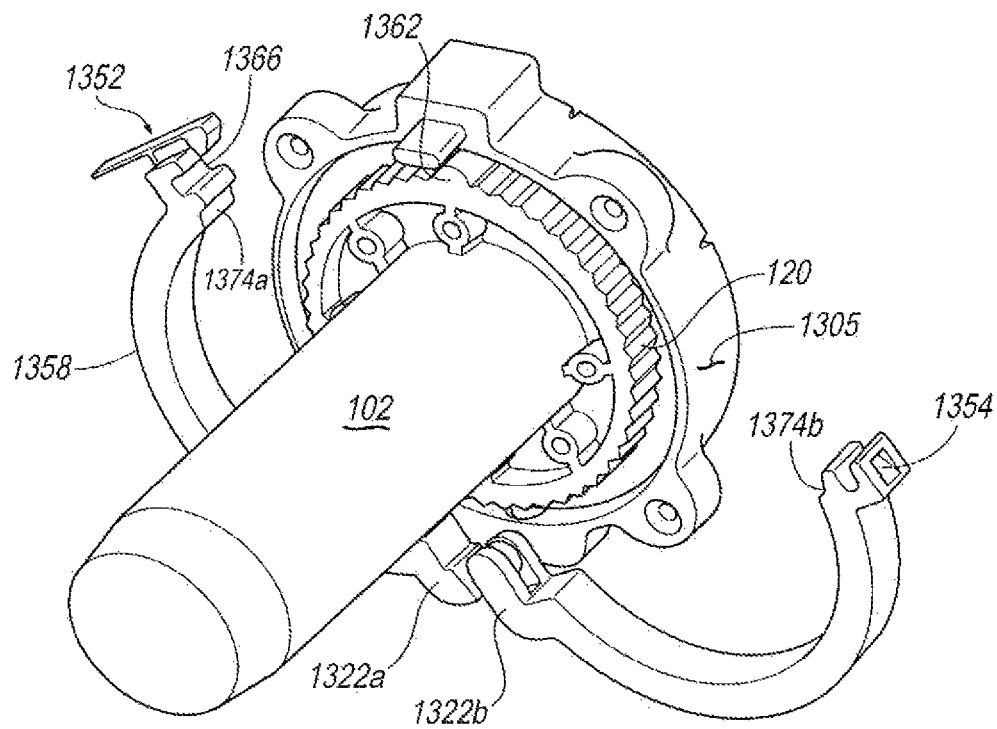
FIG. 24 is a partially exploded view of the illuminating ring assembly of FIG. 22 with an outer sheath operatively engaged therewith.
Figure 25:
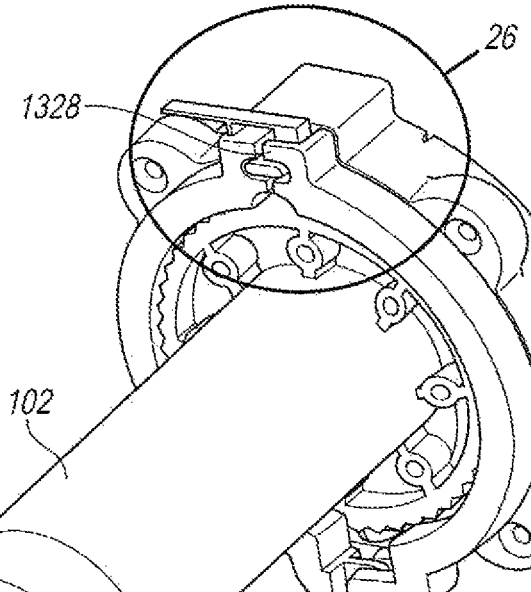
FIG. 25 is a perspective view of the illuminating ring assembly of FIG. 22, in an assembled configuration.
Figure 26:
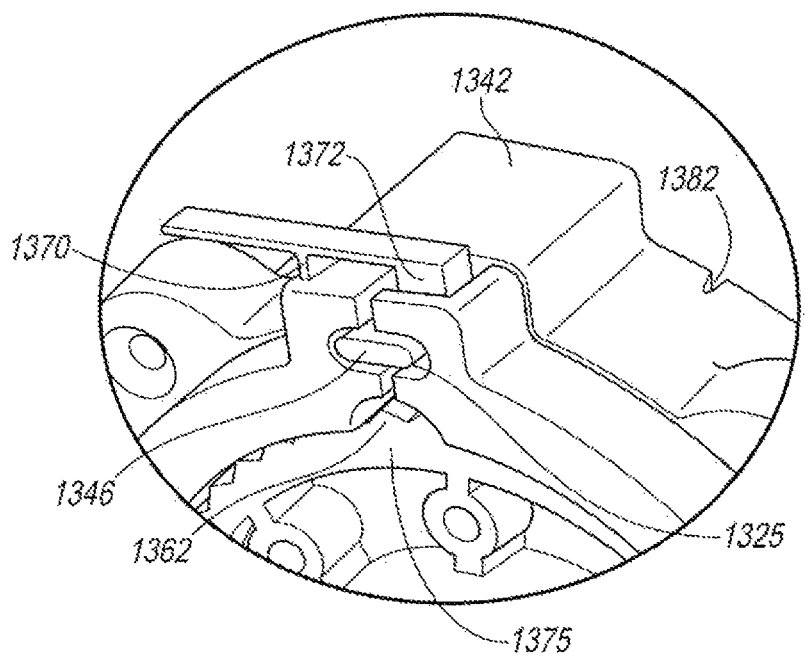
FIG. 26 is an enlarged perspective view of the illuminating ring assembly taken from areas 26 in FIG. 25.

In operation, illumination ring assembly 1300 is mounted onto grip ring 120 of outer sheath 102. More specifically, wall member 1305 of housing 1304 of illumination ring assembly 1300 is sized to receive grip ring 120 therein, as shown in FIG. 24, for example. Hinged attachment mechanism 1350 is mounted onto housing 1304 such that positioning member 1348 is received within the mounting cavity of hinge member 1356. First and second arms 1358, 1360 are pivoted about hinge member 1356 and second ends 1324a, 1324b are brought together, as shown in FIG. 25. As may be seen, depressions 1366, 1368 are also brought together to form securing hole 1325 around securing member 1346 such that securing member 1346 is captured within securing hole 1325. Locking member recess 1375 is also formed by second ends 1324a, 1324b as those ends come together. Locking member recess 1375 is configured to receive a locating member 1362 of grip ring 120 (see FIG. 26) to ensure proper assembly of hinged attachment mechanism 1350 to housing 1304.

Once second ends 1324a, 1324b are brought together, locking mechanism 1352 is actuated with protuberance 1372 engaging recess 1354, thereby securing housing 1304 to grip ring 120, as shown in FIG. 25. Thus, grip ring 120 of outer sheath 102 may be secured to illuminating ring assembly 1300 by hinged attachment mechanism 1350, which is configured so that, when hinged attachment mechanism 1350 is in place and arms 1358, 1360 are brought together and locked in position, an inner circumference of hinged latching mechanism 1350 frictionally engages grip ring 120 and holds grip ring 120 in place to housing 1304.

Figure 27:
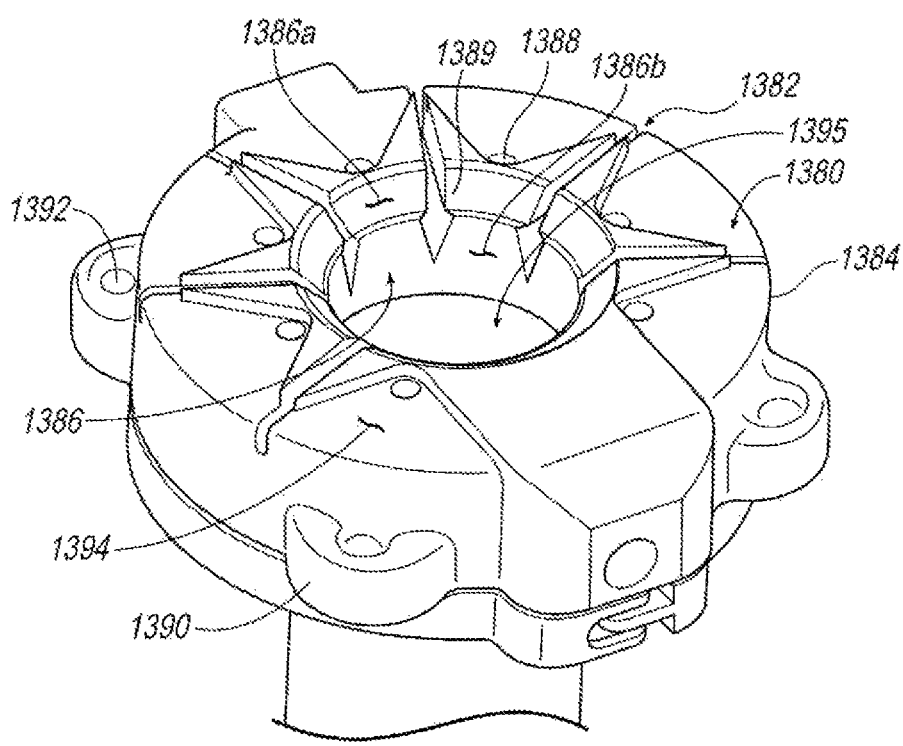
FIG. 27 is a top perspective view of the illuminating ring assembly of FIG. 22.

As shown in FIG. 27, housing 1380 of illuminating ring assembly 1300 has a cover 1380 that defines an exterior face 1394. A central opening 1395 is formed through cover 1380. Opening 1395 is configured to provide communication with an inner lumen of outer sheath 102 so as to permit one or more medical devices to be inserted therein.

In one exemplary arrangement, cover 1380 may be configured with one or more notches 1382. Each notch 1382 is configured to extend from inner perimeter 1386 of opening 1395 to an outer perimeter 1384 of wall member 1305. In one exemplary arrangement, inner perimeter 1386 of cover 1380 includes a beveled entry surface 1386a (best seen in FIG. 27) that joins an inner periphery surface 1386b that defines opening 1395. In this arrangement, ends of each notch 1382 at an edge of inner perimeter entry surface 1386a, notches 1382 may be tapered slightly outwardly. Inner periphery surface 1386b may further include notches 1389 that are aligned with notches 1382. Notches 1389 may be configured to taper inwardly in a V-shape along inner periphery 1386b. When aligned, each notch 1382 serves to receive and selectively retain a string or cord from a Neuro Pattie, other absorbent surgical sponge or other object to be temporarily positioned within outer sheath 102. The outwardly tapered notch ends of notches 1382 allow for some flexibility in movement of the string or cord while in the outer sheath 102.

In one exemplary arrangement, notches for retaining a Neuro Pattie, or the like, may be formed in an upper surface of grip ring 120 for those embodiments where no light illuminating ring assembly 1300 are utilized. Details of this configuration are further discussed in co-pending U.S. patent application Ser. No. 13/786,062.

In addition to notches 1382, a multiplicity of small openings 1388 may also be formed in housing 1380. Openings 1388 may be spaced equidistantly around inner perimeter 1386 of opening 1395 of housing 1380. In one exemplary configuration, openings 1388 may extend completely through external face 1394. In another exemplary arrangement, openings 1388 may extend only partially into external face 1394, but not entirely through external face 1394. A manipulation member, such as that illustrated in FIGS. 19A-19B, may be engaged with small openings 1388 and used to gently adjust the location of outer sheath 102. In yet another alternative arrangement, one or more radial projections 1390 may extend radially outwardly away from wall member 1305 of housing 1380. In one arrangement, projections 1390 may be equally spaced around wall member 1305 of housing 1380. Each projection 1390 may define a small hole 1392. Retaining members (not shown) may extend through small holes 1392 to loosely secure outer sheath 102 in place once outer sheath 102 is positioned within a patient. Suitable retaining members include, but are not limited to, bridle sutures, flexible bands with retaining hooks, or repositionable retractor arms.

Figure 28:
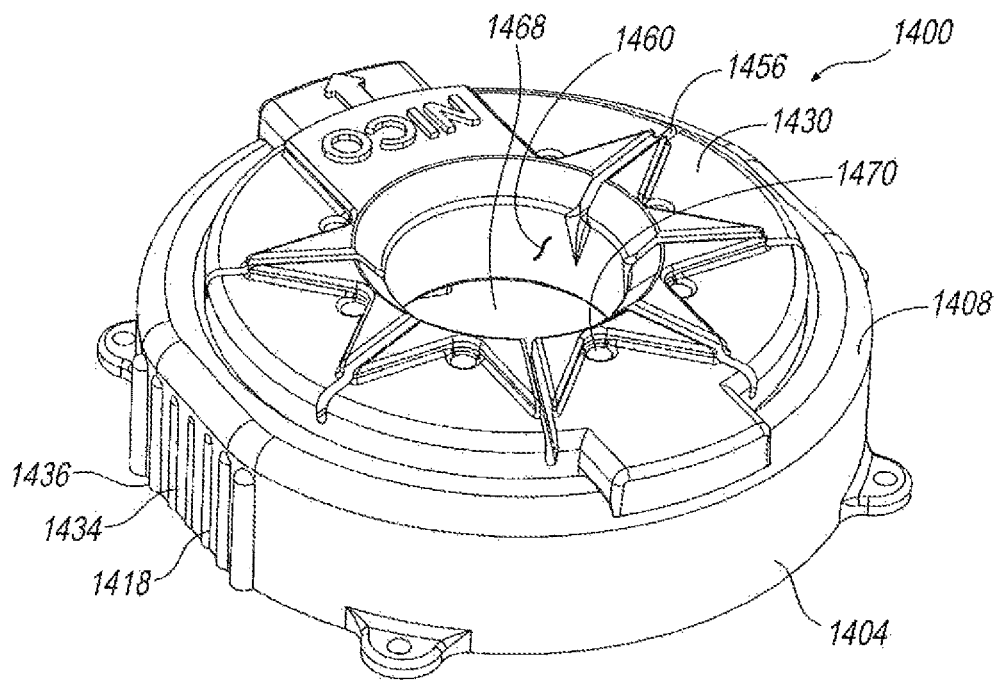
FIG. 28 is a top perspective view of an alternative illuminating ring assembly.
Figure 29:
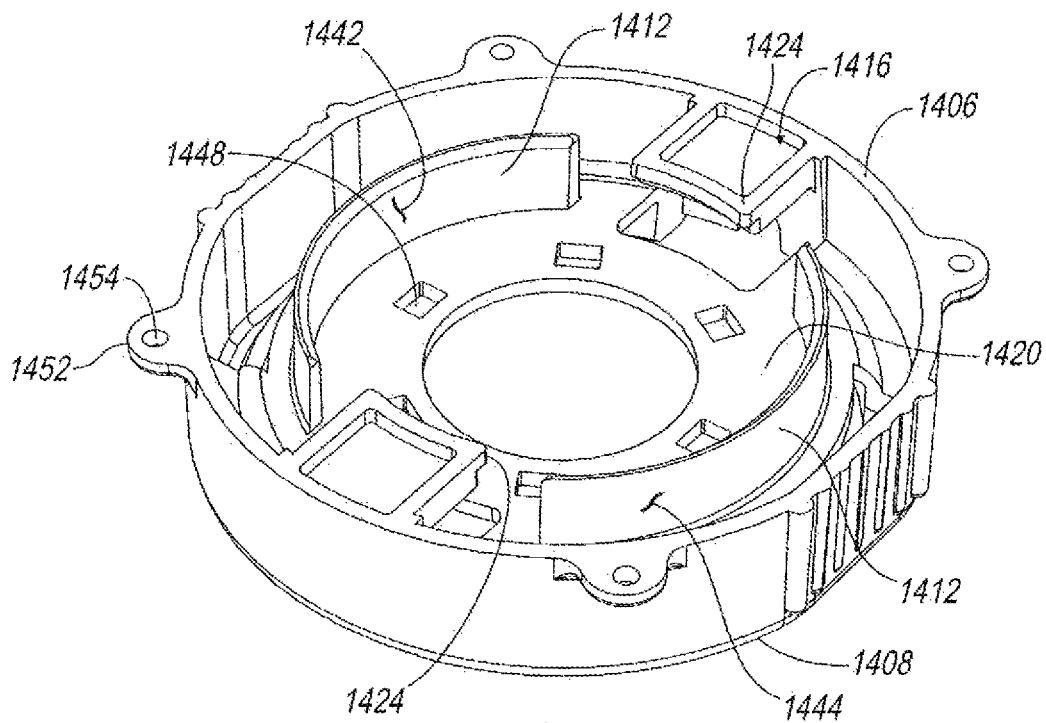
FIG. 29 is a bottom perspective view of the illuminating ring assembly of FIG. 28.

An alternative exemplary arrangement of illuminating ring 1400 is shown in FIGS. 28-29. Illuminating ring 1400 has a selectively flexible wall member 1404 that further includes a first circumferential edge 1406 (best seen in FIG. 27). A second circumferential edge 1408 may be disposed opposite to first circumferential edge 1406. A cover 1420 is connected to the wall member 1404. As may be seen in FIG. 29, wall member 1404 serves to define a cavity 1410 into which grip ring 120 may be received, as will be explained below in further detail.

Cover 1420 includes a generally central opening 1468 therethrough. An inner wall member 1460 extends between an inner perimeter of cover 1420 thereby defining an access opening configured to receive one or more surgical instruments. In one exemplary arrangement, a top portion of inner wall member 1460 may be beveled inwardly so as to direct surgical instruments and other items introduced through opening 1468.

Disposed within cavity 1410 is at least one locating member 1412. Locating member 1412 extends from an inner surface of cover 1420, so as to extend substantially perpendicularly therefrom. Each locating member 1412 has an inside surface 1442 and an outside surface 1444. Locating members 1412 are configured to accept a radial portion of an outside perimeter of a grip ring 120 attached to an outer sheath 102. In one exemplary arrangement, locating members 1412 are arranged in an opposing manner.

One or more retaining tabs 1416 extend radially inward into cavity 1410 from first edge 1406 of wall member 1404. In one exemplary arrangement, retaining tabs 1416 are configured to be arranged in a generally perpendicular direction from wall member 1404. Each of the retaining tabs 1416 may further include a lip 1424 extending from tab 1416 toward the center of cavity 1410, as will be explained in further detail below. In one exemplary arrangement, two retaining tabs 1416 are provided, which may be arranged in an opposing manner, as illustrated in FIG. 29.

As best seen in FIGS. 28-29, one or more gripping areas 1418 may be disposed on the outer perimeter of wall member 1404. Gripping areas 1418 may have a textured surface, such as, for example, alternating grooves 1434 and ridges 1436 disposed thereon. In one exemplary arrangement, two gripping areas 1418 are disposed opposite one another on wall member 1404. In one exemplary arrangement, tabs 1416 and gripping areas 1418 are arranged in an alternating manner. Wall member 1404 is sufficiently flexible such that when gripping areas 1418 are biased toward one another, wall member 1404 flexes, causing tabs 1416 to flex upwardly. Tabs 1416 may be flexed a sufficient amount to allow the outer perimeter of grip ring 120 to be positioned between lips 1424 of tabs 1416. Grip ring 120 may then be introduced to cavity 1410 defined by wall member 1404, and positioned adjacent inner surface of cover 1420. Inside surface 1442 of the at least one locating member 1412 may be positioned nearly adjacent the outer perimeter of grip ring 1426, thereby serving to properly position grip ring 1426. Once grip ring 1426 is properly positioned, gripping areas 1418 may be released to their unbiased positions, thereby releasing tabs 1416 to their original positions. When tabs 1416 return to the original positions, lips 1424 extend a sufficient amount over a bottom edge of grip ring 1426 to prevent grip ring 1426 from being easily removed from illuminating ring 1400, thereby securing grip ring 1426 in place.

Illuminating ring 1400 may further include a plurality of openings 1448 in inside surface of cover 1420. A plurality of light elements (not shown) may be disposed in alignment with openings 1448. Light elements may be incorporated into a circuit board (not shown), which circuit board may be generally ring-shaped, and configured to fit within outer perimeter of wall member 1404. Light elements and circuit board may be disposed between inside surface of cover 1420 and a top portion 1430 of illuminating ring 1400. Wires (not shown) may extend from circuit board through openings (not shown) in wall member 1404 or top portion 1430, and be electrically connected to a remote power source.

Illuminating ring 1400 may also have one or more retaining elements 1452 extending radially outward from wall member 1404. In one exemplary arrangement, retaining elements 1452 extend radially outward from adjacent to first circumferential edge 1406 of wall member 1404. Retaining elements 1452 may each define a small hole 1454. Suitable retaining members may extend through small holes 1454 in the plurality of retaining elements 1452, and loosely attach illuminating ring 1400 to a surface. Suitable retaining members include, but are not limited to, bridle sutures, flexible bands with retaining hooks, or repositionable retractor arms.

At least one notch 1456 may extend from an outer perimeter to the inner perimeter of cover 1430. The at least one notch 1456 may be configured so to accept and selectively retain a string or cord from a Neuro Pattie or other absorbent surgical sponge with an attached string or cord, as described above in connection with FIG. 27.

At least one small opening 1470 may be disposed on cover 1430. The at least one small opening 1470 may be configured to accept a portion of a manipulation member. Examples of manipulation members 700, 700' are illustrated in FIGS. 19A-19B. A hook element 706 of manipulation member 700, 700' may engage with small opening 1470, and handle 702 of manipulation member 700, 700' may be manipulated to gently reposition illuminating ring 1400 and outer sheath (not shown).

Another alternative arrangement of an illuminating ring assembly 1500 is shown in FIGS. 30-33. Illuminating ring assembly 1500 is similar to illuminating ring assembly 1300 shown in FIG. 22. Illuminating ring assembly 1500 includes a housing 1504 comprising a wall member 1505 and a cover 1530. Wall member 1504 extends around the outer perimeter of illuminating ring 1500 and extends downwardly from cover 1530 to define a generally circular cavity. A light member 1503 is positioned within the cavity formed by housing 1504. Light member 1503 may be configured as a substantially planar ring, wherein an outer perimeter of light member 1503 fits within the cavity defined by wall member 1504.

Housing 1504 (and light member 1503) further includes an opening 1507 therethrough that is configured to receive medical instruments therein, as described above. Extending outwardly from a bottom surface of wall member 1505 is a securing member 1546. In one exemplary configuration, wall member 1505 may be provided with one or more protrusions 1542, 1544 (best seen in FIG. 33) that extend radially outwardly from a periphery of wall member 1504 upon which securing member 1546 may be mounted. While not shown, it is understood that a positioning member similar to that shown in FIG. 22 and described above, may also be provided. Protrusions 1542, 1544 may be located opposite one another, although other arrangements are also contemplated.

Figure 33:
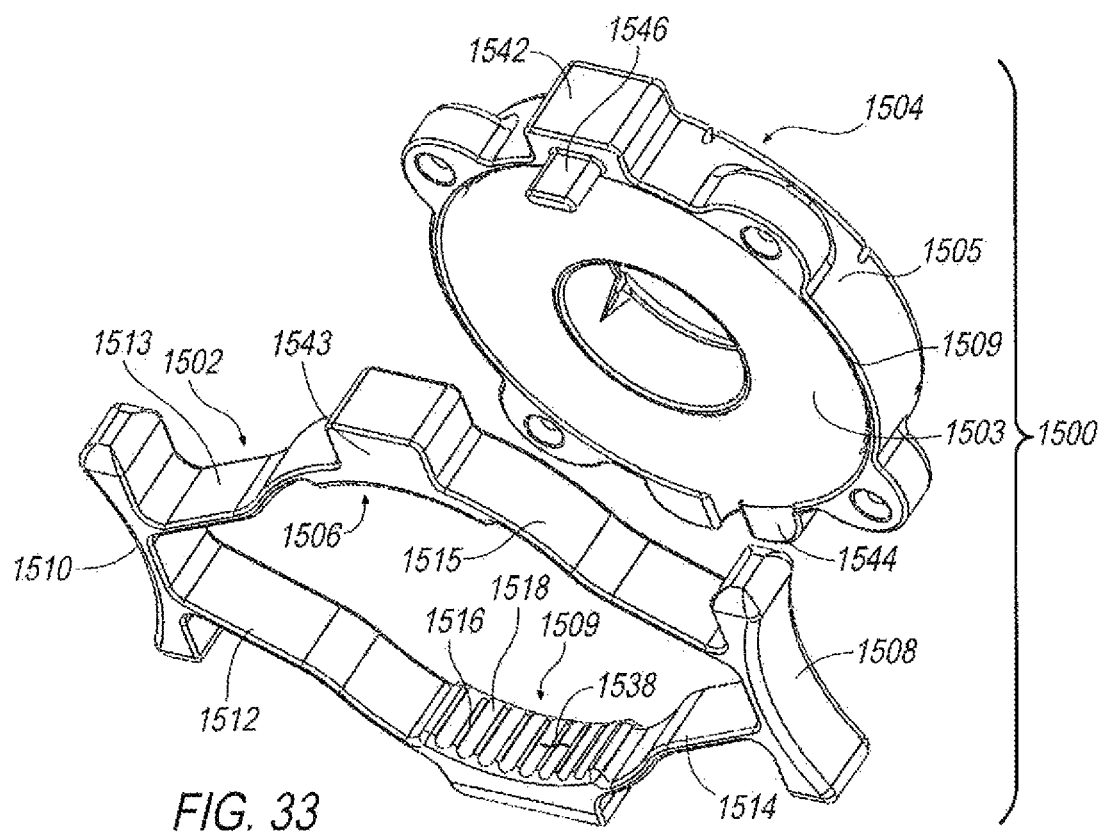
FIG. 33 is an exploded view of the illuminating ring assembly of FIG. 32.

Illuminating ring assembly 1500 further comprises a spring clamp 1502 that may be selectively secured to wall member 1504. Spring claim 1502 may be configured as a unitary member, as illustrated in FIG. 33. Spring clamp 1502 may further include a first and a second gripping portion 1506, 1509, an attachment portion 1543, and finger rests 1508, 1510. At least one opening (not shown) may be formed on an end face of attachment portion 1543 of spring clamp 1502. The opening is configured to selectively receive securing member 1546 to secure spring clamp 1502 to housing member 1504.

First and second gripping portions 1506, 1509 are disposed substantially opposite one another. First gripping portion 1506 has a face surface 1536, and second gripping portion 1509 has a face surface 1538. Face surfaces 1536, 1538 of gripping portions 1506, 1509 may face one another. Attachment portion 1543 may be disposed on the anterior surface 1552 of first gripping portion 1506.

Figure 32:
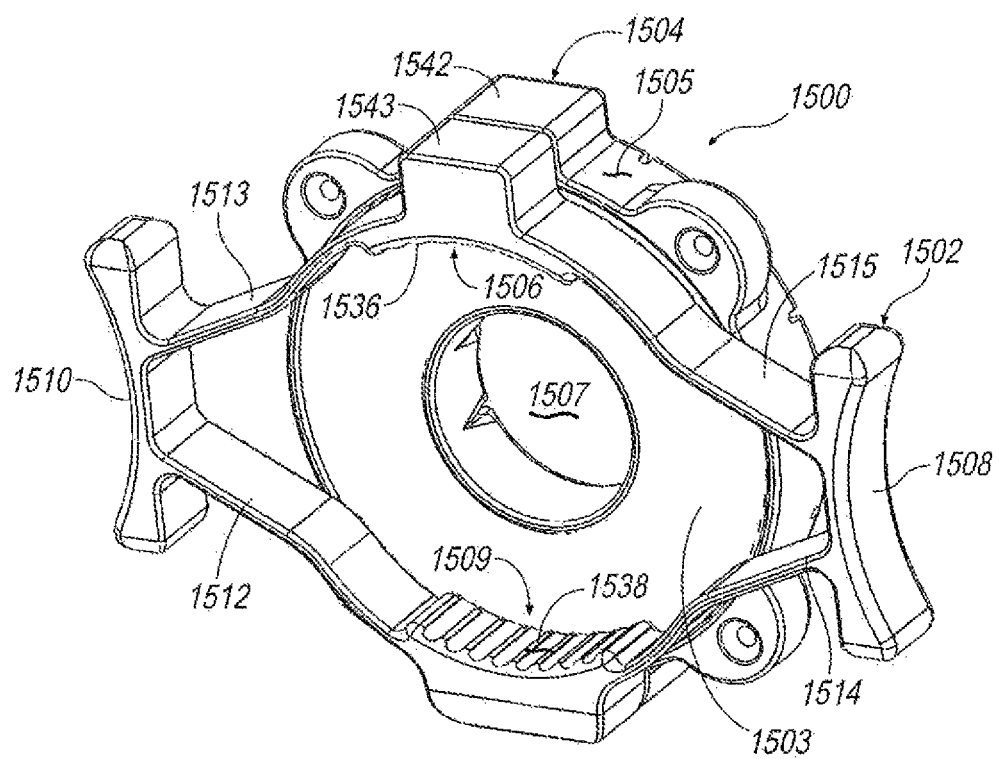
FIG. 32 is a perspective view of the illuminating ring assembly of FIG. 30.

Finger rests 1508, 1510 are disposed substantially opposite one another, and each finger rest 1508, 1510 is disposed between first and second gripping portions 1506, 1509. As shown in FIG. 32, first gripping portion 1506 has two arms 1512, 1513, each extending from first gripping portion 1506 to one of finger rests 1508, 1510. Second gripping portion 1509 also has two arms, 1514, 1515, each extending from second gripping portion 1509 to one of finger rests 1508, 1510. The portion of each arm 1512, 1513, 1514, 1515 adjacent the gripping portion 1506, 1509 of spring clamp 1502 may be configured so as to accommodate grip ring 120 therein. Each arm 1512, 1513, 1514, 1515 may have sufficient flexibility to allow it to deviate from its usual configuration so as to allow gripping portions 1506, 1509 to move apart from one another in response to finger rests 1508, 1510 being biased toward one another to facilitate engagement and disengagement of spring clamp 1502, housing 1504 and grip ring 102.

Figure 31:
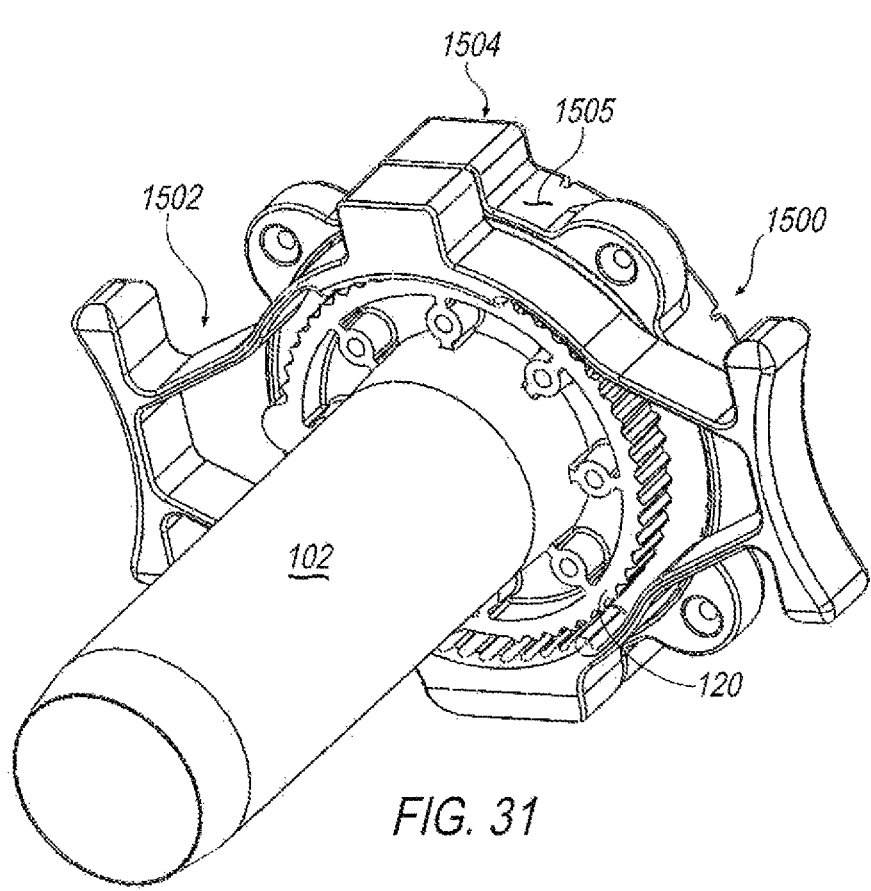
FIG. 31 is a rear perspective view of the illuminating ring assembly of FIG. 30.

As illustrated in FIG. 33, face surfaces 1536, 1538 of gripping portions 1506, 1509 may be configured with sufficient curvature to allow them to accommodate a portion of a grip ring 120 of an outer sheath 102 (as best shown in FIG. 31). Face surfaces 1536, 1538 may have ridges 1516 and grooves 1518 disposed on them, which ridges 1516 and grooves 1518 may be configured in such a way frictionally engage ridges and grooves that may be disposed on grip ring 120. In one exemplary arrangement, the ridges 1516 and grooves 1518 are sized such that corresponding ridges and grooves on grip ring 120 may be meshed with ridges 1516 and grooves 1518.

Finger rests 1508, 1510 may have a curvature that will allow fingers to comfortably rest in finger rest 1508, 1510. Additionally, finger rests 1508, 1510 may have a textured surface to provide purchase for fingers.

Finger rests 1508, 1510 may be biased toward one another. Biasing finger rests 1508, 1510 toward one another will move second gripping portion 1509 away from first gripping portion 1506 while first gripping portion 1508, which is secured to housing 1504, remains stationary in relation to illuminating ring 1500. Once second gripping portion 1509 has been moved a sufficient distance away from first gripping portion 1506, grip ring 120 may be inserted between first and second gripping portions 1506, 1509, and finger rests 1508, 1510 may be released to their unbiased positions. Releasing finger rests 1508, 1510 may cause second gripping portion 1509 to move toward first gripping portion 1506, and cause both gripping portions 1506, 1509 to contact outer perimeter of grip ring 1526, thus securing grip ring 120 to housing 1504. Spacing of ridges 1516 and grooves 1518 on faces 1536, 1538 of gripping portions 1506, 1509 may coincide with the spacing of ridges and grooves of grip ring 120, providing a larger contact area between grip ring 120 and spring clamp 1502 for a more secure connection.

To remove grip ring 1526 from housing 1504 and/or grip ring 120, finger rests 1508, 1510 may be biased toward one another, causing second gripping portion 1509 to move away from first gripping portion 1506, thus releasing grip ring 120. Once grip ring 120 has been released, it may be separated from housing 1504. Further, housing 1504 may be separated from spring clamp 1502. More specifically, protuberance 1546 may be disengaged from the opening disposed on attachment mechanism 1543.

Figure 30:
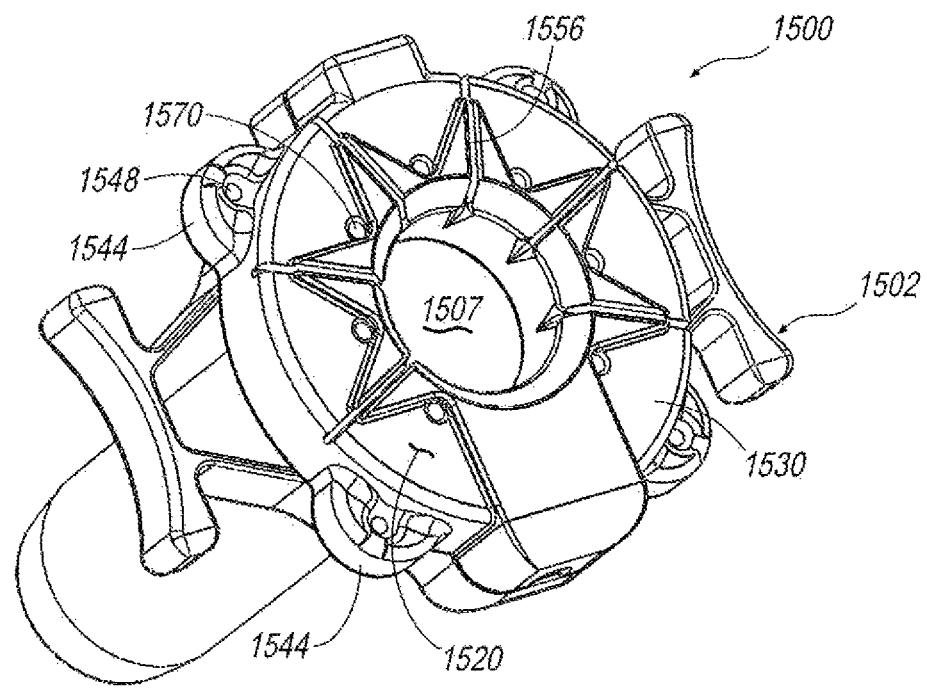
FIG. 30 is a perspective view of an illuminating ring assembly in an assembled configuration with the other sheath.

Referring now to FIG. 30, At least one notch 1556 may be formed on an outer surface 1520 of cover 1530 so as to extend from an outer perimeter of cover 1530 to the perimeter of opening 1507. The at least one notch 1556 may be configured so to accept and selectively retain a string or cord from a Neuro Pattie or other absorbent surgical sponge with an attached string or cord, as described above in connection with FIG. 27. In one exemplary configuration, a plurality of notches 1556 may be provided, and the notches 1556 may be disposed equidistantly on the cover 1530.

At least one small opening 1570 may be disposed on cover 1530. The at least one small opening 1570 may be configured to accept a portion of a manipulation member. Examples of manipulation members 700, 700' are illustrated in FIGS. 19A-19B. A hook element 706 of manipulation member 700, 700' may engage with small opening 1470, and handle 702 of manipulation member 700, 700' may be manipulated to gently reposition illuminating ring 1400 and outer sheath (not shown).

At least one retaining element 1544 may extend radially outward from wall member 1504 of cover 1504. Each of the at least one retaining elements 1544 may define a hole 1548. A suitable retaining member may extend through each hole 1548 and may be used to secure illuminating ring 1500 to a surface. Suitable retaining members include, but are not limited to, bridle sutures, flexible bands with retaining hooks, or repositionable retractor arms.

Figure 34:
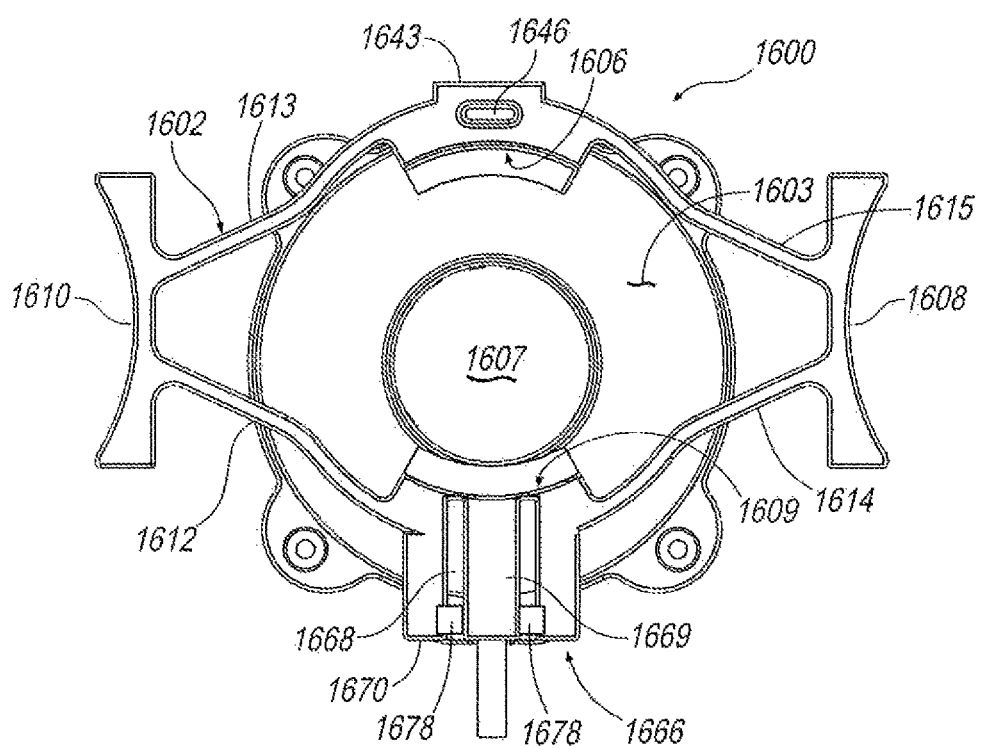
FIG. 34 is a rear elevational view of an alternative arrangement of an illuminating ring assembly in an assembled configuration.
Figure 35:
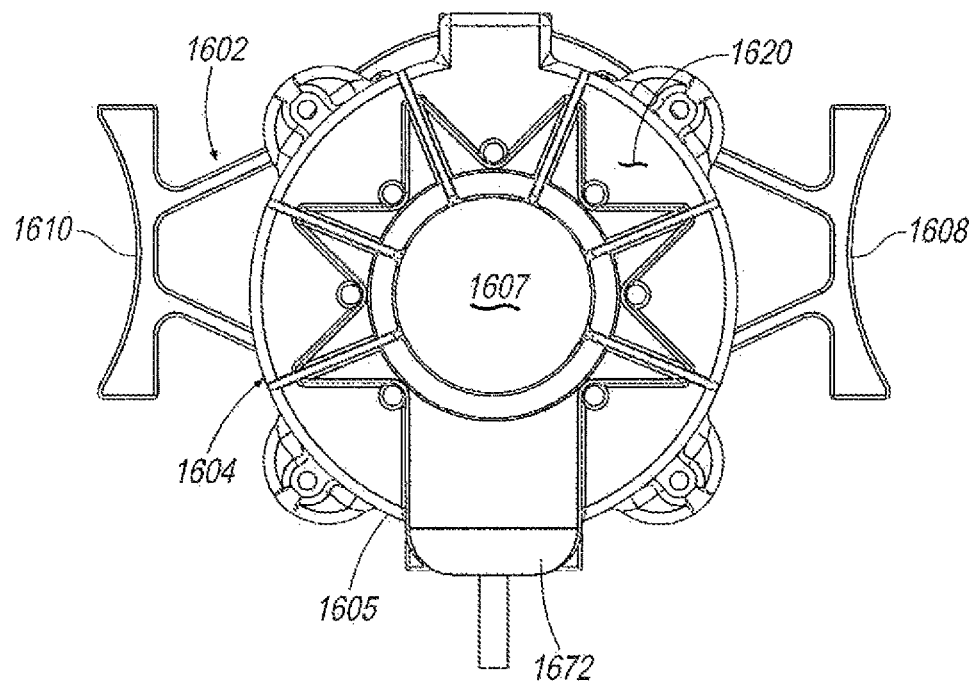
FIG. 35 is a front elevational view of the illuminating ring assembly of FIG. 34.
Figure 36:
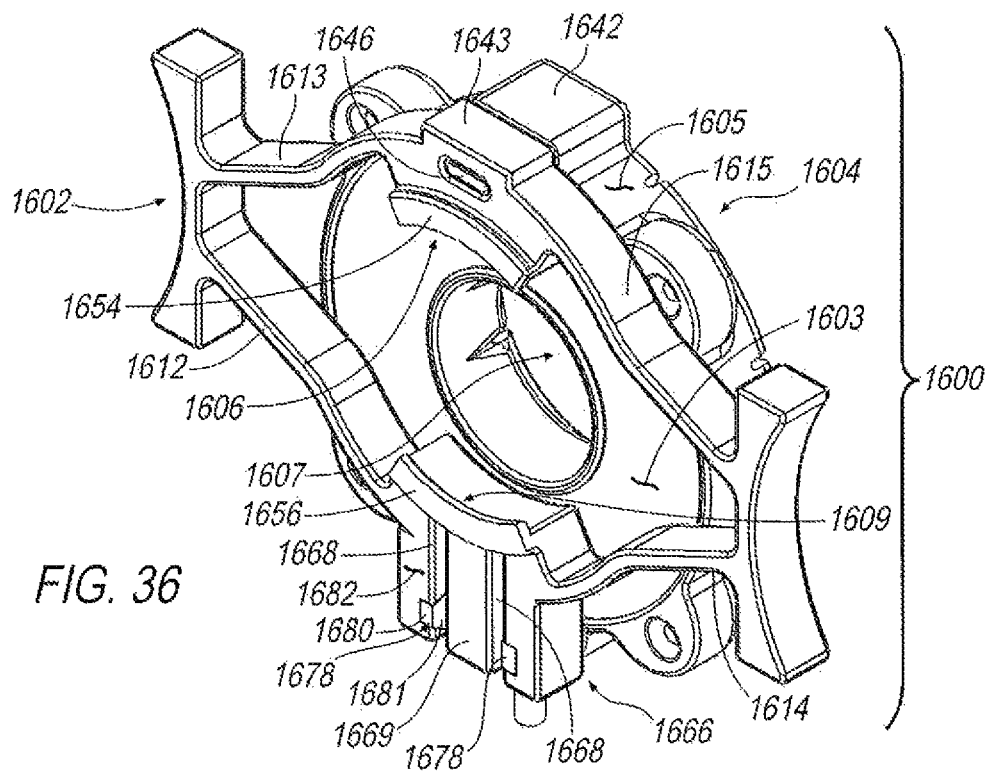
FIG. 36 is a perspective view of the illuminating ring assembly of FIG. 34.

Another exemplary configuration of an illuminating light ring assembly 1600 is shown in FIGS. 34-36. Light ring assembly 1600 is similar to the configuration shown in FIGS. 30-33. Light ring assembly 1600 includes a cover 1604 that is configured substantially the same as cover 1504, a light ring 1603 disposed within cover 1604, as well as a spring clamp 1602.

The exemplary alternative arrangement of spring clamp 1602 may have a first and a second gripping portion 1606, 1609, an attachment portion 1643, a slidable portion 1666 and finger rests 1608, 1610. First and second gripping portions 1606, 1609 are disposed substantially opposite one another, as seen in FIGS. 34-36. Attachment portion 1643 is disposed on the anterior surface of first gripping portion 1606, and is configured to be selectively secured to cover 1604. More specifically, attachment portion 1643 of spring clamp 1602 includes an opening that is configured to receive a protuberance 1646 of cover 1604, as shown in FIG. 34.

Slidable portion 1666 is disposed on the anterior surface of second gripping portion 1609. Slidable portion 1666 includes an exterior edge 1670 opposite second gripping portion 1606. At least one slot 1668 is formed in slidable portion 1666. Slot 1668 extends from exterior edge 1670 toward second gripping portion 1609. In one exemplary arrangement, a pair of slots 1668 is provided, with a land member 1669 therebetween. Further detail concerning the slots 1668 will be provided below.

Housing 1604 may have a projection member 1672 extending radially outward from wall member 1605, as illustrated in FIG. 35. At least one gripping member 1678 may be disposed on projection 1672. Each gripping member 1678 may be configured so as to be engageable with one of the at least one slots 1668. In one exemplary configuration, each gripping member 1678 is configured as having a foot member 1680 that is oriented transversely from a leg member 1681. The leg member 1681 is configured to be disposed within slot 1668, with foot member overlying an outside surface 1682 of slidable portion 1666, as best seen in FIG. 36.

Similar to finger rests 1508, 1510 in spring clip 1502, finger rests 1608, 1610 are disposed substantially opposite one another, and each finger rest 1608, 1610 is disposed between first and second gripping portions 1606, 1609. First gripping portion 1606 has two arms 1612, 1613, each extending from first gripping portion 1606 to one of finger rests 1608, 1610. Second gripping portion has two arms, 1614, 1615, each extending from second gripping portion 1609 to one of finger rests 1608, 1610. The portion of each arm 1612, 1613, 1614, 1615 adjacent the gripping portion 1606, 1609 of spring clamp 1602 may be configured so as to accommodate a radial portion of the outer circumference of grip ring 1626. Each arm 1612, 1613, 1614, 1615 may have sufficient flexibility to allow it to deviate from its usual configuration so as to allow gripping portions 1606, 1607 to move apart from one another if finger rests 1608, 1610 are biased toward one another.

Gripping portions 1606, 1609 may be configured with sufficient curvature to allow them to accommodate a radial portion of grip ring of an outer sheath (not shown). Gripping portions 1606, 1609 may each be provided with a retaining lip 1654, 1656 disposed along an edge of gripping portion 1606, 1609. Retaining lips 1654, 1656 may be oriented so as to be substantially parallel to a plane of the top surface 1620 of cover 1604. Each lip 1654, 1656 is configured to allow a grip ring to be secured between cover 1604 and lips 1654, 1656 of spring clamp 1602, and held in place between gripping portions 1606, 1609.

Finger rests 1608, 1610 each have an outwardly facing surface that may have a curvature that will allow fingers to comfortably rest in finger rest 1608, 1610. Finger rests 1608, 1610 may be selectively biased toward one another. When finger rests 1608, 1610 are so biased, second gripping portion 1609 may be moved away from first gripping portion 1606 to permit selective engagement with a grip ring.

Spring clamp 1602 is also configured to be positively engaged with cover 1604, which houses light ring 1603 therein. More specifically, once the grip ring of an outer sheath is retained to spring clamp 1602 (as described above), slidable portion 1666 is engaged with projection member 1672 of cover 1604. More specifically, gripping portions 1678 are received within slots 1668 and spring clamp 1602 is slid onto cover 1604 until attachment portion 1643 of spring clamp 1602 aligns with a protrusion 1642 disposed on cover 1604. Protuberance 1646 may then be received within an opening (best seen in FIGS. 34 and 36). In this manner, spring clamp 1502 is positively secured to cover 1604 (with light ring 1603 disposed therein) at two locations; via protuberance 1646 with an opening on attachment portion 1643 and via engagement of gripping portions 1678 with slots 1668. The grip ring (not shown), will thereby be secured between first and second gripping portions 1606, 1609 of spring clamp 1602, within the cavity of cover 1604 between a top surface 1620 and retaining lips 1654, 1656.

To remove cover 1604 (and light ring) from a grip ring, the finger rests 1608, 1610 may be biased toward one another, causing second gripping portion 1609 to move away from first gripping portion 1606 a sufficient amount to dislodge protrubarance 1646 from the opening of attachment portion 1643. Spring clamp 1602 may then be slid with respect to gripping member 1678 so as to free gripping member 1678 from slots 1680, thereby releasing spring clamp 1602 from cover 1604. Once dislodged from cover 1604, finger rests 1608, 1610 may be biased toward one another to flex gripping portions 1606, 1609 sufficiently that the grip ring may be released from retaining lips 1654, 1656.

Another exemplary alternative configuration of an illuminating ring assembly 1700 is shown in FIGS. 37-41. Illuminating ring assembly 1700 includes a cover portion 1704 and an attachment portion 1702. In this configuration, attachment portion 1702 is integral with cover portion 1704 such that illuminating ring assembly 1700 is a unitary structure. An annular gap 1707 is formed about a substantial periphery of attachment portion 1702 to provide flexibility to attachment portion 1702.

Cover portion 1704 is generally defined by a cover surface 1720 and a wall member 1705 extending from cover surface 1720. The cover surface 1720 cooperates with the wall member 1705 to define a cavity therein (best seen in FIGS. 38 and 41). An illuminating ring 1703 is disposed within the cavity, but does not extend the entire depth of the cavity. Extending through cover 1704 (as well as illuminating ring 1703) is an opening 1707, through which surgical instruments may be received.

Attachment portion 1702 also has a generally ring-shape and is defined by first and second wall sections 1706, 1708. Wall sections 1706, 1708 are separated from one another so as to form a gap 1709 therebetween. Each wall section 1706, 1708 is defined by first and second ends 1706a, 1706b and 1708a, 1708b, respectively. First ends 1706a, 1708a each include a flexible finger tab 1710. Finger tabs 1710 have a thickness that is substantially less than the reminder of wall sections 1706, 1708, to which each finger tab 1710 is connected. Second ends 1706b, 1708b may slope downwardly toward an end of a retaining lip 1712a, 1712b. Retaining lips 1712a, 1711b are generally curved along the inside periphery of the cavity formed by wall member 1705.

Connection of grip ring 120 from an outer sheath 102 to illuminating ring assembly 1700 will now be described. First, finger tabs 1710 are pressed toward one another. Such an action causes retaining lips 1712a, 1712b to flex, lifting up a top edge thereof. This action permits grip ring 120 to be received within the cavity. Finger tabs 1710 may then be released, which returns retaining lips 1712a, 1712b to its retaining position. In the retaining position, the top edge of the retaining lips 1712a, 1712b overlay an outer periphery of grip ring 120, thereby capturing grip ring 120 within the cavity of illuminating ring assembly 1700 so as to secure illuminating ring assembly 1700 to outer sheath 102.

Figure 37:
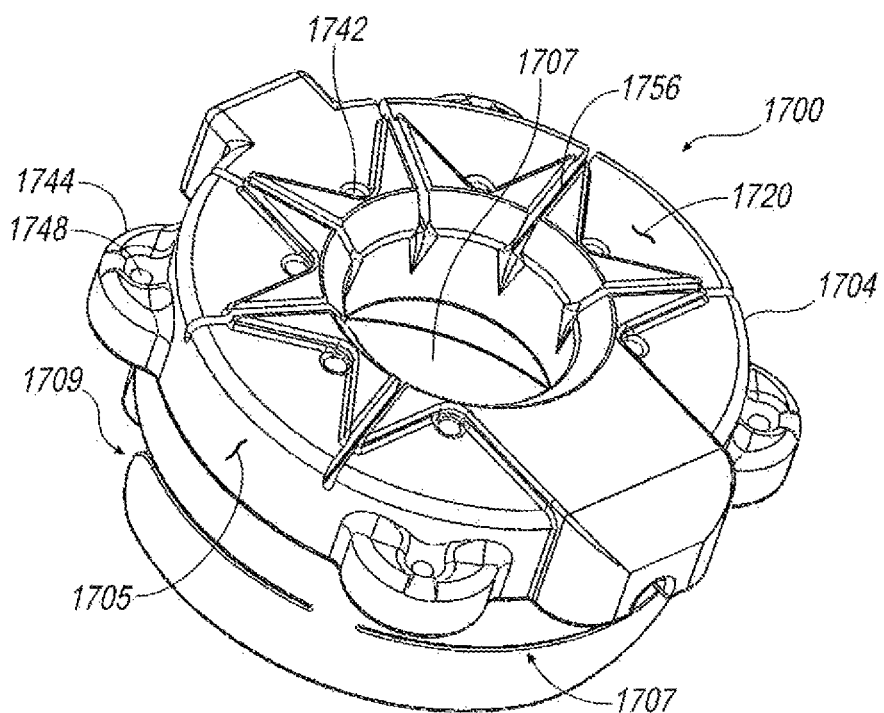
FIG. 37 is a top perspective view of an alternative illuminating ring assembly.
Figure 38:
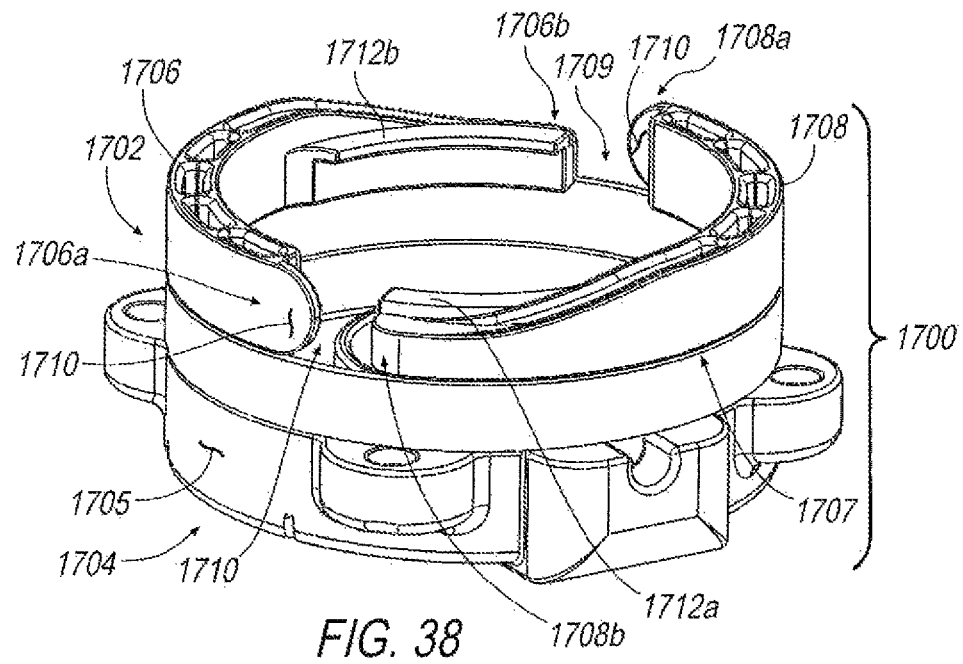
FIG. 38 is a perspective elevational view of the illuminating ring assembly of FIG. 37.
Figure 39:
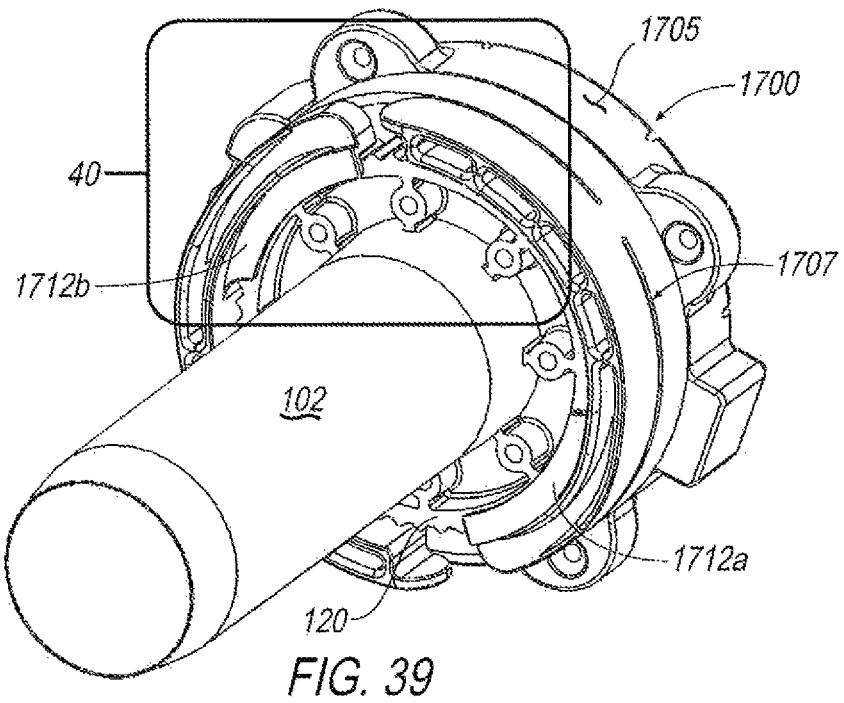
FIG. 39 is a perspective view of the illuminating ring assembly of FIG. 37, assembled in an outer sheath.
Figure 40:
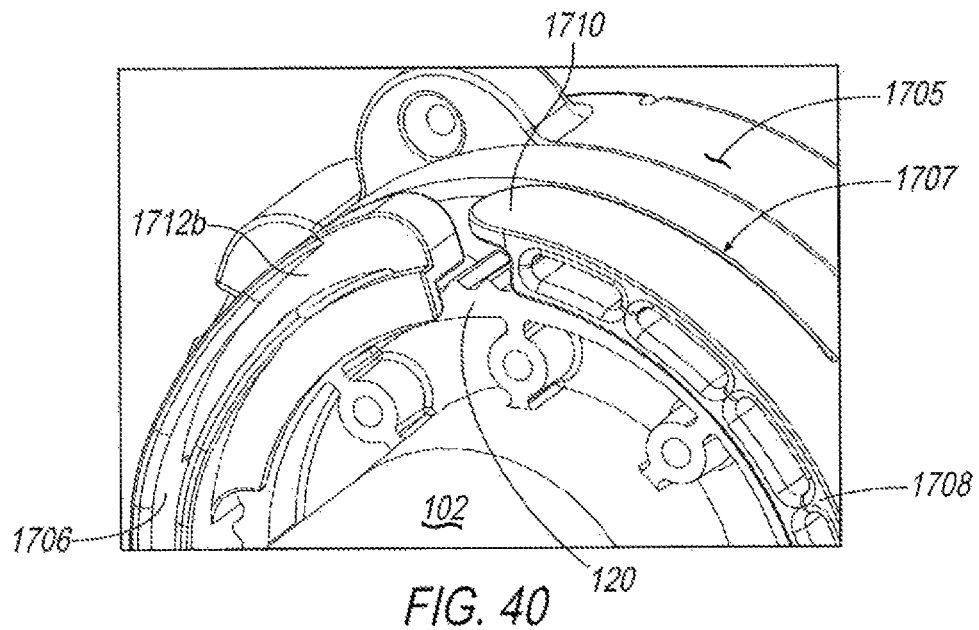
FIG. 40 is an enlarged view of the illuminating ring assembly taken from area 40 in FIG. 39.
Figure 41:
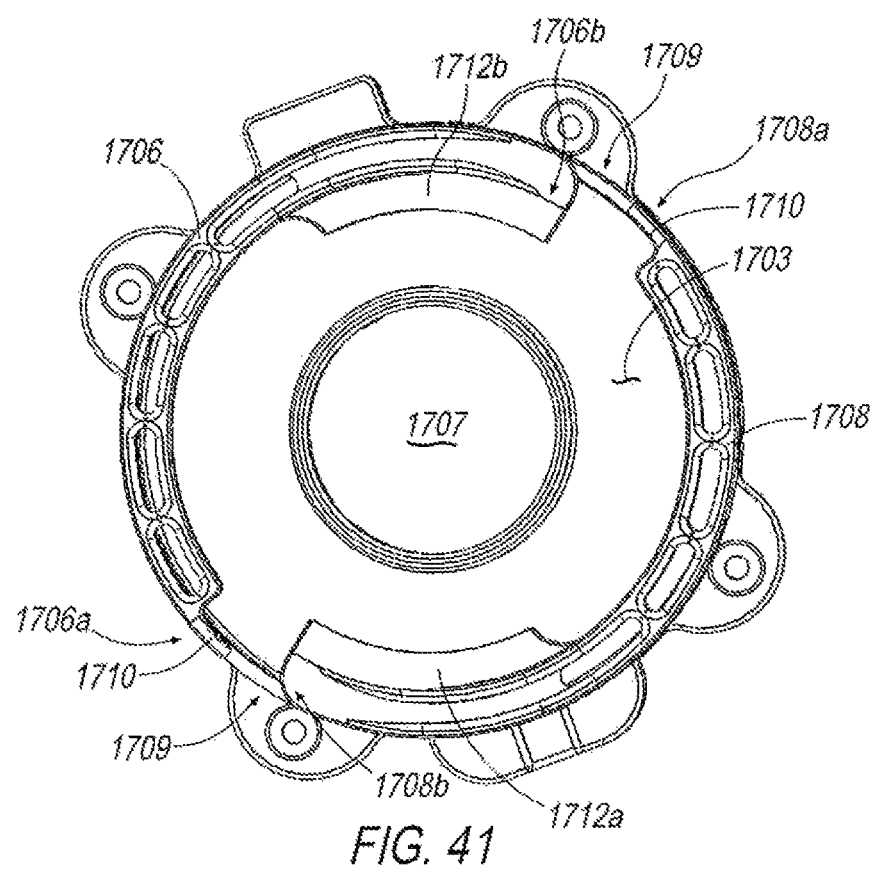
FIG. 41 is a plan view of the illuminating ring assembly of FIG. 37.

Referring to FIG. 37, additional alternative features of illuminating ring assembly 1700 will be described. Similar to previously described configurations, cover 1720 may be provided with at least one notch 1756. The at least one notch 1756 may extend from the outer perimeter of cover 1720 to the perimeter of opening 1707. The at least one notch 1756 may be configured so as to accommodate a string or cord from a Neuro Pattie or other absorbent surgical sponge with a string or cord attached.

At least one small opening 1742 may be disposed on a surface of cover 1720 of illuminating ring assembly 1700. A manipulation member may be used in conjunction with small openings 1742 to gently adjust position of outer sheath 102. Examples of manipulation members 700 and 700' are illustrated in FIGS. 19A-19B.

At least one retaining element 1744 may be provided. Retaining elements extend radially outward from wall member 1705 of cover 1704. Each of the retaining elements 1744 may include a hole 1748. A suitable retaining member may extend through each hole 1748 and may be used to secure illuminating ring assembly 1700 to a surface. Suitable retaining members include, but are not limited to, bridle sutures, flexible bands with retaining hooks, or repositionable retractor arms.

It will be appreciated that the surgical access system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A surgical access system, comprising:
   an outer sheath defined by a proximal end and a distal end and having a lumen extending between the proximal end and distal end;
   an obturator defined by a first end and a second end and having a distal tip disposed on the second end of the obturator, wherein the obturator is removably received within the outer sheath such that the distal tip is configured to protrude proximally from the distal end of the outer sheath when in an introducing configuration;
   at least one light element disposed entirely within a housing secured to a proximal end face of the outer sheath such that the at least one light element is positioned above the lumen of the outer sheath, wherein the at least one light element provides light to a surgical corridor via the outer sheath.

2. A surgical access system of claim 1, further including a selectively removable attachment mechanism configured to selectively attach the housing to the proximal end face.

3. A surgical access system of claim 1, wherein the housing includes an opening that axially aligns with the lumen of the outer sheath to allow for the introduction of surgical instruments into the outer sheath when the obturator is removed.

4. A surgical access system of claim 1, wherein at least a portion of the outer sheath is frosted.

5. A surgical access system of claim 1, wherein the proximal end of the outer sheath includes a locating member that operatively connects the housing to the outer sheath in a predetermined position.

6. A surgical access system of claim 5, wherein the locating member extends outwardly from an outer periphery of the proximal end of the outer sheath.

7. A surgical access system of claim 1, wherein the at least one light element is fixedly mounted to a surface of the housing and oriented toward the lumen of the outer sheath when mounted to the outer sheath.

8. A surgical access system of claim 7, wherein each at least one light element is electrically connected to a remote power source.

9. A surgical access system of claim 1, wherein the light from the at least one light element is directed from the proximal end of the outer sheath down the lumen of the outer sheath.

10. A surgical access system of claim 1, wherein the at least one light element includes LED lights.

11. A surgical access system of claim 10, wherein the at least one light element is configured to emit different combinations of frequencies of light that cooperate with fluorescing dyes.

12. A surgical access system of claim 1, wherein the outer sheath includes a manipulation ring mounted to the proximal end of the outer sheath.

13. A surgical access system of claim 12, wherein the at least one light element is mounted adjacent to the manipulation ring.

14. A surgical access system, comprising:
an outer sheath defined by a proximal end and a distal end and having a lumen extending between the proximal end and distal end;
an obturator defined by a first end and a second end and having a distal tip disposed on the second end of the obturator, wherein the obturator is removably received within the outer sheath such that the distal tip is configured to protrude proximally from the distal end of the outer sheath when in an introducing configuration;
at least one light element disposed within a housing that is secured to a manipulation ring operatively connected to the proximal end of the outer sheath, wherein the at least one light element is oriented within the housing such that the at least one light element is positioned above the lumen of the outer sheath so as to direct light down through the lumen of the outer sheath.

15. A surgical access system, comprising:
an outer sheath defined by a proximal end and a distal end and having a lumen extending between the proximal end and distal end;
an obturator defined by a first end and a second end and having a distal tip disposed on the second end of the obturator, wherein the obturator is removably received within the outer sheath such that the distal tip is configured to protrude proximally from the distal end of the outer sheath when in an introducing configuration;
at least one light element disposed entirely within a housing secured to a manipulation ring operatively connected to the proximal end of the outer sheath, wherein the at least one light element is oriented within the housing such that the at least one light element is positioned above the lumen of the outer sheath, wherein the at least one light element provides light to a surgical corridor via the outer sheath.

16. A surgical access system of claim 15, further including a selectively removable attachment mechanism configured to selectively attach the housing to the proximal end.

* * * * *